(12) United States Patent
Formica et al.

(10) Patent No.: US 12,303,647 B2
(45) Date of Patent: *May 20, 2025

(54) HUMIDIFICATION INTERFACE ARRANGEMENTS

(71) Applicant: ResMed Pty Ltd, Bella Vista (AU)

(72) Inventors: Justin John Formica, Sydney (AU); Dimitri Marco Maurer, Gosford (AU); Kenneth John Taylor, Sydney (AU); Jeremy William Workman, Blue Mountains (AU); Andrew Chan, Sydney (AU); Sebastien Deubel, Sydney (AU); Craig Edward Harris, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/384,596

(22) Filed: Oct. 27, 2023

(65) Prior Publication Data
US 2024/0058565 A1 Feb. 22, 2024

Related U.S. Application Data

(63) Continuation of application No. 16/850,047, filed on Apr. 16, 2020, now Pat. No. 11,839,720.
(Continued)

(51) Int. Cl.
*A61M 16/16* (2006.01)
*A61M 16/00* (2006.01)
(Continued)

(52) U.S. Cl.
CPC ........ *A61M 16/16* (2013.01); *A61M 16/0816* (2013.01); *A61M 16/0875* (2013.01);
(Continued)

(58) Field of Classification Search
CPC .............. A61M 16/16; A61M 16/0816; A61M 16/0875; A61M 16/1095; A61M 16/0066;
(Continued)

(56) References Cited

U.S. PATENT DOCUMENTS

| 4,028,444 A | 6/1977 | Brown et al. |
| 4,782,832 A | 11/1988 | Trimble et al. |

(Continued)

FOREIGN PATENT DOCUMENTS

| EP | 1952746 A2 | 8/2008 |
| GB | 2 321 668 A | 8/1998 |

(Continued)

OTHER PUBLICATIONS

"Respiratory Physiology", by John B. West, Lippincott Williams & Wilkins, 9th edition published 2012 (8 pages).
(Continued)

*Primary Examiner* — Kendra D Carter
*Assistant Examiner* — Maap Ellabib
(74) *Attorney, Agent, or Firm* — Nixon & Vanderhye P.C.

(57) ABSTRACT

An apparatus for generating and providing a pressurized breathable gas to a patient's airways includes a respiratory pressure therapy (RPT) device having an engagement port pneumatically and electrically coupled to the RPT device, and an air delivery tube configured to engage the engagement port so as to pass a flow of breathable gas to a patient interface. The air delivery tube includes electric contacts associated with a heating and/or a sensing arrangement. The air delivery tube includes a locking collar rotatably movable between (1) an unlocked position to allow connection/disconnection of the air delivery tube to/from the engagement port, and (2) a locked position to releasably lock the air delivery tube to the engagement port. The air delivery tube is structured and arranged to, when the locking collar is
(Continued)

rotated into the locked position, pneumatically connect to the engagement port and define an operational configuration of the apparatus.

7 Claims, 44 Drawing Sheets

Related U.S. Application Data

(60) Provisional application No. 62/835,094, filed on Apr. 17, 2019.

(51) Int. Cl.
*A61M 16/08* (2006.01)
*A61M 16/10* (2006.01)

(52) U.S. Cl.
CPC ..... *A61M 16/1095* (2014.02); *A61M 16/0066* (2013.01); *A61M 2205/36* (2013.01)

(58) Field of Classification Search
CPC ............ A61M 16/0057; A61M 16/161; A61M 16/06; A61M 16/0683; A61M 16/024; A61M 16/0109; A61M 2205/36; A61M 2205/502; A61M 2205/3368; A61M 2205/582; A61M 2016/0027; A61M 2016/0038; F16L 37/107; F16L 37/44; F16L 37/46; F16L 37/096
See application file for complete search history.

(56) References Cited

U.S. PATENT DOCUMENTS

| | | | |
|---|---|---|---|
| 4,944,310 | A | 7/1990 | Sullivan |
| 5,259,370 | A | 11/1993 | Howe |
| 6,003,204 | A | 12/1999 | Roach et al. |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 11,839,720 | B2 * | 12/2023 | Formica .............. A61M 16/024 |
| 2003/0116989 | A1 | 6/2003 | Guanzon et al. |
| 2003/0236015 | A1 | 12/2003 | Edirisuriya |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0057438 | A1 * | 3/2011 | Auston .................... F16L 37/44 |
| | | | 285/83 |
| 2014/0137861 | A1 | 5/2014 | Feldhahn et al. |
| 2014/0216459 | A1 * | 8/2014 | Vos ........................ A61M 16/16 |
| | | | 128/204.17 |
| 2014/0246021 | A1 | 9/2014 | Buechi et al. |
| 2015/0151074 | A1 | 6/2015 | Hermez |
| 2015/0359989 | A1 | 12/2015 | Potharaju et al. |
| 2016/0008560 | A1 | 1/2016 | Kwok |
| 2016/0022954 | A1 | 1/2016 | Bath et al. |
| 2016/0228671 | A1 | 8/2016 | Jackson et al. |
| 2017/0121067 | A1 | 5/2017 | Miller et al. |
| 2017/0151411 | A1 | 6/2017 | Osborne et al. |
| 2017/0173293 | A1 | 6/2017 | Osborne et al. |
| 2017/0252531 | A1 | 9/2017 | Hensman et al. |
| 2017/0348505 | A1 | 12/2017 | Doo et al. |
| 2017/0361053 | A1 | 12/2017 | Dimatteo et al. |
| 2018/0071480 | A1 | 3/2018 | Tang et al. |
| 2018/0185606 | A1 | 7/2018 | Van Schalkwyk et al. |
| 2018/0214660 | A1 | 8/2018 | Stoks et al. |
| 2018/0333556 | A1 | 11/2018 | Ormrod et al. |
| 2019/0038865 | A1 | 2/2019 | Smith et al. |
| 2019/0321580 | A1 | 10/2019 | Kirchberger et al. |
| 2020/0155876 | A1 | 5/2020 | Appareti et al. |
| 2020/0330720 | A1 | 10/2020 | Formica et al. |

FOREIGN PATENT DOCUMENTS

| | | |
|---|---|---|
| WO | WO 98/04310 A1 | 2/1998 |
| WO | WO 98/34665 A1 | 8/1998 |
| WO | WO 00/78381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2009/127192 A1 | 10/2009 |
| WO | WO 2010/135785 A1 | 12/2010 |
| WO | WO 2012/171072 A1 | 12/2012 |
| WO | WO 2013/020167 A1 | 2/2013 |
| WO | WO 2014/138804 | 9/2014 |
| WO | WO 2015/089582 | 6/2015 |
| WO | WO 2018/094452 | 5/2018 |
| WO | WO 2019/216774 A1 | 11/2019 |

OTHER PUBLICATIONS

Formica et al., U.S. Appl. No. 16/850,047, filed Apr. 16, 2020, for "Humidification Interface Arrangements," (parent application).

* cited by examiner

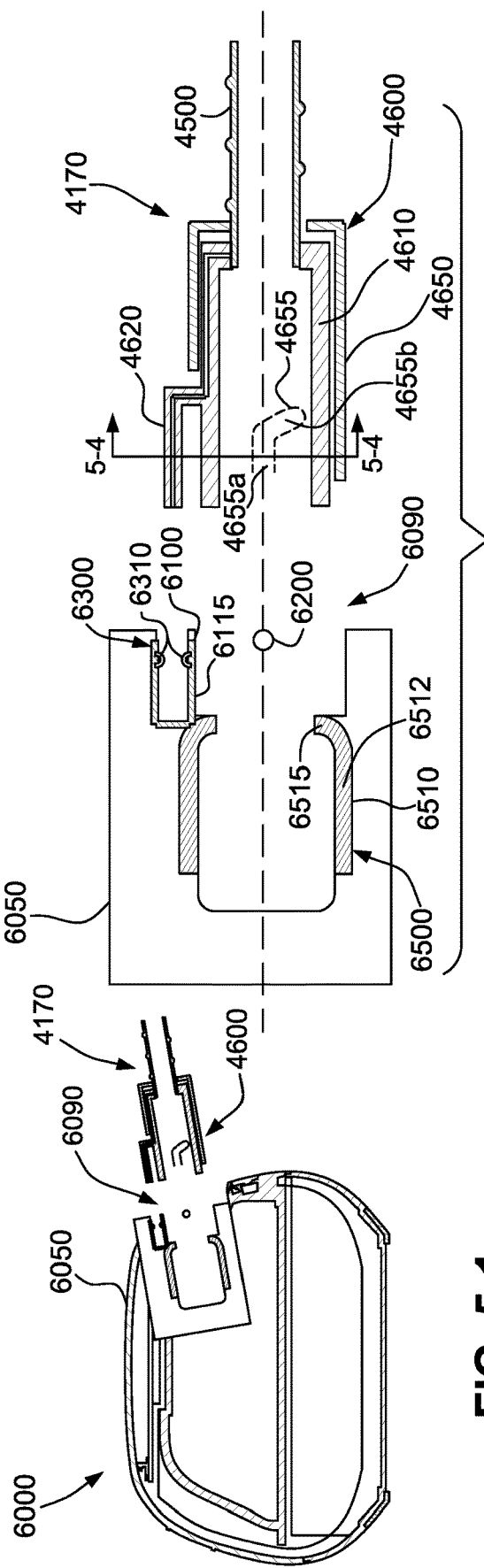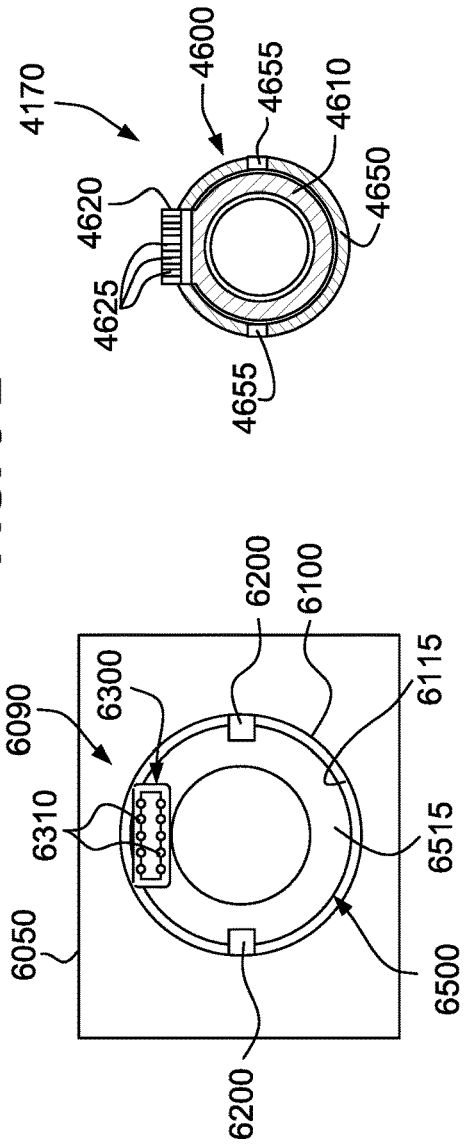
FIG. 5-1
FIG. 5-2
FIG. 5-3
FIG. 5-4

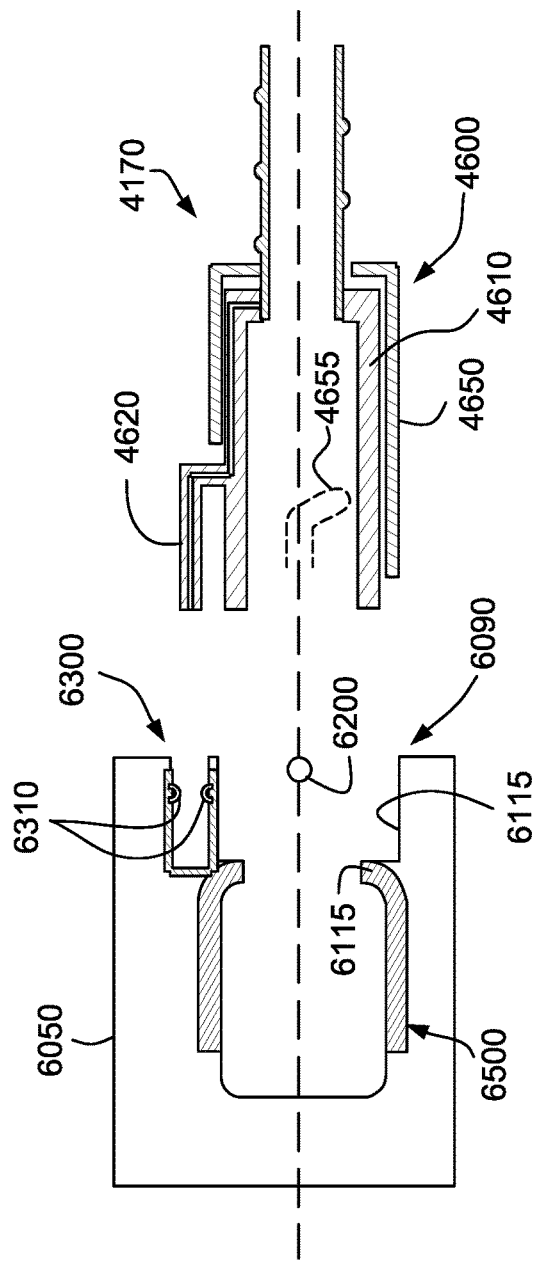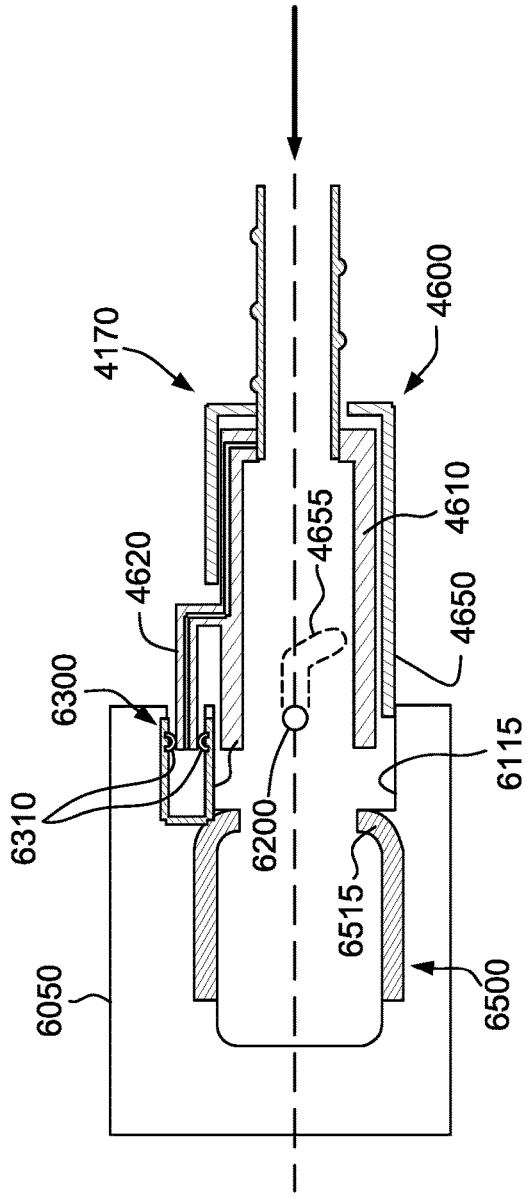

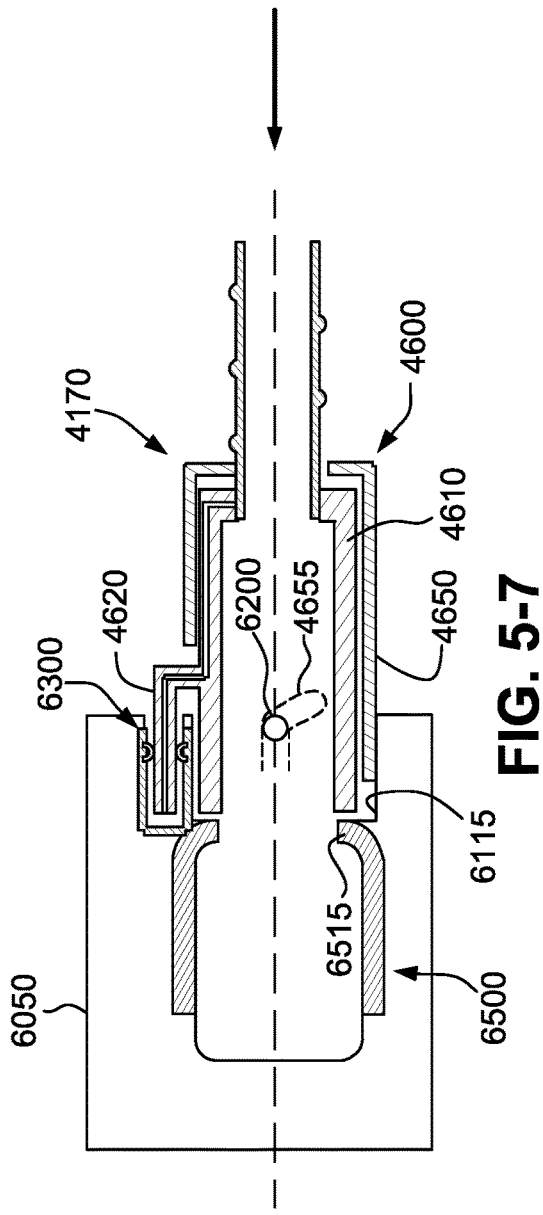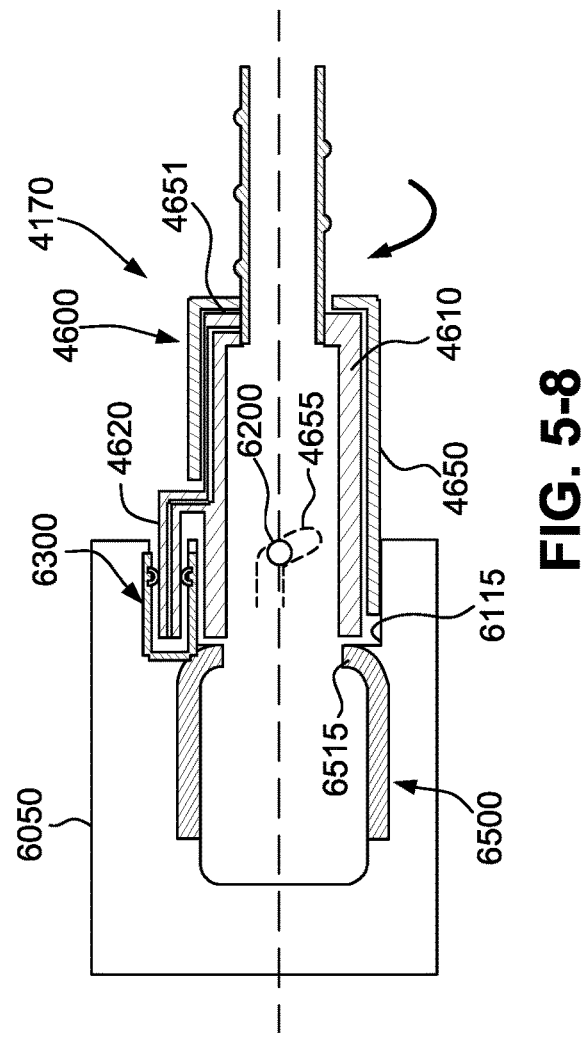

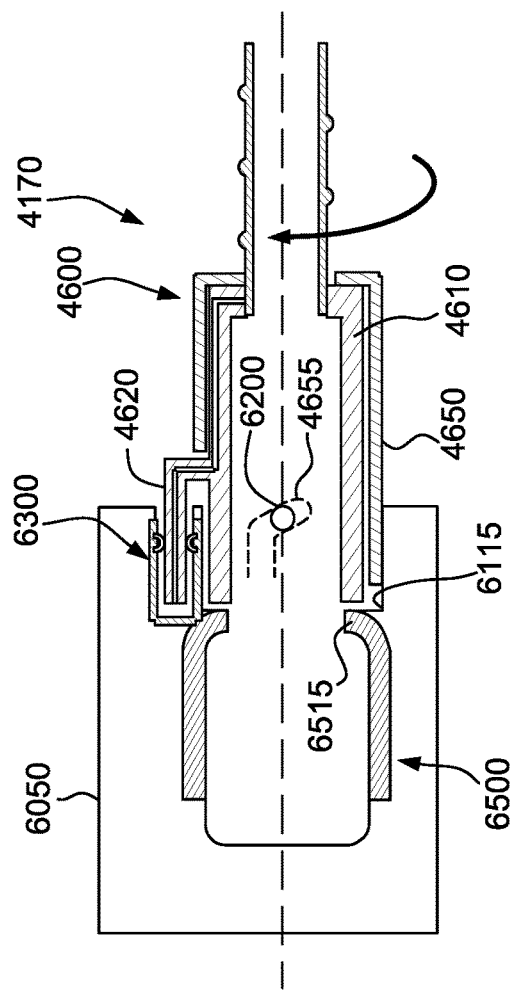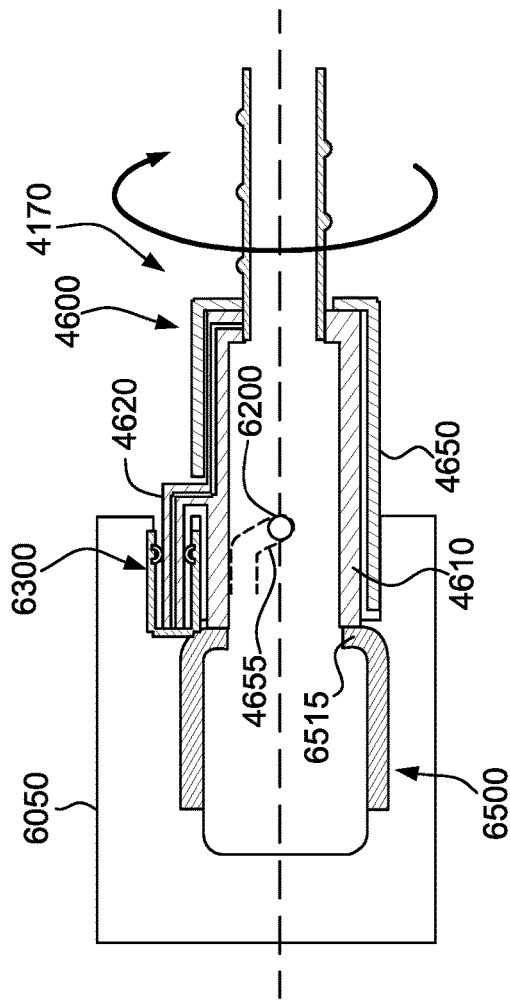

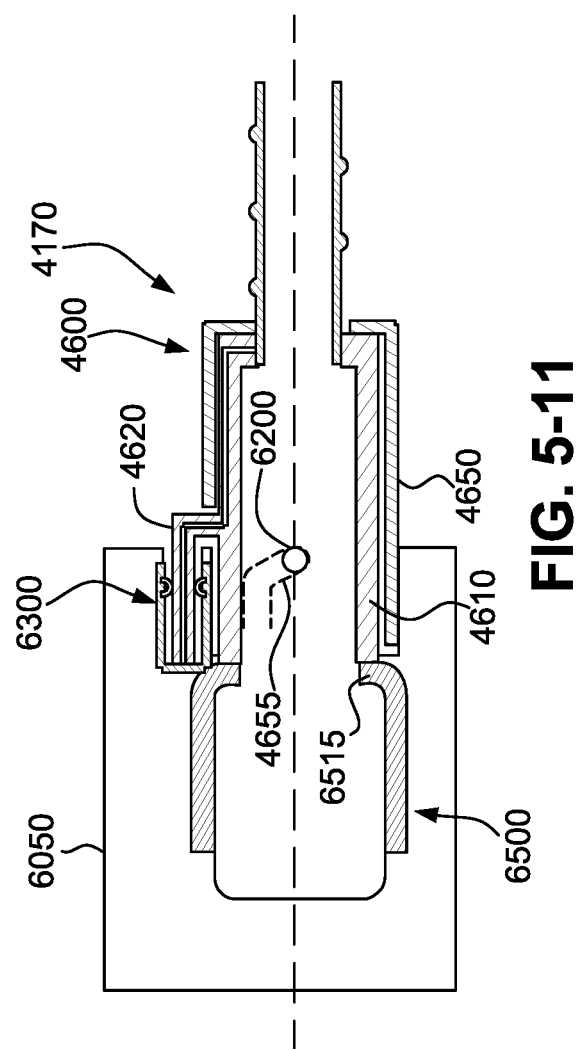

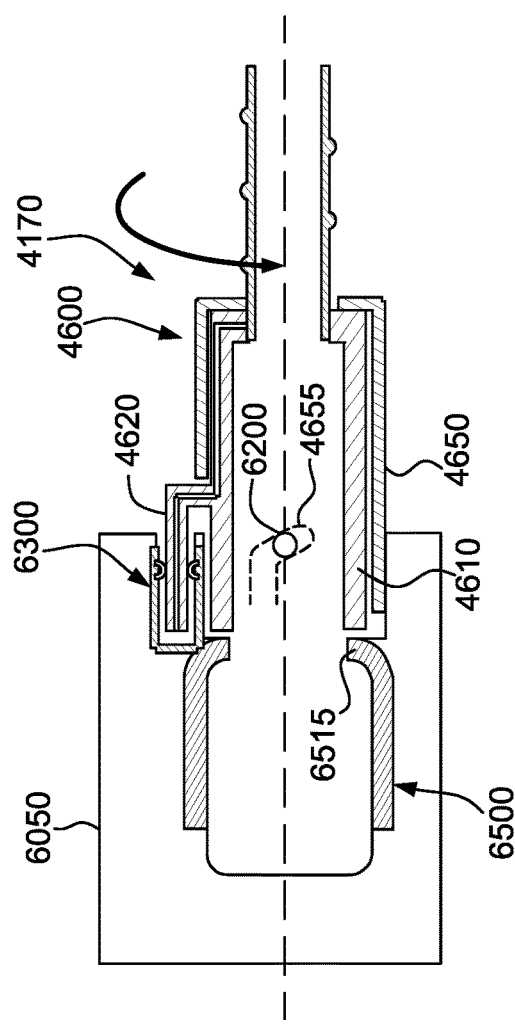
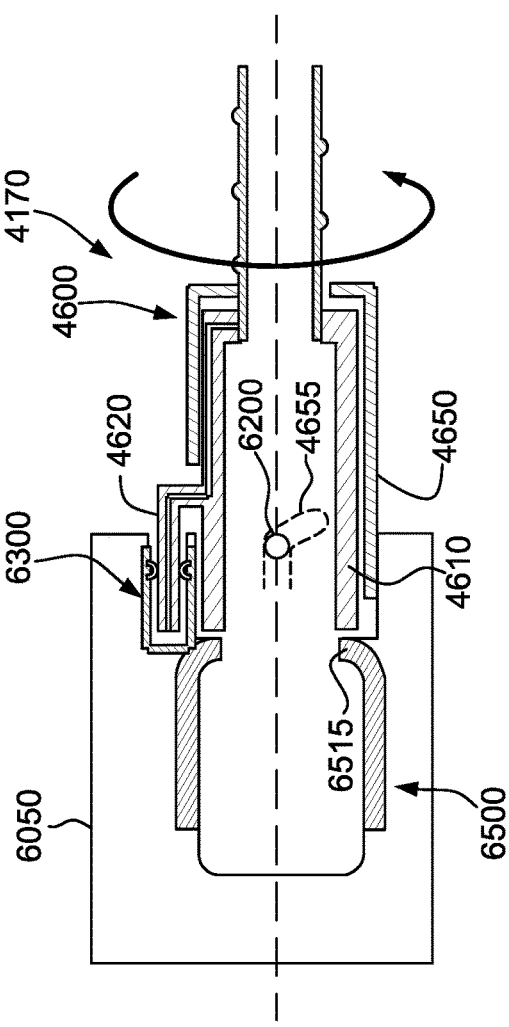
FIG. 5-16
FIG. 5-17

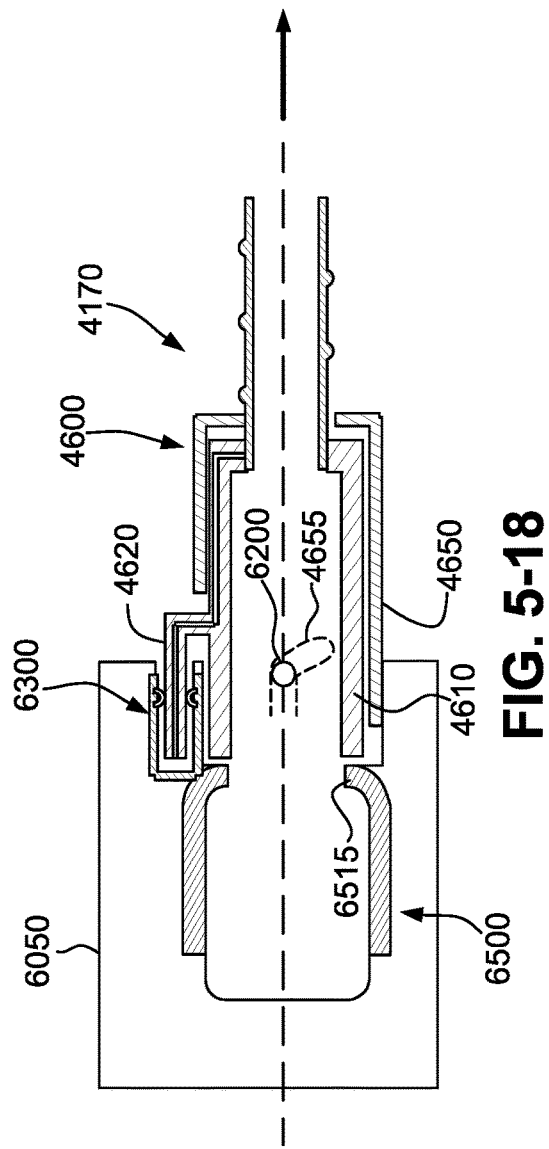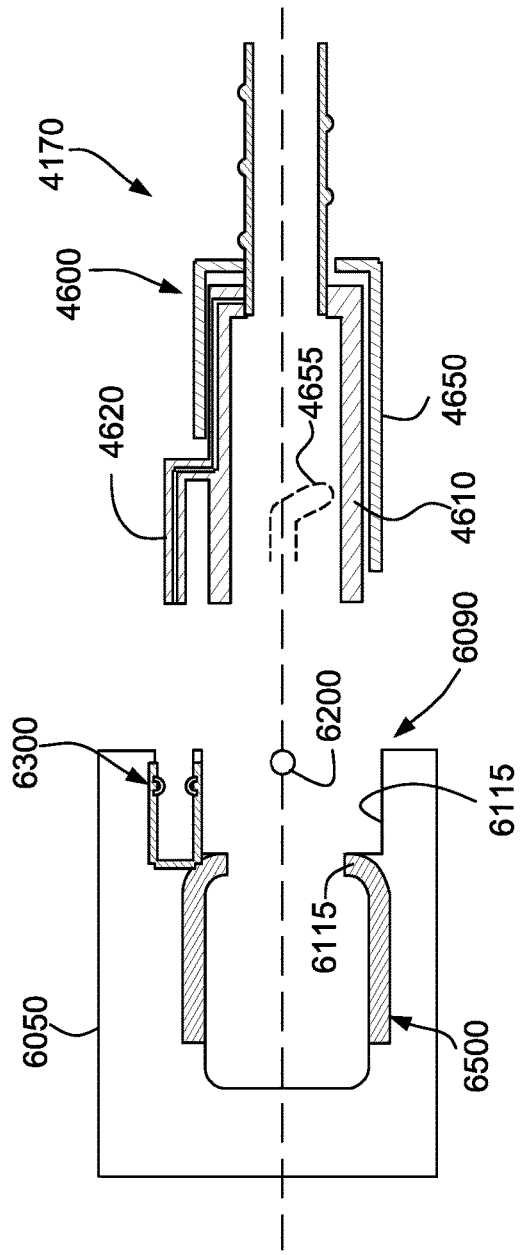

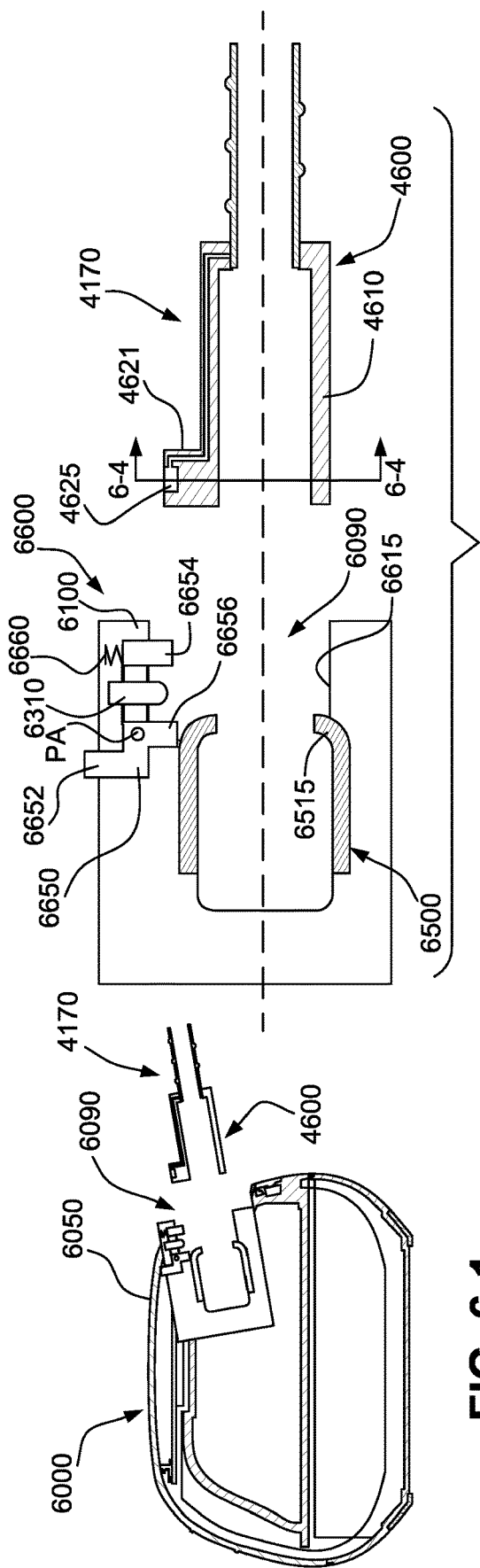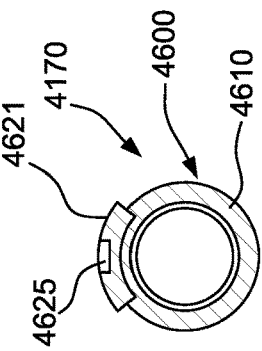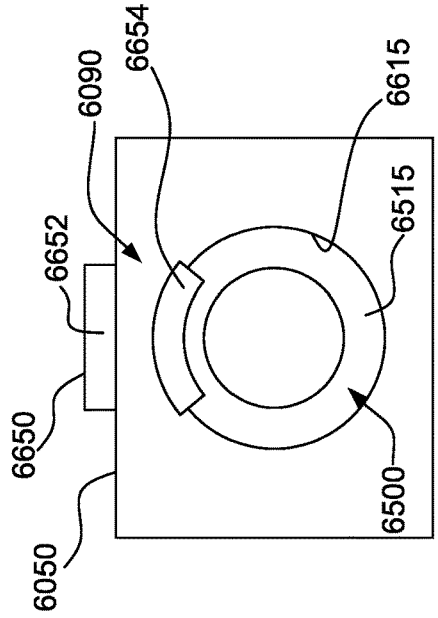

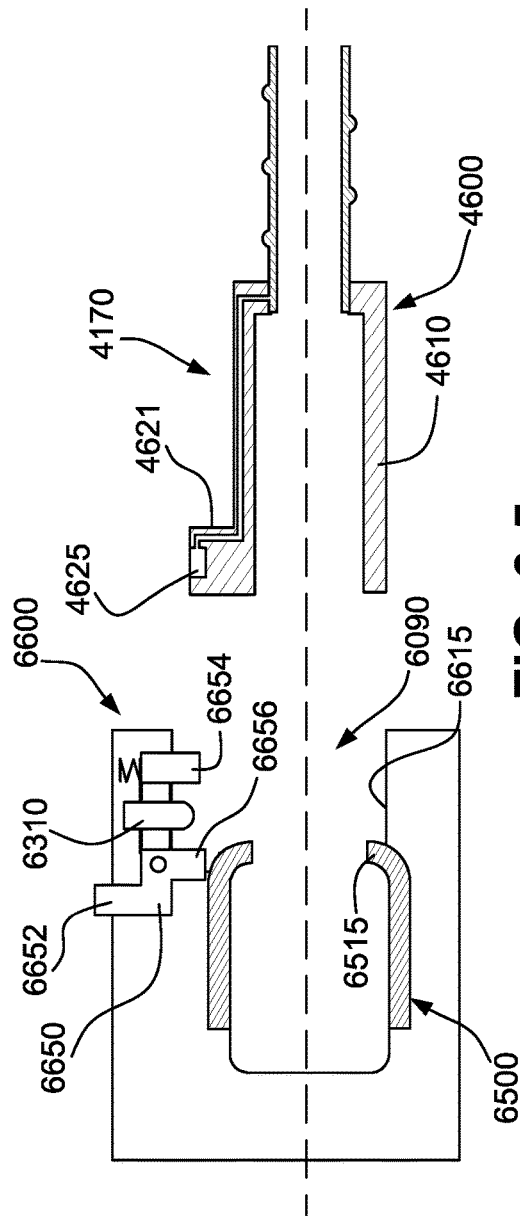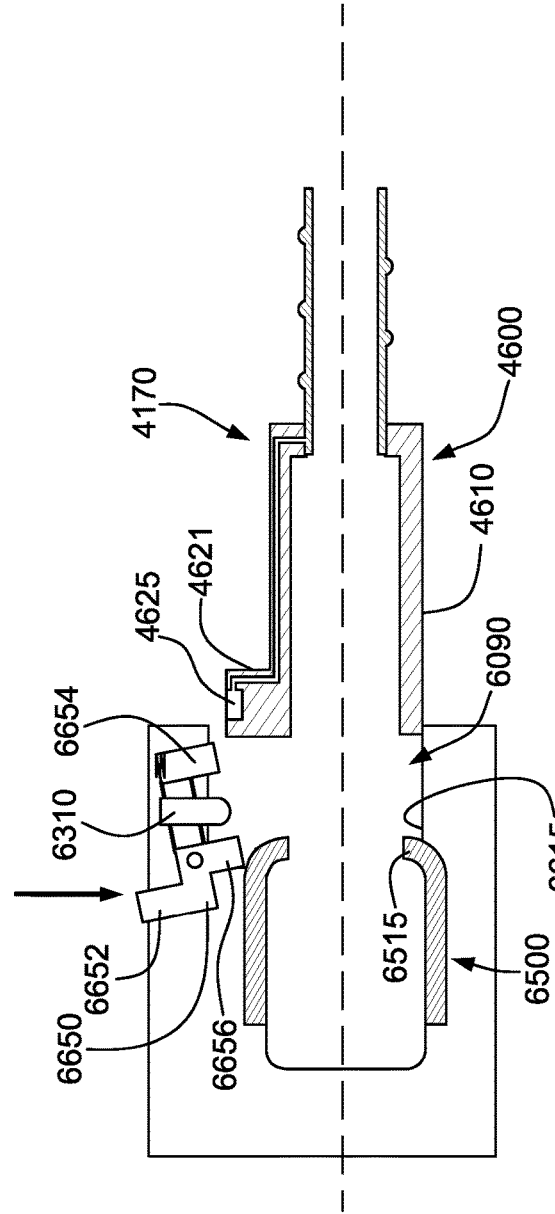

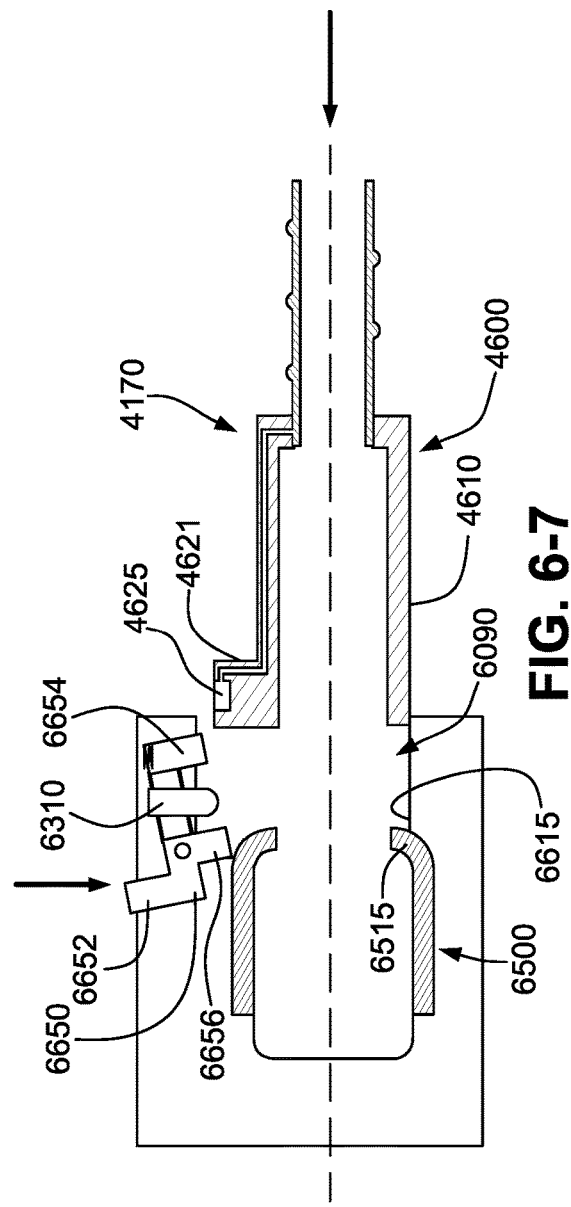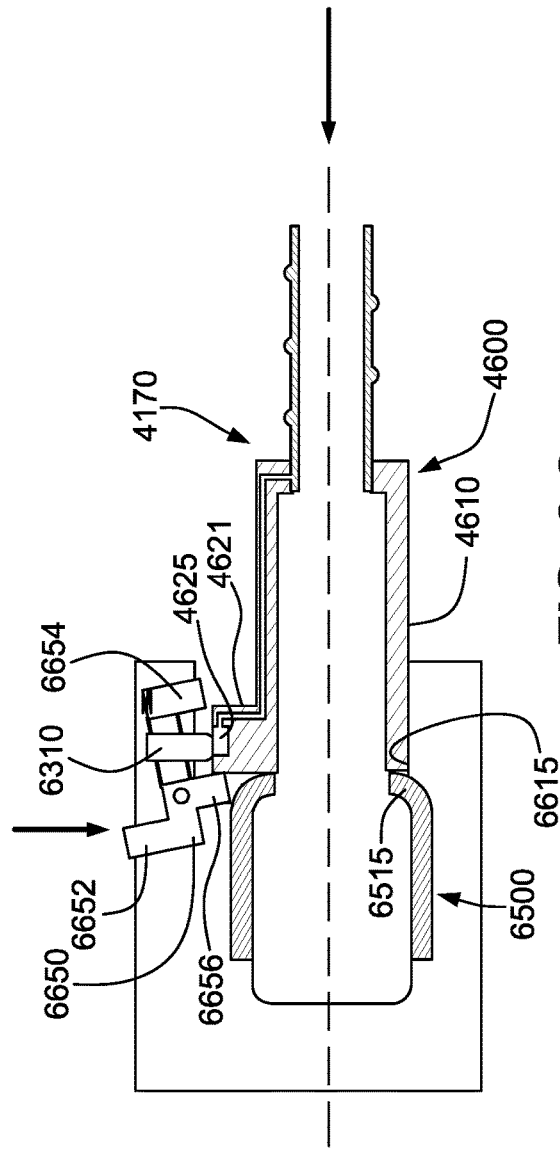

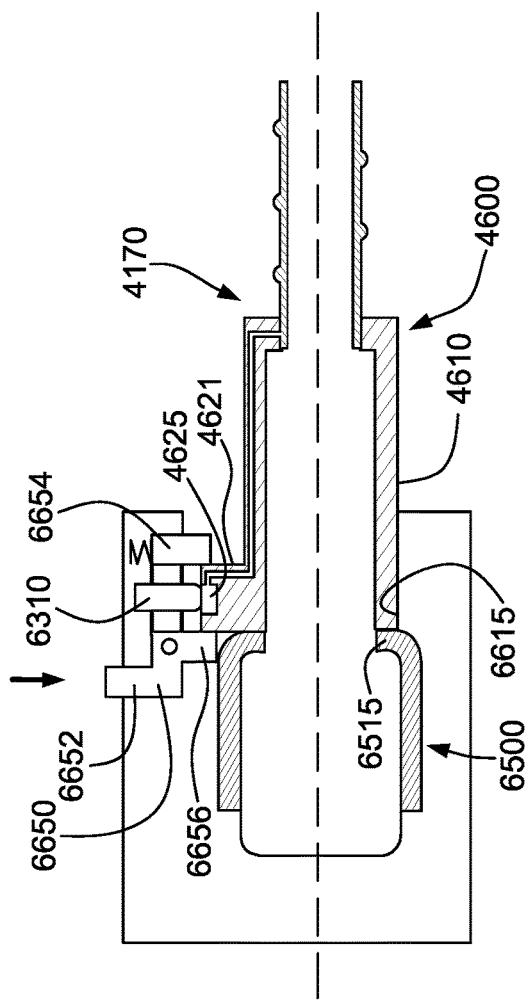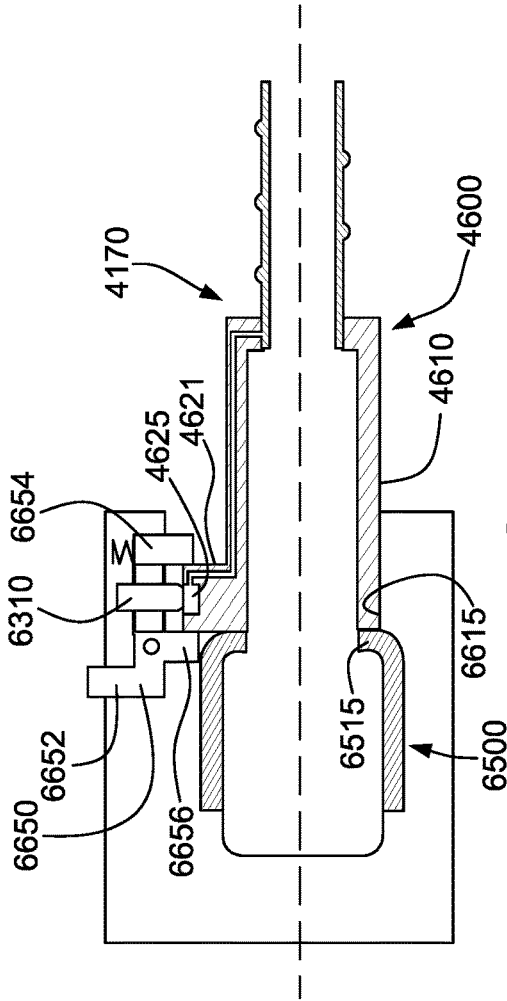

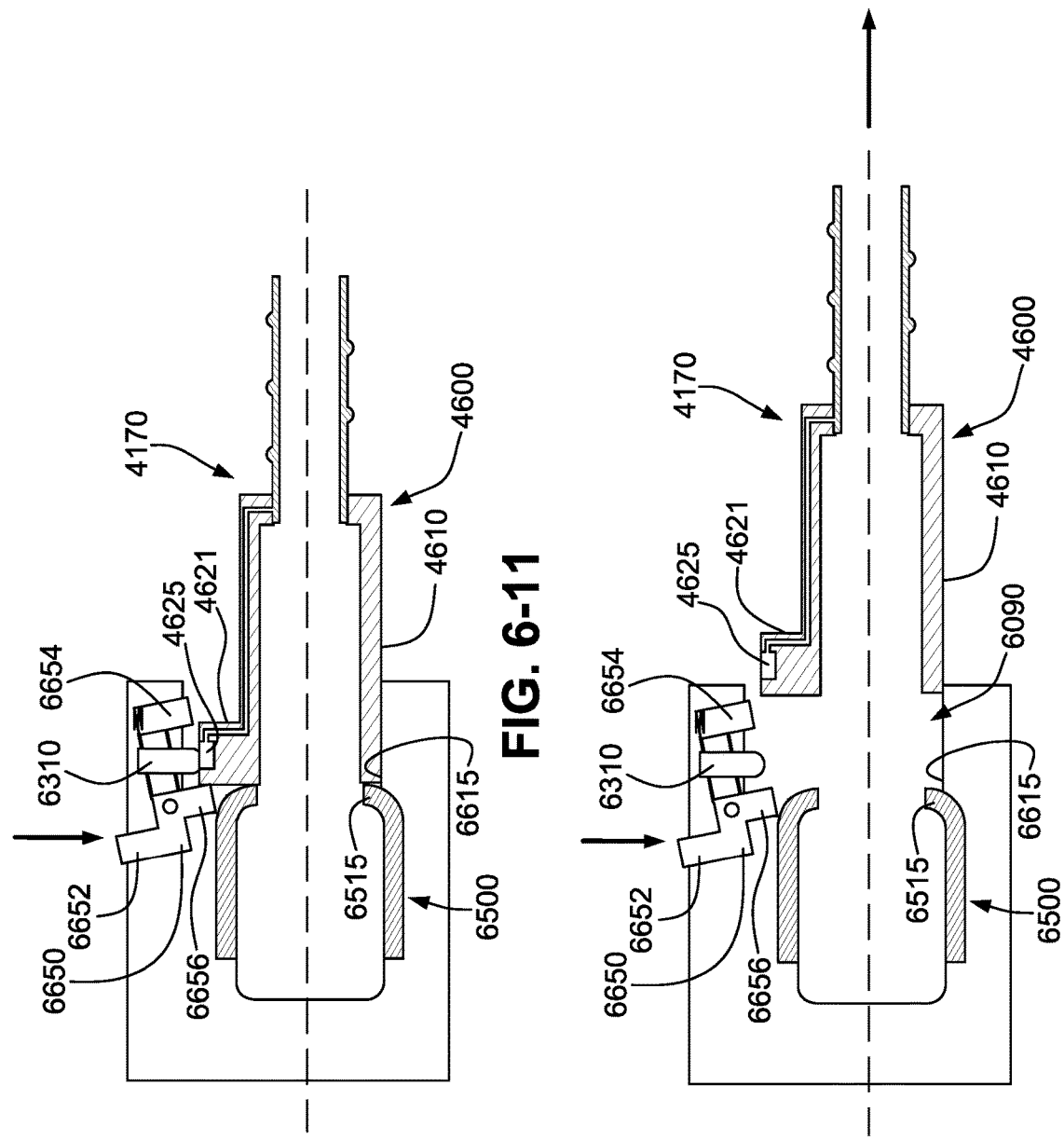

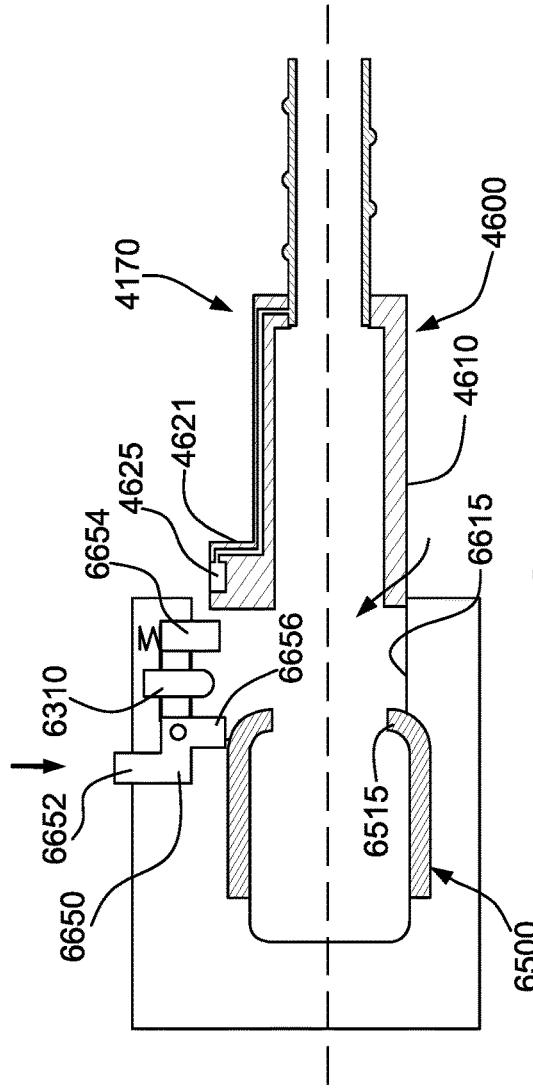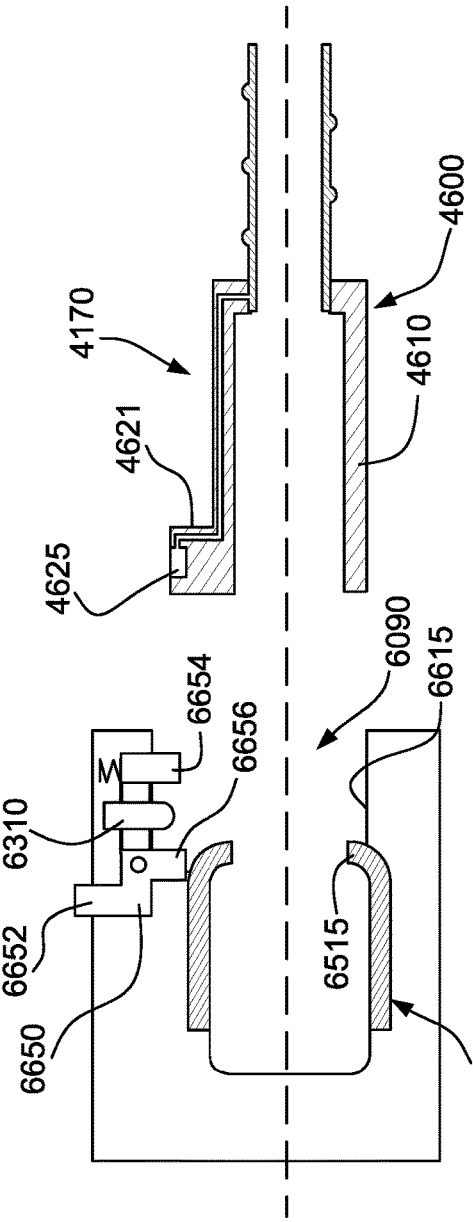

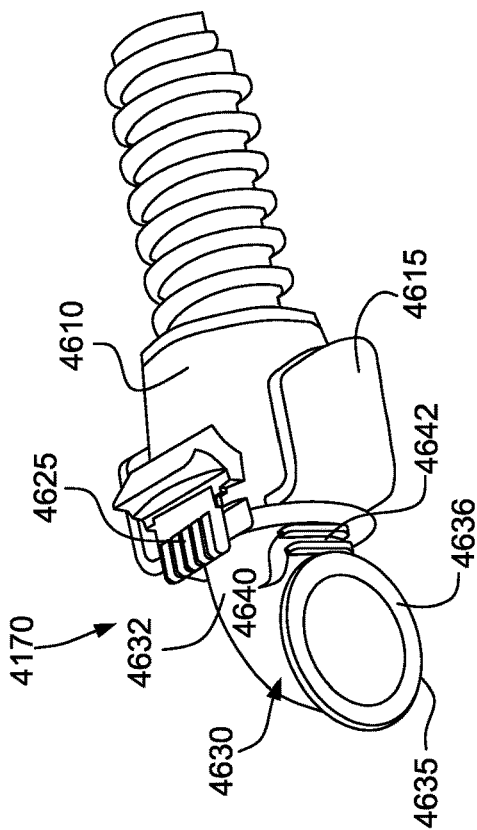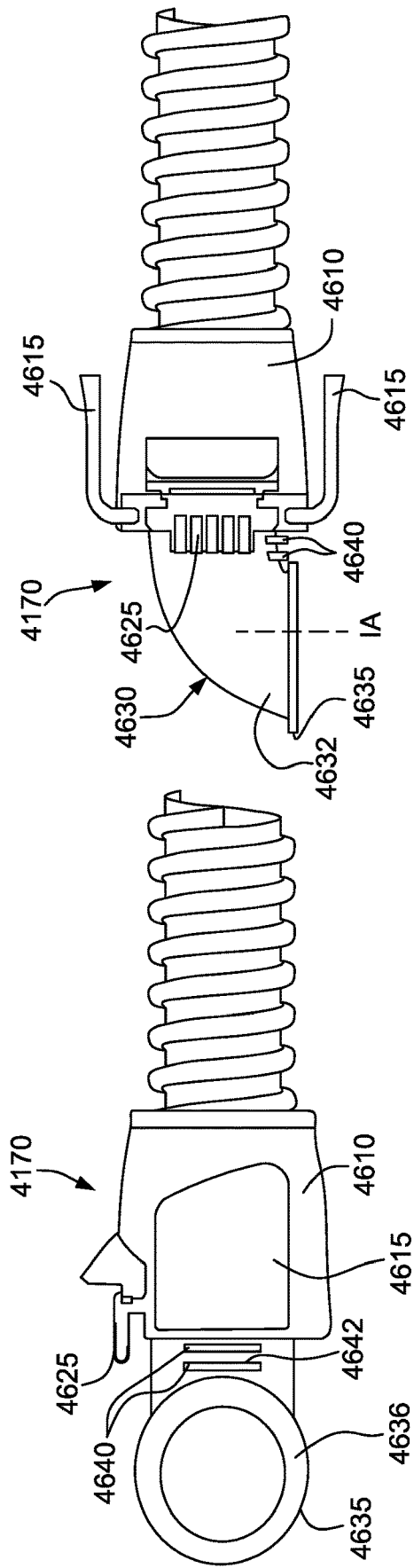
FIG. 7-1
FIG. 7-2
FIG. 7-3

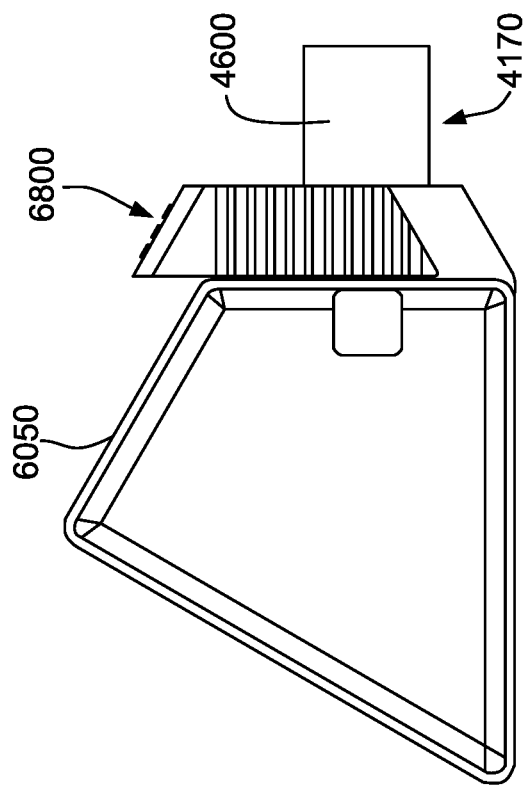
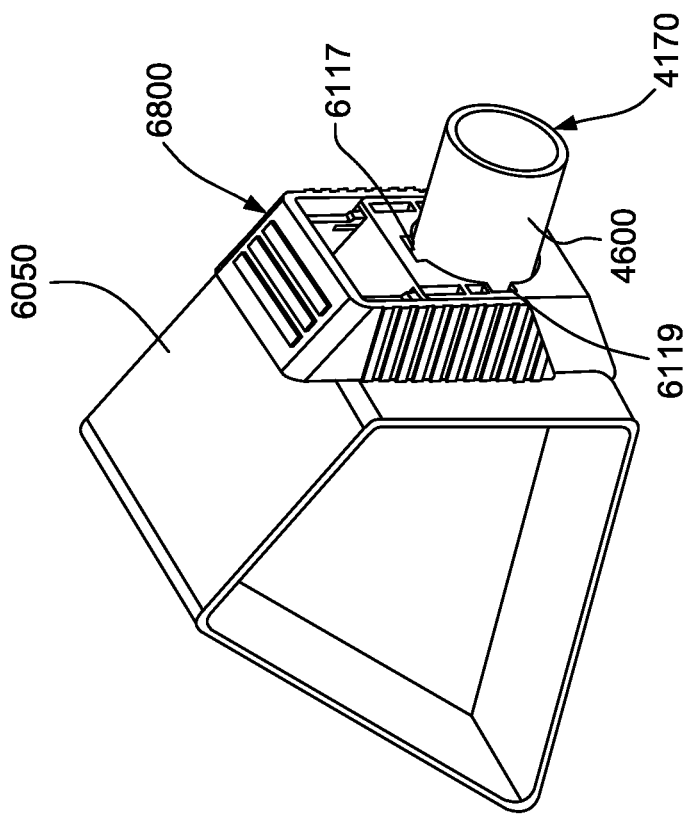

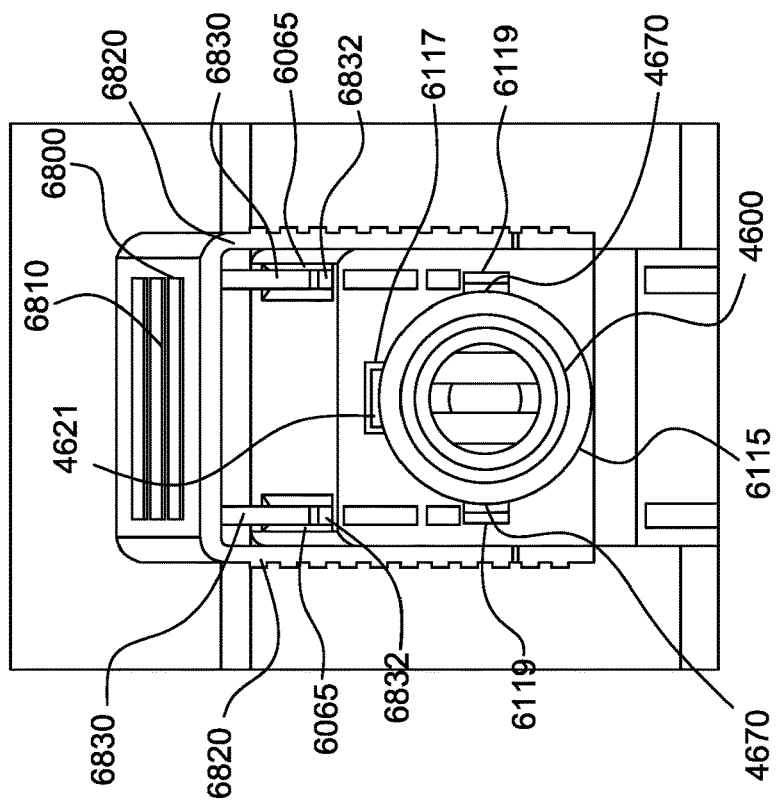
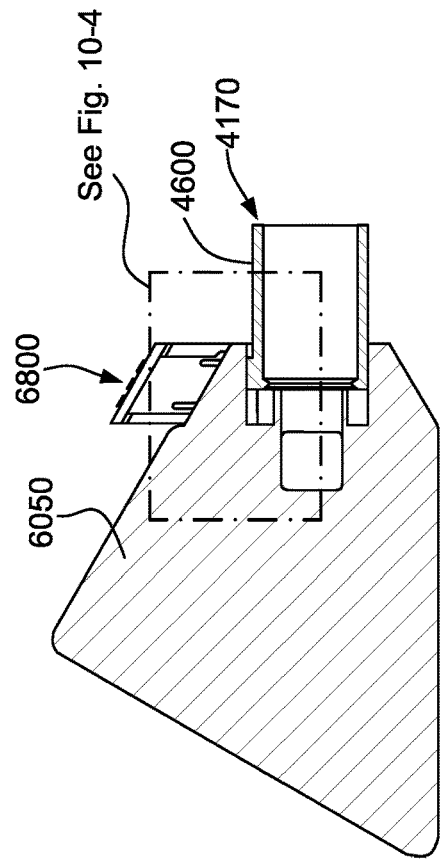
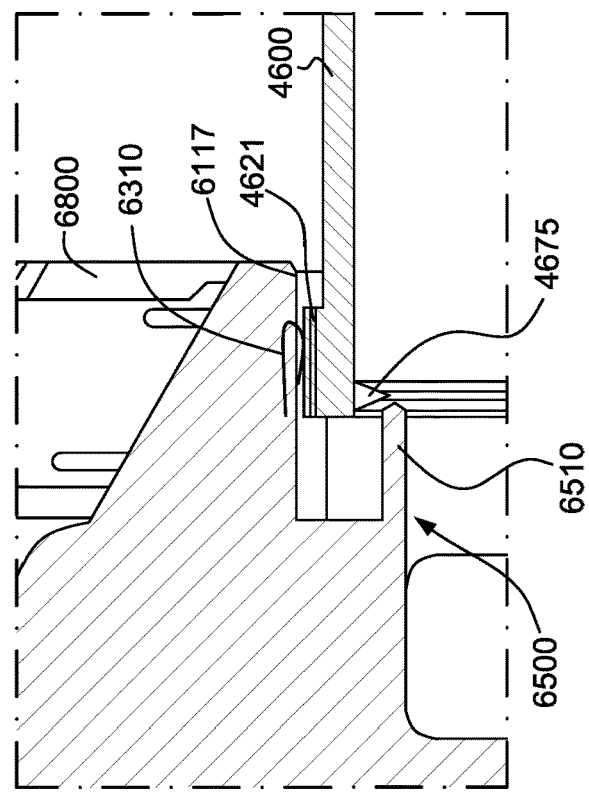
FIG. 10-5
FIG. 10-3
FIG. 10-4

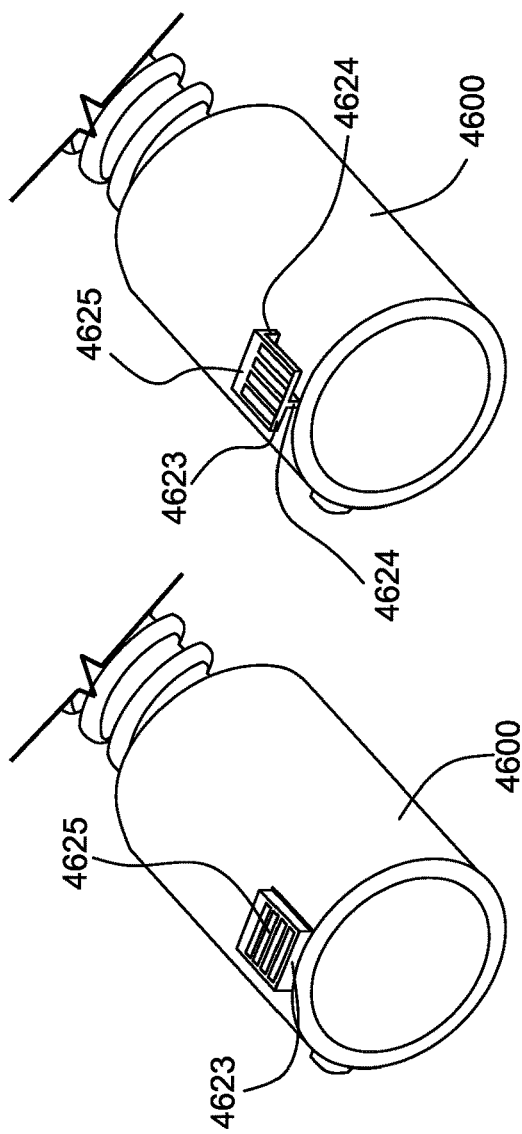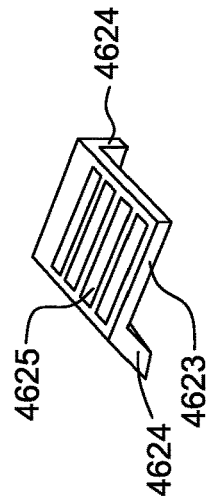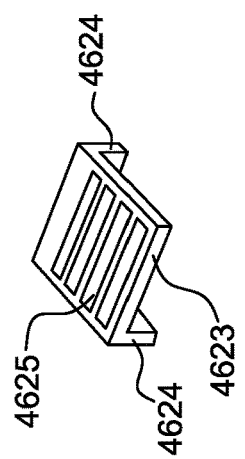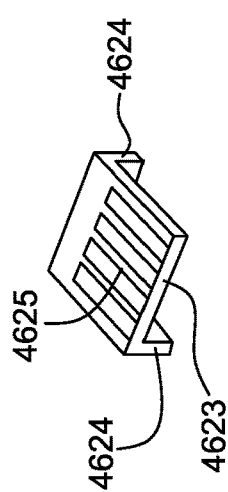

HUMIDIFICATION INTERFACE ARRANGEMENTS

1 CROSS-REFERENCE TO RELATED APPLICATIONS

This application is a continuation of U.S. application Ser. No. 16/850,047, filed Apr. 16, 2020, which claims the benefit of U.S. Provisional Application No. 62/835,094, filed Apr. 17, 2019, each of which is incorporated herein by reference in their entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention, and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways and do not take part in gas exchange. Further divisions of the airways lead to the respiratory bronchioles, and eventually to the alveoli. The alveolated region of the lung is where the gas exchange takes place and is referred to as the respiratory zone. See "Respiratory Physiology", by John B. West, Lippincott Williams & Wilkins, 9th edition published 2012.

A range of respiratory disorders exist. Certain disorders may be characterized by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and Chest wall disorders.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate, and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle-aged overweight males, although a person affected may have no awareness of the problem. See U.S. Pat. No. 4,944,310 (Sullivan).

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to the atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive, and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD, and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisee™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of the present technology relates to a CPAP system including a humidifier, a patient interface, and an air delivery tube to deliver humidified air to the patient interface. In an example, the humidifier is integrated with an RPT device structured to produce a flow of air at positive pressure.

An aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface.

An aspect of the present technology relates to an apparatus for providing a pressurised flow of breathable gas to the airways of a patient including an outlet structured and arranged to connect to an air delivery tube configured to pass the pressurised flow of breathable gas to a patient interface.

An aspect of the present technology relates to an apparatus for generating and providing a pressurised breathable gas to a patient's airways including a respiratory pressure therapy (RPT) device having an engagement dock pneumatically and electrically coupled to the RPT device and an air delivery tube configured to engage the engagement dock of the RPT device so as to pass a flow of breathable gas to a patient interface. The air delivery tube includes electric contacts associated with a heating and/or a sensing arrangement. The air delivery tube includes a locking collar rotatably movable between (1) an unlocked position to allow connection of the air delivery tube to the engagement dock and disconnection of the air delivery tube from the engagement dock, and (2) a locked position to releasably lock the air delivery tube to the engagement dock. The air delivery tube is structured and arranged to, when the locking collar is rotated into the locked position, pneumatically connect to the engagement dock and define an operational configuration of the apparatus.

An aspect of the present technology relates to an apparatus for generating and providing a pressurised breathable gas to a patient's airways including a respiratory pressure therapy (RPT) device having an engagement port pneumatically and electrically coupled to the RPT device, and an air delivery tube configured to engage the engagement port of the RPT device so as to pass a flow of breathable gas to a patient interface. The air delivery tube includes electric contacts associated with a heating and/or a sensing arrangement. The air delivery tube includes a locking collar rotatably movable between (1) an unlocked position to allow connection of the air delivery tube to the engagement port and disconnection of the air delivery tube from the engagement port, and (2) a locked position to releasably lock the air delivery tube to the engagement port. The air delivery tube is structured and arranged to, when the locking collar is rotated into the locked position, pneumatically connect to the engagement port and define an operational configuration of the apparatus.

An aspect of the present technology relates to an apparatus for generating and providing a pressurised breathable gas to a patient's airways including a respiratory pressure therapy (RPT) device having an engagement dock pneumatically and electrically coupled to the RPT device and an air delivery tube configured to engage the engagement dock of the RPT device so as to pass a flow of breathable gas to a patient interface. The air delivery tube includes electric contacts associated with a heating and/or a sensing arrangement. The engagement dock includes a locking lever pivotally movable between (1) an unlocked position to allow connection of the air delivery tube to the engagement dock and disconnection of the air delivery tube from the engagement dock, and (2) a locked position to releasably lock the air delivery tube to the engagement dock. The locking lever is structured and arranged to pneumatically connect the air delivery tube to the engagement dock when the locking lever is pivoted into the locked position.

An aspect of the present technology relates to an apparatus for generating and providing a pressurised breathable gas to a patient's airways including a respiratory pressure therapy (RPT) device having an engagement port pneumatically and electrically coupled to the RPT device and an air delivery tube configured to engage the engagement port of the RPT device so as to pass a flow of breathable gas to a patient interface. The air delivery tube includes electric contacts associated with a heating and/or a sensing arrangement. The engagement port includes a locking latch pivotally movable between (1) an unlocked position to allow connection of the air delivery tube to the engagement port and disconnection of the air delivery tube from the engagement port, and (2) a locked position to releasably lock the air delivery tube to the engagement port. The air delivery tube is pneumatically connected to the engagement port when the locking latch is pivoted into the locked position.

In an example, the RPT device comprises an engagement dock, and the engagement port forms part of the engagement dock. In an example, the engagement dock is in the form of a water reservoir dock structured and arranged to receive a water reservoir in an operative position, the water reservoir including a cavity structured to hold a volume of water, such that in an operational configuration the water reservoir is in pneumatic connection with the engagement dock and with the air delivery tube. In an example, the air delivery tube is structured and arranged to electrically connect to the engagement port when the air delivery tube is engaged with the engagement port and the locking latch is in the unlocked position. In an example, the air delivery tube is structured and arranged to form the electrical and pneumatic connections in series. In an example, the locking latch includes a stop arm to prevent the pneumatic connection when the locking latch is in the unlocked position. In an example, each of the connection and disconnection of the air delivery tube includes two independent user movements, one for the pneumatic connection/disconnections and one for the electrical connection/disconnection. In an example, the two independent user movements are in one plane or in two substantially transverse planes.

An aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The air delivery tube is structured and arranged to form a direct pneumatic connection with the water reservoir, and the air delivery tube is structured and arranged to be releasably locked to an engagement port associated with the water reservoir dock in an operative position.

In an example, the air delivery tube includes a recess configured and arranged to receive a locking protrusion protruding from the water reservoir or the engagement port. In an example, the direct pneumatic connection is dependent on the air delivery tube being connected to the water reservoir port before connection of the water reservoir to the water reservoir dock. In an example, the air delivery tube includes one or more contacts adapted to engage with contacts provided to the water reservoir port to provide an electrical connection. In an example, the air delivery tube is structured and arranged to form the electrical and pneumatic connections in series.

An aspect of the present technology relates to an apparatus for generating and providing a pressurised breathable gas to a patient's airways including a respiratory pressure therapy (RPT) device having an engagement port pneumatically and electrically coupled to the RPT device and an air delivery tube configured to engage the engagement port of the RPT device so as to pass a flow of breathable gas to a patient interface. The air delivery tube includes electric contacts associated with a heating and/or a sensing arrangement. The engagement port includes a locking latch rotatably movable between (1) an unlocked position to allow connection of the air delivery tube to the engagement port and disconnection of the air delivery tube from the engagement port, and (2) a locked position to releasably lock the air delivery tube to the engagement port. The locking latch is structured and arranged to electrically connect the air delivery tube to the engagement port when the locking latch is rotated into the locked position.

In an example, the RPT device comprises an engagement dock, and the engagement port forms part of the engagement dock. In an example, the engagement dock is in the form of a water reservoir dock structured and arranged to receive a water reservoir in an operative position, the water reservoir including a cavity structured to hold a volume of water, such that in an operational configuration the water reservoir is in a pneumatic connection with the engagement dock and with the air delivery tube. In an example, the air delivery tube is structured and arranged to pneumatically connect to the engagement port when the air delivery tube is engaged with the engagement port and the locking latch is in the unlocked position. In an example, the air delivery tube is structured and arranged to form the electrical and pneumatic connections in series. In an example, connection and disconnection of the air delivery tube includes two independent user movements. In an example, the two independent user movements are in one plane or in two substantially transverse planes.

An aspect of the present technology relates to an apparatus for generating and providing a pressurised breathable gas to a patient's airways including a respiratory pressure therapy (RPT) device having an engagement dock pneumatically and electrically coupled to the RPT device and an air delivery tube configured to engage the engagement dock of the RPT device so as to pass a flow of breathable gas to a patient interface. The air delivery tube includes electric contacts associated with a heating and/or a sensing arrangement. The engagement dock includes a locking button slidably movable between (1) an unlocked position to allow connection of the air delivery tube to the engagement dock and disconnection of the air delivery tube from the engagement dock, and (2) a locked position to releasably lock the air delivery tube to the engagement dock. The locking button is structured and arranged to pneumatically connect the air delivery tube to the engagement dock when the locking button is slid into the locked position.

An aspect of the present technology relates to an apparatus for generating and providing a pressurised breathable gas to a patient's airways including a respiratory pressure therapy (RPT) device having an engagement port pneumatically and electrically coupled to the RPT device and an air delivery tube configured to engage the engagement port of the RPT device so as to pass a flow of breathable gas to a patient interface. The air delivery tube includes electric contacts associated with a heating and/or a sensing arrangement. The engagement port includes a locking latch slidably movable between (1) an unlocked position to allow connection of the air delivery tube to the engagement port and disconnection of the air delivery tube from the engagement port, and (2) a locked position to releasably lock the air delivery tube to the engagement port. The locking latch is structured and arranged to pneumatically connect the air delivery tube to the engagement port when the locking latch is slid into the locked position.

In an example, the RPT device comprises an engagement dock, and the engagement port forms part of the engagement dock. In an example, the engagement dock is in the form of a water reservoir dock structured and arranged to receive a water reservoir in an operative position, the water reservoir including a cavity structured to hold a volume of water, such that in an operational configuration the water reservoir is in pneumatic connection with the engagement port and with the air delivery tube. In an example, the air delivery tube is structured and arranged to electrically connect to the engagement port when the locking latch is in the unlocked position. In an example, the air delivery tube is structured and arranged to form the electrical and pneumatic connections in series. In an example, the locking latch includes a guide slot structured and arranged to receive a locking pin provided to the air delivery tube. In an example, connection and disconnection of the air delivery tube includes two independent user movements. In an example, the two independent user movements are along two substantially transverse directions. In an example, the locking latch includes a retaining protrusion configured and arranged to releasably retain the locking latch in each of the unlocked and locked positions.

An aspect of the present technology relates to an apparatus for generating and providing a pressurised breathable gas to a patient's airways including a respiratory pressure therapy (RPT) device having an engagement dock pneumatically and electrically coupled to the RPT device, an air delivery tube configured to engage the engagement dock of the RPT device so as to pass a flow of breathable gas to a patient interface, the air delivery tube including electric contacts associated with a heating and/or a sensing arrangement, and an intermediate component removably coupled to the engagement dock. The intermediate component is configured to pneumatically connect the air delivery tube to the engagement dock, electrically connect the air delivery tube to the engagement dock, and mechanically connect the air delivery tube to the engagement dock.

An aspect of the present technology relates to an apparatus for generating and providing a pressurised breathable gas to a patient's airways including a respiratory pressure therapy (RPT) device having an engagement port pneumatically and electrically coupled to the RPT device and an air delivery tube configured to engage the engagement port of the RPT device so as to pass a flow of breathable gas to a patient interface. The air delivery tube includes electric contacts associated with a heating and/or a sensing arrangement. The engagement port comprises an intermediate component removably coupled to the engagement port. The intermediate component is configured to pneumatically connect the air delivery tube to the RPT device, and electrically and mechanically connect the air delivery tube to the engagement port.

In an example, the RPT device comprises an engagement dock, and the engagement port forms part of the engagement dock. In an example, the engagement dock is in the form of a water reservoir dock structured and arranged to receive a water reservoir in an operative position, the water reservoir including a cavity structured to hold a volume of water, such that in an operational configuration the water reservoir is in pneumatic connection with the intermediate component and with the air delivery tube. In an example, the intermediate component is structured and arranged to form the pneumatic, electrical, and mechanical connections substantially simultaneously.

An aspect of the present technology relates to an apparatus for generating and providing a pressurised breathable gas to a patient's airways including a respiratory pressure therapy (RPT) device having an engagement port pneumatically and electrically coupled to the RPT device and an air delivery tube configured to engage the engagement port of the RPT device so as to pass a flow of breathable gas to a patient interface. The air delivery tube includes electric contacts associated with a heating and/or a sensing arrangement. The engagement port includes an actuator moveable between a non-actuated position and an actuated position. At least one of a pneumatic connection, a mechanical connection, and an electrical connection is effected when the actuator is in the non-actuate position, and at least one further of the pneumatic connection, mechanical connection, and electrical connection is effected when the actuator is in the actuated position.

In an example, the actuator comprises a pivotally movable latch. In an example, the actuator comprises a slidably moveable latch. In an example, the actuator releasably locks the air delivery tube to the engagement port in the actuated position. In an example, the air delivery tube pneumatically connects to the engagement port when the actuator is in the actuated position. In an example, the air delivery tube electrically connects to the engagement port when the actuator is in the non-actuated position. In an example, the engagement port includes a removable intermediate component arranged for effecting the pneumatic connection.

An aspect of the present technology relates to an apparatus for generating and providing a pressurised breathable gas to a patient's airways including a respiratory pressure therapy (RPT) device having an engagement port pneumatically and electrically coupled to the RPT device and an air delivery tube configured to engage the engagement port of the RPT device so as to pass a flow of breathable gas to a patient interface. The air delivery tube includes electric contacts associated with a heating and/or a sensing arrangement. The air delivery tube includes a contact support structure to support the electric contacts in an elevated position.

An aspect of the present technology relates to an air delivery tube configured to pass a pressurised flow of breathable gas to a patient interface.

An aspect of the present technology relates to a CPAP system including a humidifier, an air delivery tube to deliver humidified air to a patient interface, and an interface arrangement between the humidifier and the air delivery tube. In an example, the humidifier is integrated with an RPT device structured to produce a flow of air at positive pressure.

An aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The air delivery tube includes a locking collar rotatably movable between (1) an unlocked position to allow connection of the air delivery tube to the water reservoir dock and disconnection of the air delivery tube from the water reservoir dock, and (2) a locked position to releasably lock the air delivery tube to the water reservoir dock in an operative position. The air delivery tube is structured and arranged to pneumatically connect to the water reservoir dock when the locking collar is rotated into the locked position.

An aspect of the present technology relates to an air delivery tube including a locking collar rotatably movable between (1) an unlocked position to allow connection of the air delivery tube to an apparatus and disconnection of the air delivery tube from the apparatus, and (2) a locked position to releasably lock the air delivery tube to the apparatus in an operative position. In an example, the air delivery tube is structured and arranged to pneumatically connect to the apparatus when the locking collar is rotated into the locked position.

An aspect of the present technology relates to an apparatus for humidifying a flow of breathable gas including a water reservoir including a cavity structured to hold a volume of water, a water reservoir dock structured and arranged to receive the water reservoir in an operative position, and a locking member to releasably lock an air delivery tube to the water reservoir dock in an operative position.

An aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The water reservoir dock includes a locking lever pivotally movable between (1) an unlocked position to allow connection of the air delivery tube to the water reservoir dock and disconnection of the air delivery tube from the water reservoir dock, and (2) a locked position to releasably lock the air delivery tube to the water reservoir dock in an operative position. The locking lever is structured and arranged to pneumatically connect the air delivery tube to the water reservoir dock when the locking lever is pivoted into the locked position.

An aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The air delivery tube is structured and arranged to form a direct pneumatic connection with the water reservoir, and the air delivery tube is structured and arranged to interface with the water reservoir to releasably lock the air delivery tube to the water reservoir dock in an operative position.

An aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The water reservoir dock includes a locking latch rotatably movable between (1) an unlocked position to allow connection of the air delivery tube to the water reservoir dock and disconnection of the air delivery tube from the water reservoir dock, and (2) a locked position to releasably lock the air delivery tube to the water reservoir dock in an operative position. The locking latch is structured and arranged to electrically connect the air delivery tube to the water reservoir dock when the locking latch is rotated into the locked position.

An aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The water reservoir dock includes a locking button slidably movable between (1) an unlocked position to allow connection of the air delivery tube to the water reservoir dock and disconnection of the air delivery tube from the water reservoir dock, and (2) a locked position to releasably lock the air delivery tube to the water reservoir dock in an operative position. The locking button is structured and arranged to pneumatically connect the air delivery tube to the water reservoir dock when the locking button is slid into the locked position.

An aspect of the present technology relates to an apparatus for humidifying a flow of breathable gas including a water reservoir including a cavity structured to hold a volume of water, a water reservoir dock structured and arranged to receive the water reservoir in an operative position, an air delivery tube configured to pass the flow of breathable gas that has been humidified in the water reservoir to a patient interface, and an intermediate component removably coupled to the water reservoir dock. The intermediate component is configured to pneumatically connect the air delivery tube to the water reservoir, electrically connect the air delivery tube to the water reservoir dock, and mechanically connect the air delivery tube to the water reservoir dock.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

4.2 Patient Interface

FIG. 2 shows a patient interface in the form of a nasal mask in accordance with one form of the present technology.

4.3 RPT Device and Humidifier

FIG. 5-1 is a cross-sectional view showing an integrated RPT device and humidifier and an air delivery tube including an interface arrangement according to an example of the present technology.

FIG. 5-2 is a cross-sectional view showing the interface arrangement of FIG. 5-1.

FIG. 5-3 is a front view (transverse to the view in FIG. 5-2) showing an interface at the dock outlet of integrated RPT device and humidifier according to an example of the present technology.

FIG. 5-4 is a cross-sectional view (along line 5-4-5-4 and transverse to the view in FIG. 5-2) showing an interface at the dock connector of the air delivery tube according to an example of the present technology.

FIGS. 5-5 to 5-11 are cross-sectional views similar to the cross-sectional view of FIG. 5-2 and showing sequential stages of the connection of the dock connector of the air delivery tube to the dock outlet of the integrated RPT device and humidifier according to an example of the present technology.

FIG. 5-12 is a top view of the dock connector of the air delivery tube showing the locking collar in an unlocked position according to an example of the present technology.

FIG. 5-13 is a top view of the dock connector of the air delivery tube showing the locking collar in a locked position according to an example of the present technology.

FIG. 5-14 is a schematic view showing a locking feature for the locking collar of the air delivery tube according to an example of the present technology.

Figure 2:
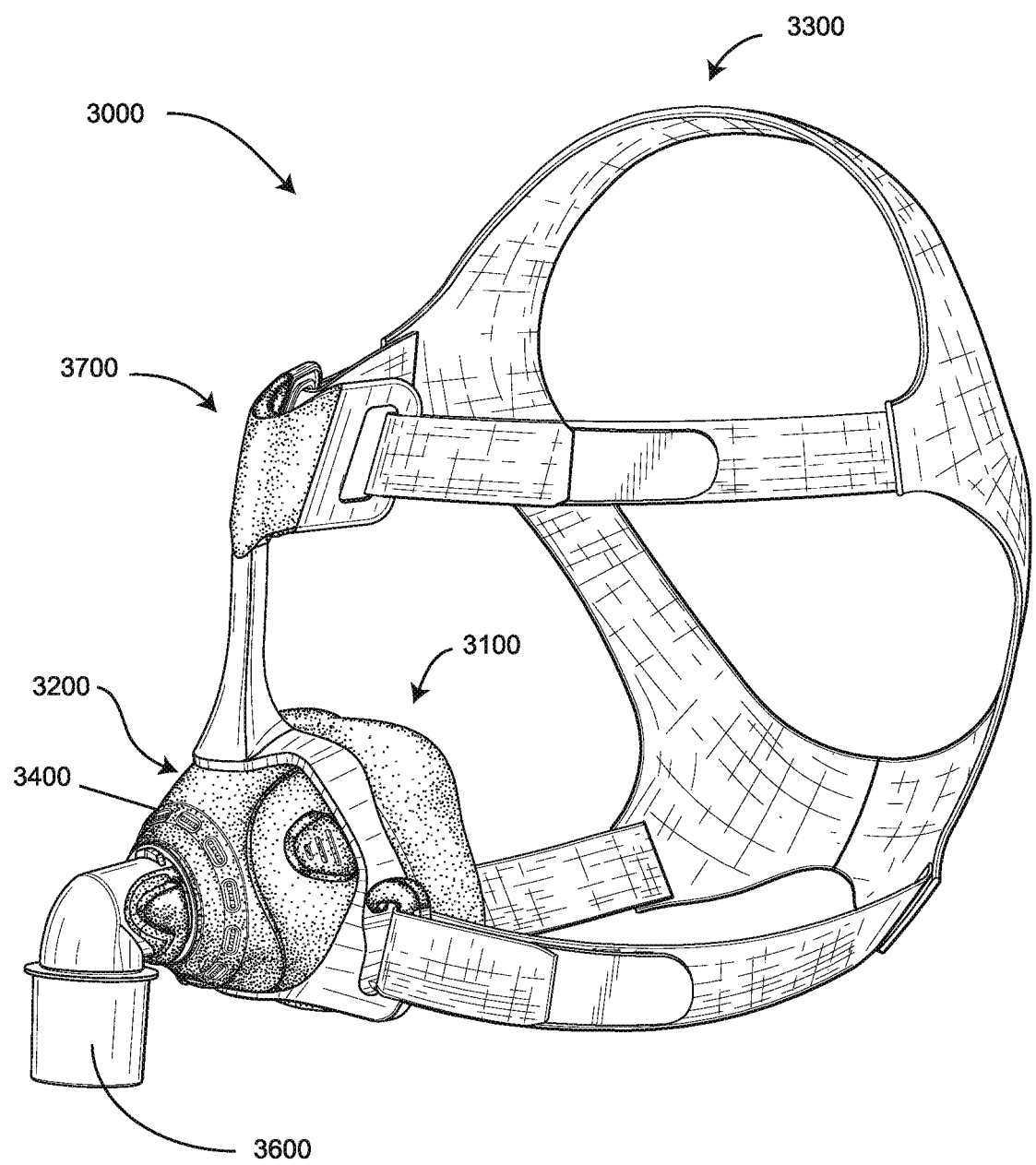
Figures 5, 6, 7, 8, 9, 10, 11, 12:
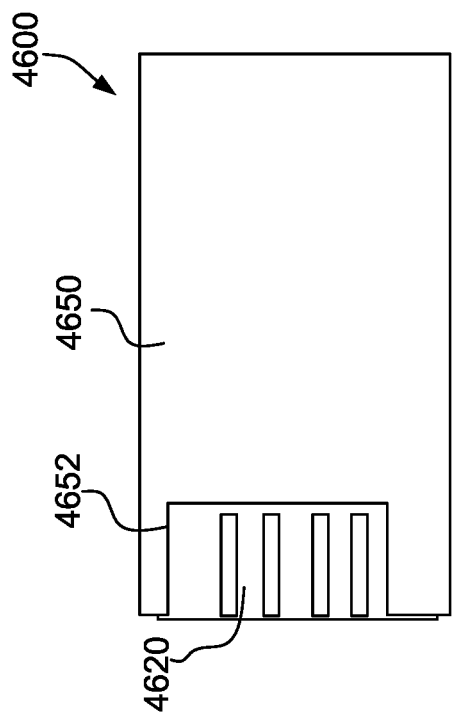

FIG. 5-15 is a schematic view showing a locking feature for the locking collar of the air delivery tube according to another example of the present technology FIGS. 5-16 to 5-19 are cross-sectional views similar to the cross-sectional view of FIG. 5-2 and showing sequential stages of the disconnection of the dock connector of the air delivery tube from the dock outlet of the integrated RPT device and humidifier according to an example of the present technology.

Figure 1:
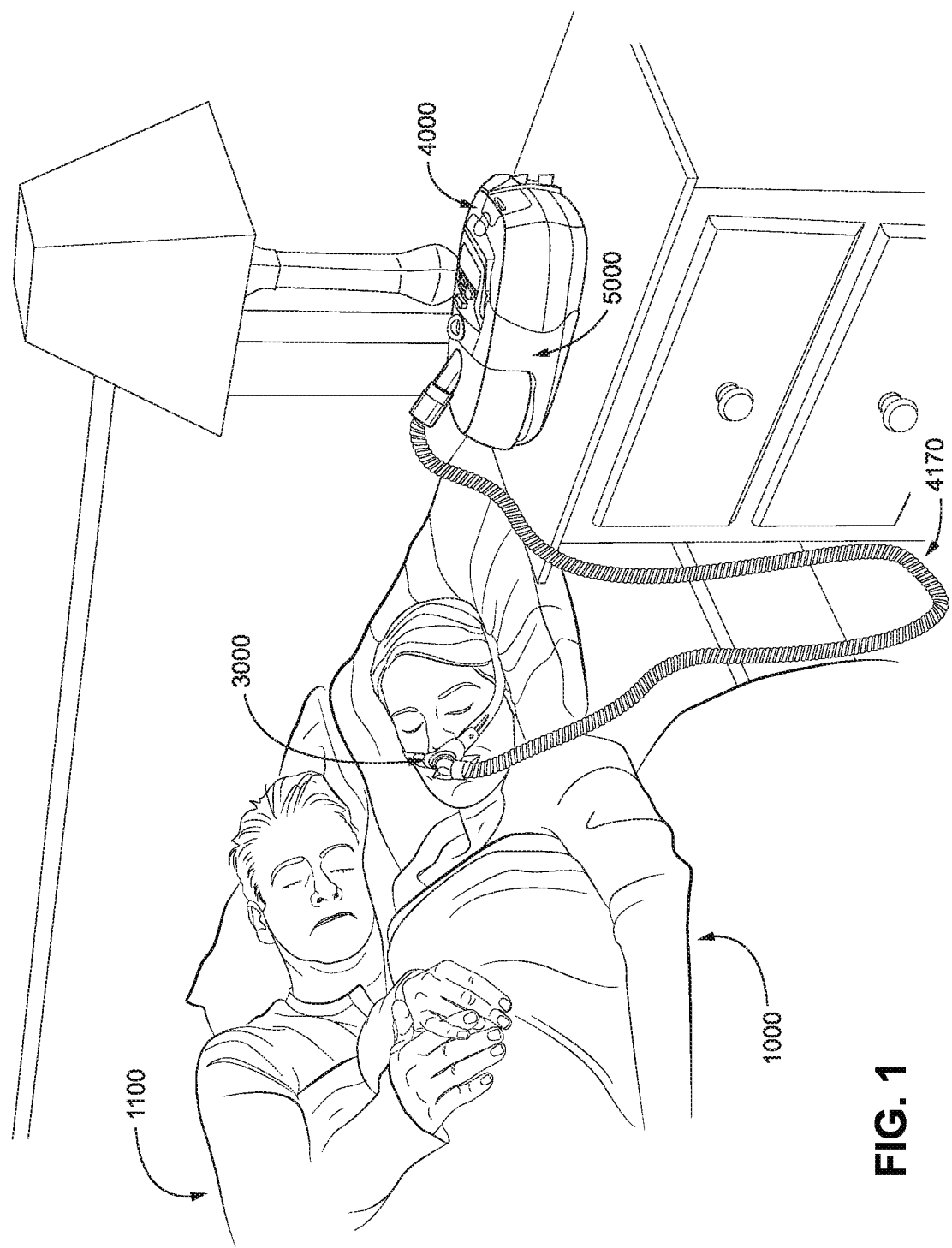

FIG. 6-1 is a cross-sectional view showing an integrated RPT device and humidifier and an air delivery tube including an interface arrangement according to another example of the present technology.

FIG. 6-2 is a cross-sectional view showing the interface arrangement of FIG. 6-1.

Figures 2, 8:
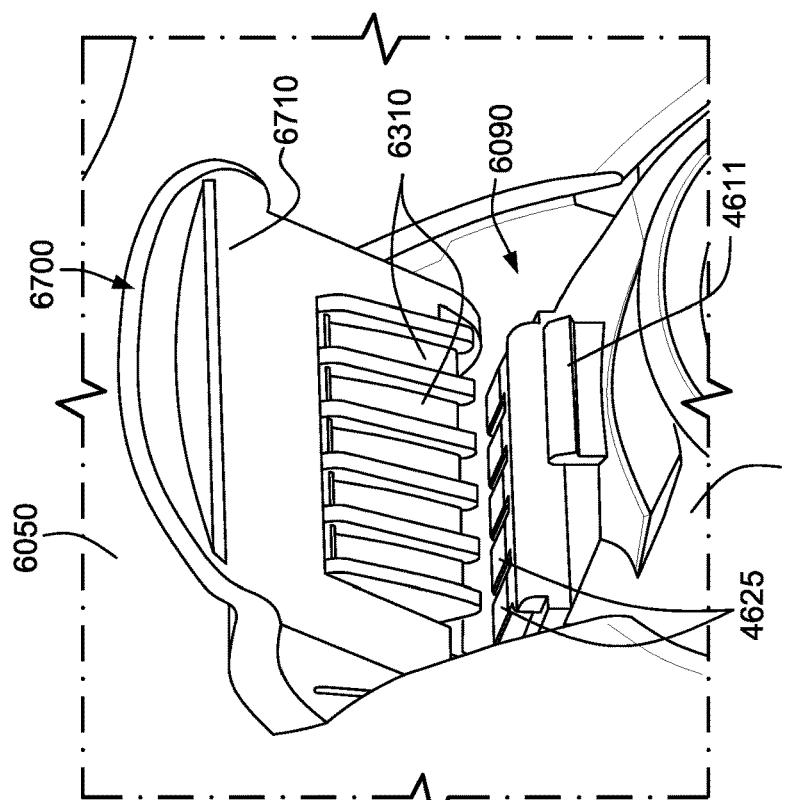
Figures 1, 8:
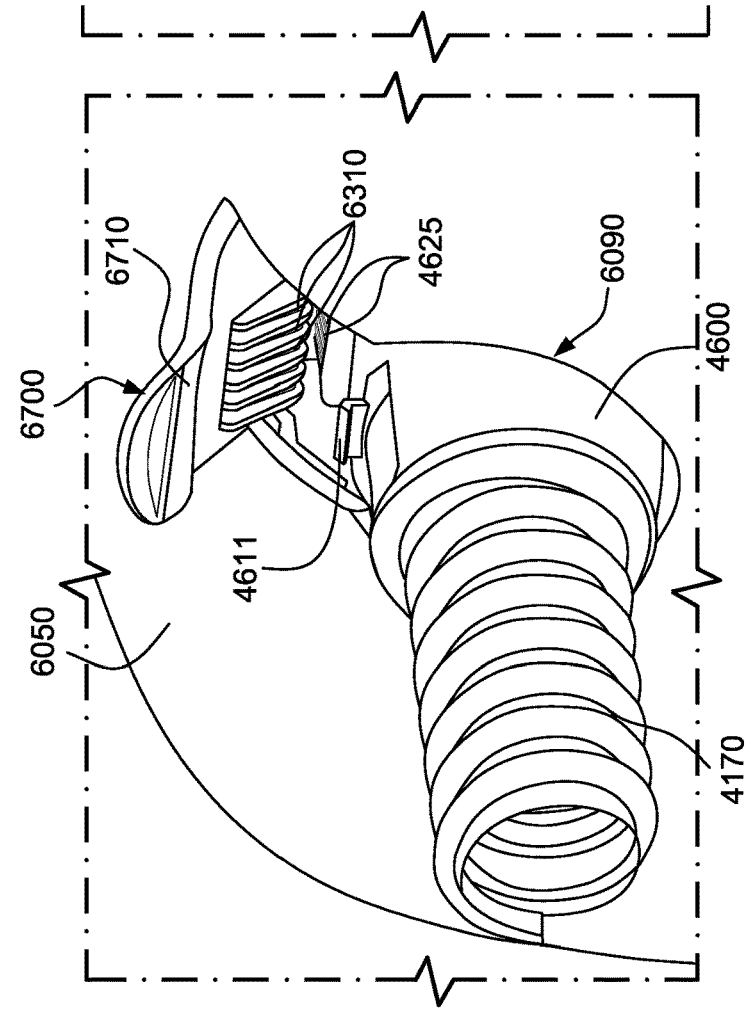
Figures 4, 8:
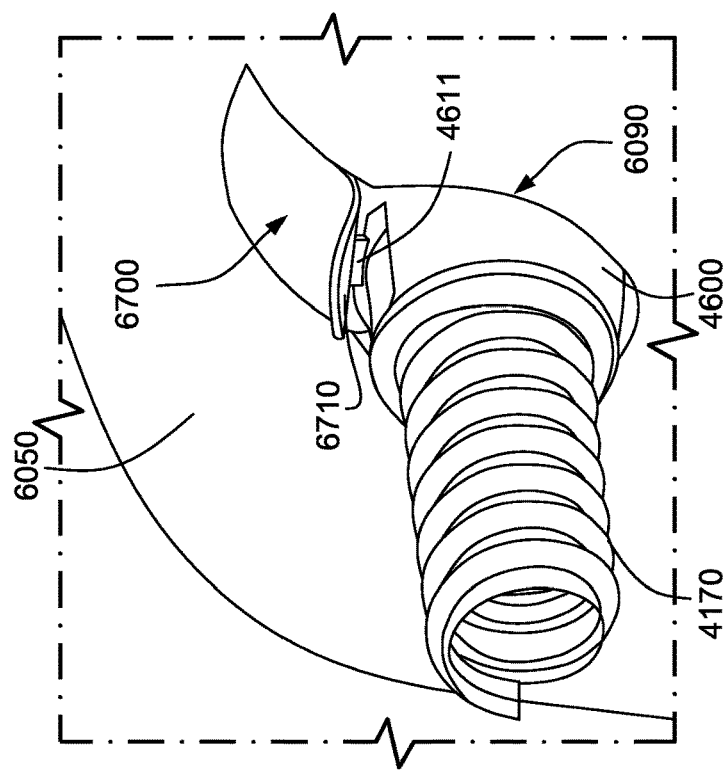
Figures 3, 8:
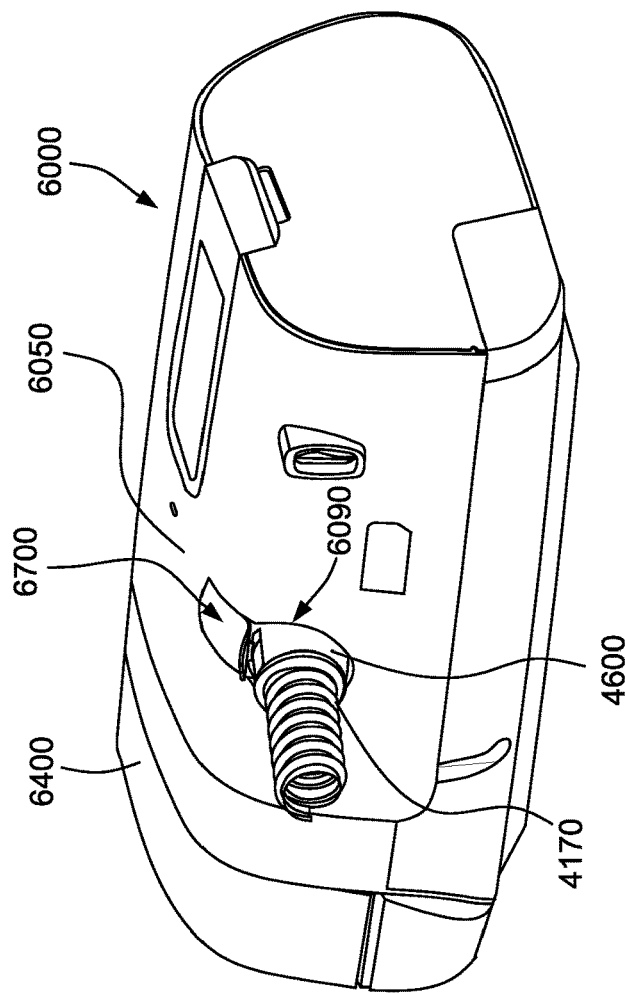
Figures 1, 9:
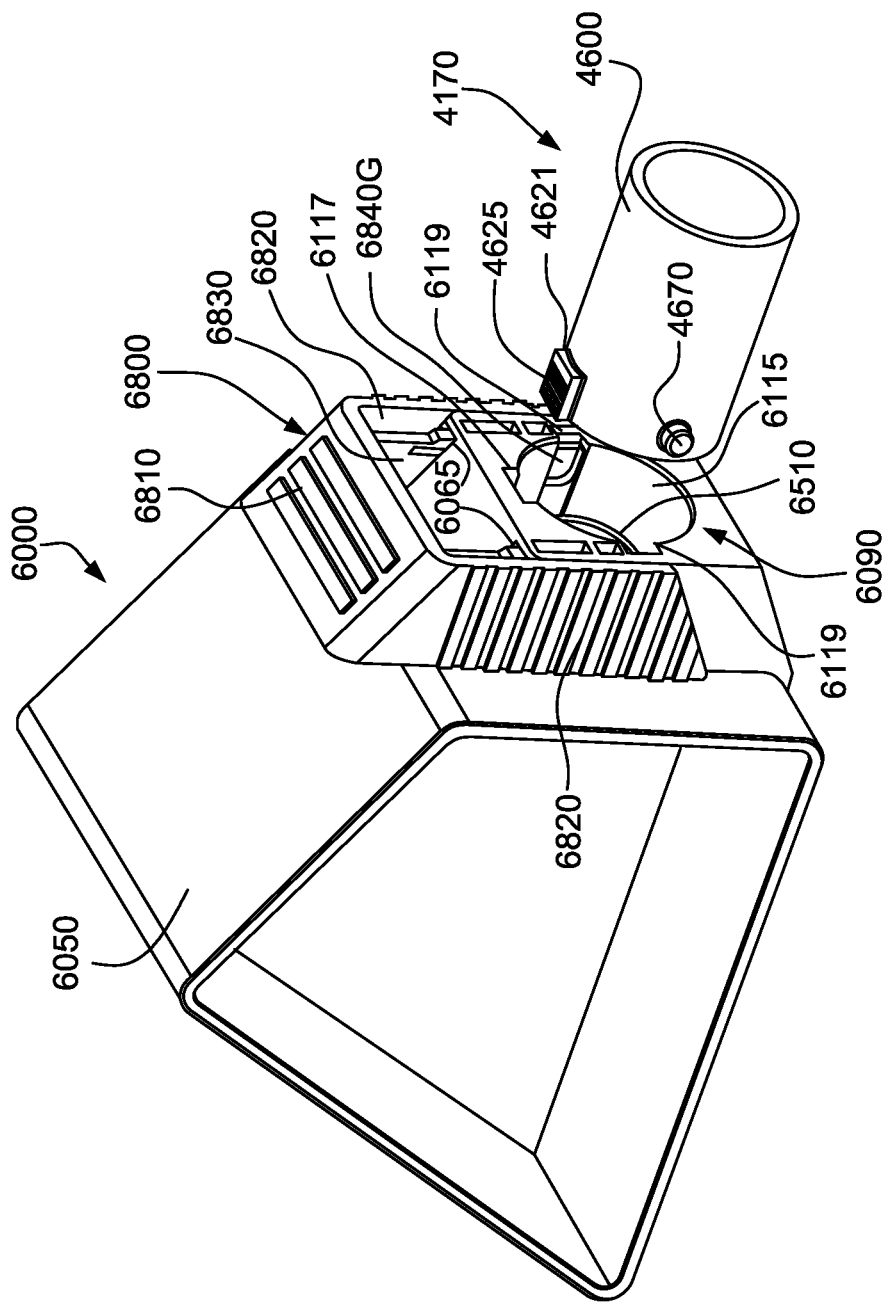
Figures 4, 9:
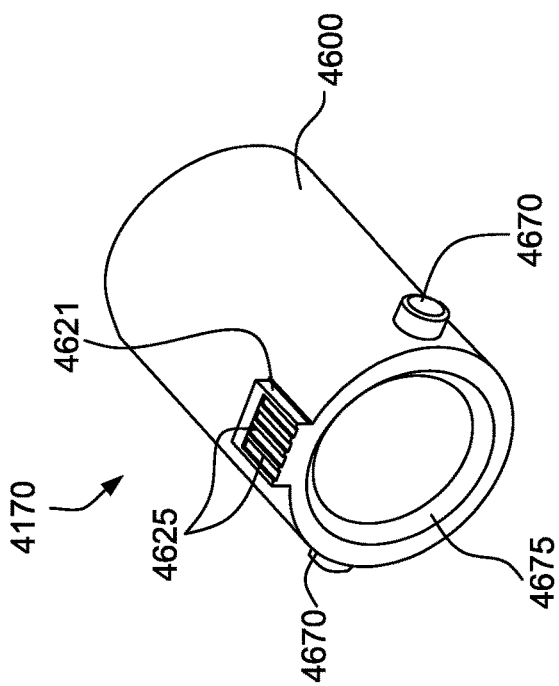
Figures 2, 9:
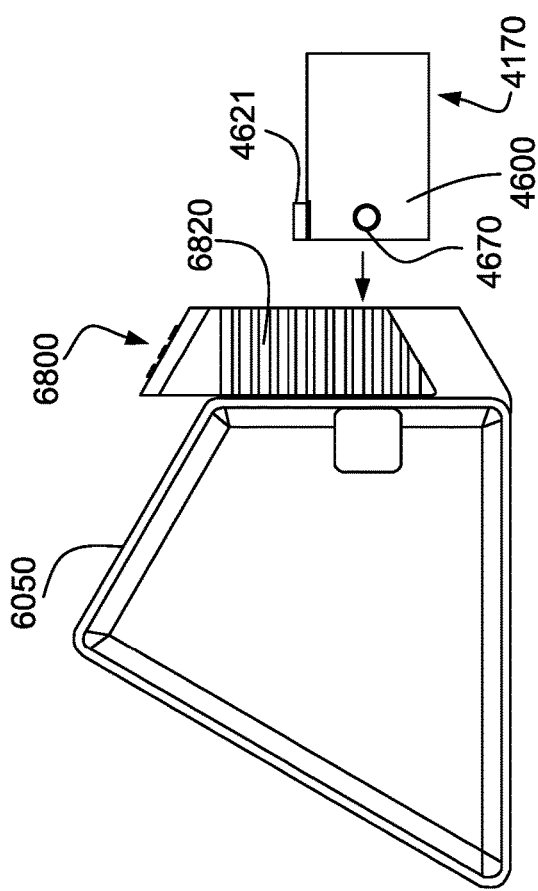
Figures 3, 9:
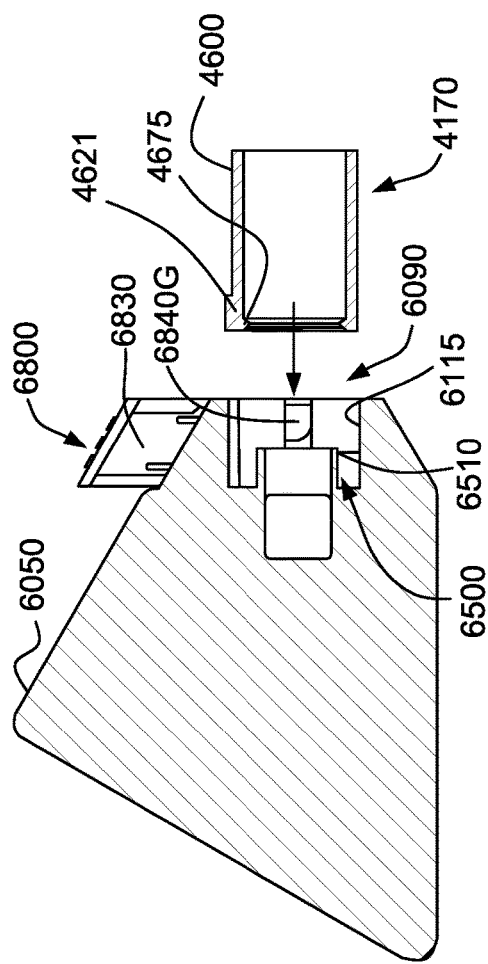
Figures 6, 9:
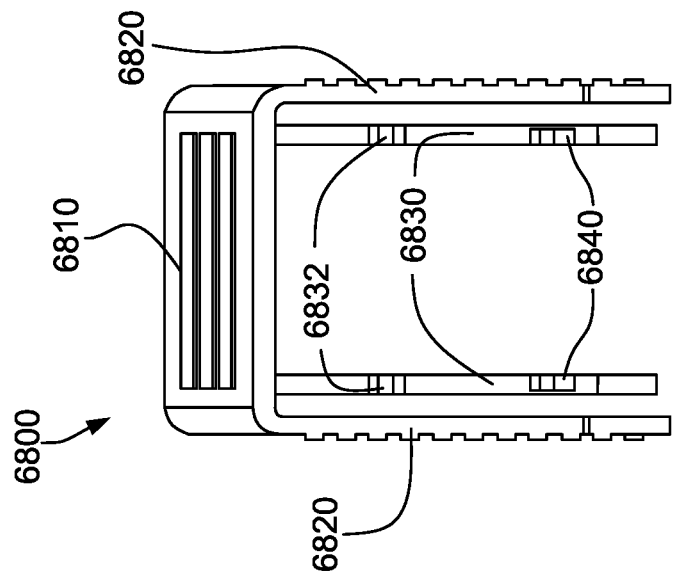
Figures 5, 9:
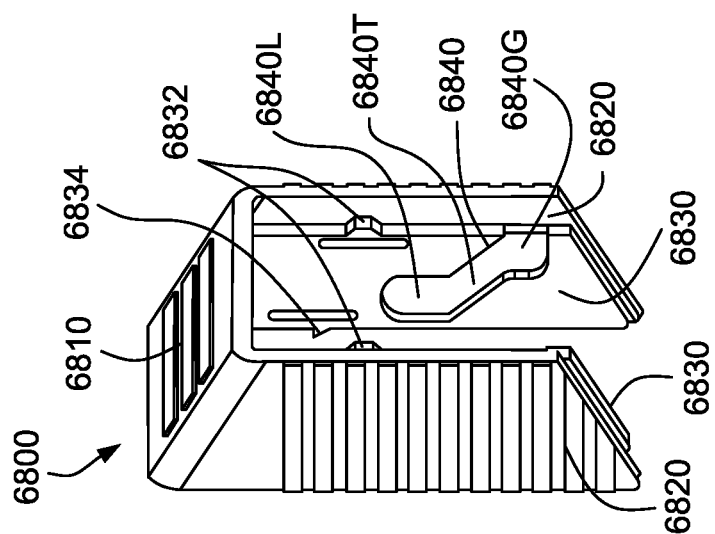
Figures 7, 10:
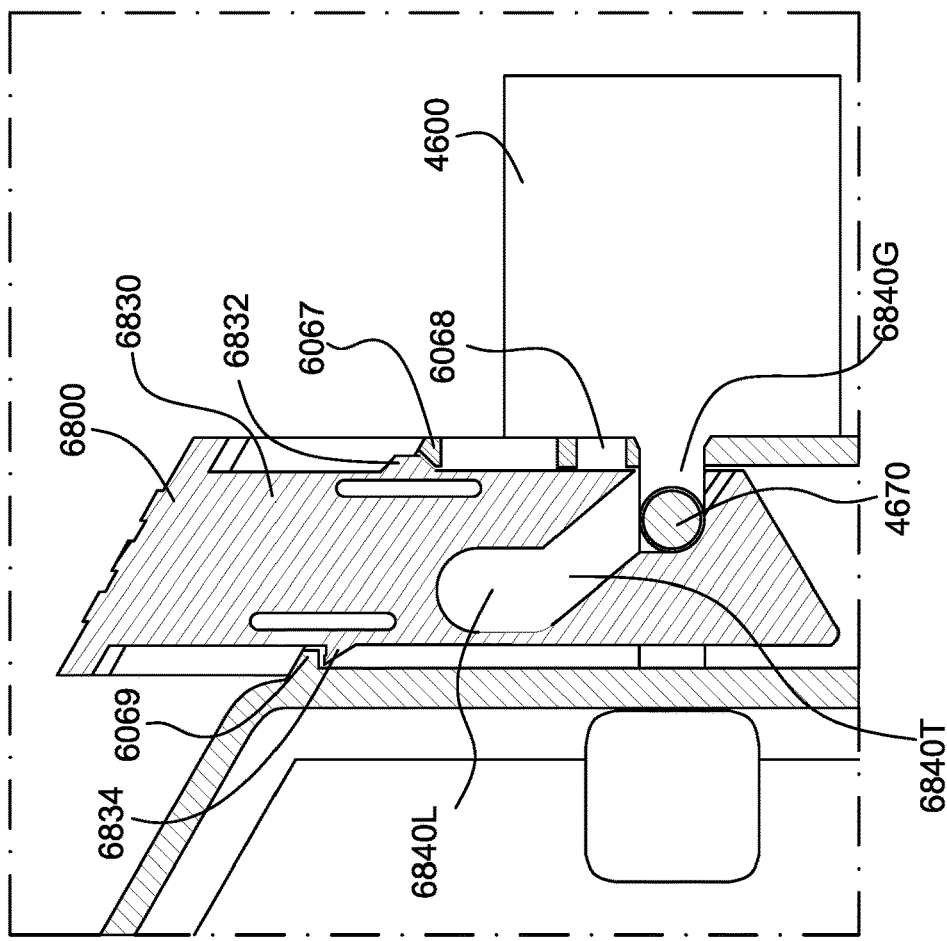
Figures 6, 10:
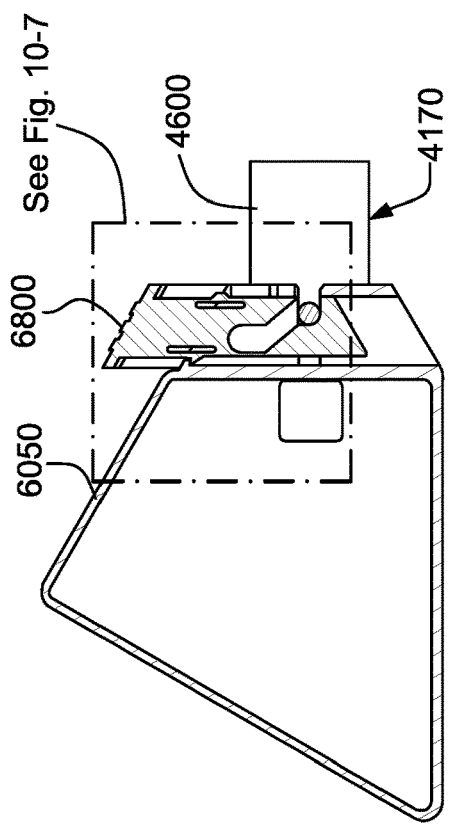
Figures 2, 11:
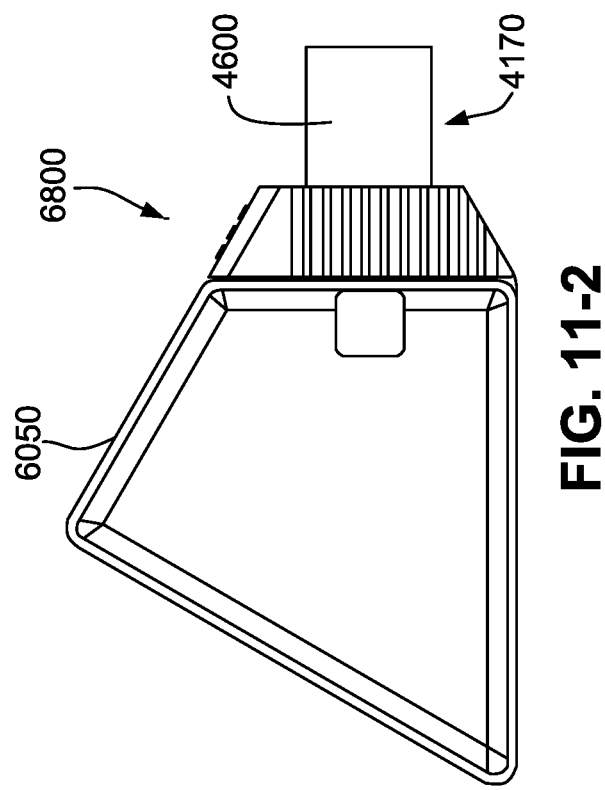
Figures 1, 11:
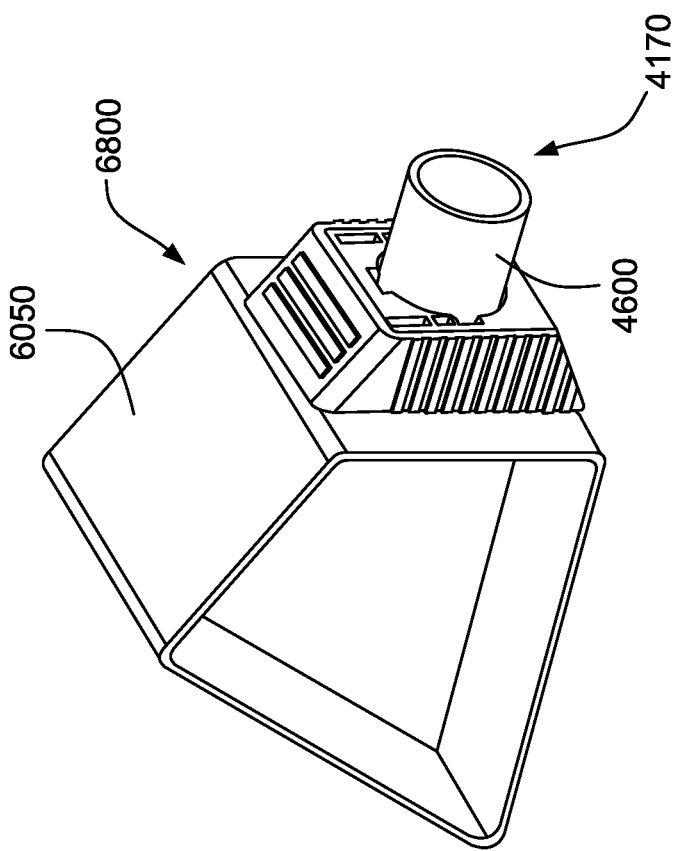
Figures 4, 11:
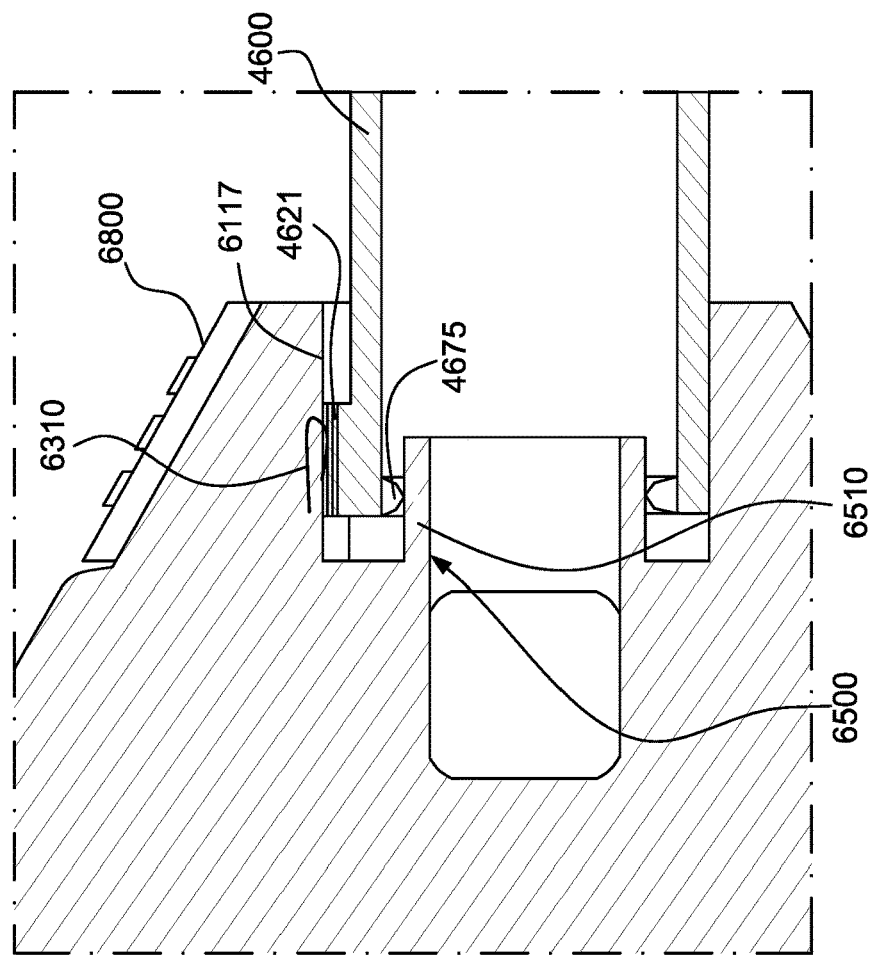
Figures 3, 11:
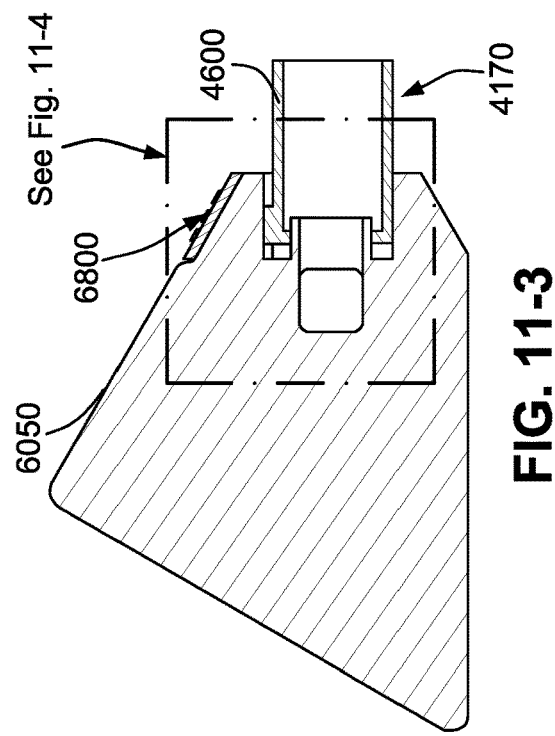
Figures 7, 11:
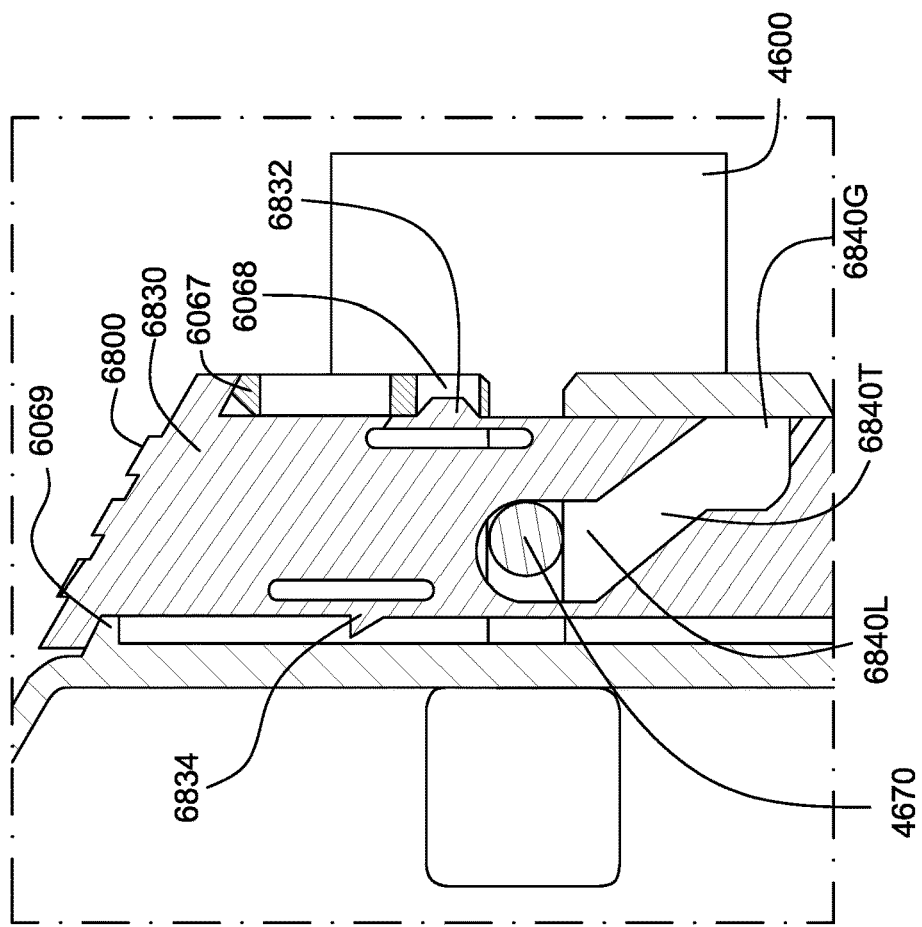
Figures 5, 11:
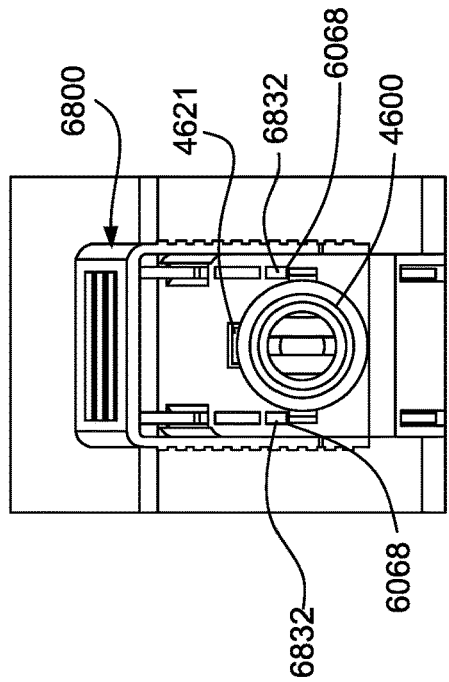
Figures 6, 11:
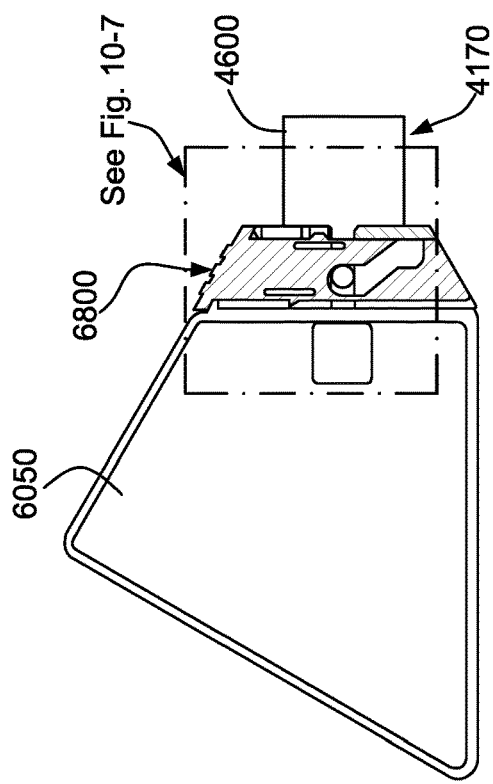
Figures 1, 12:
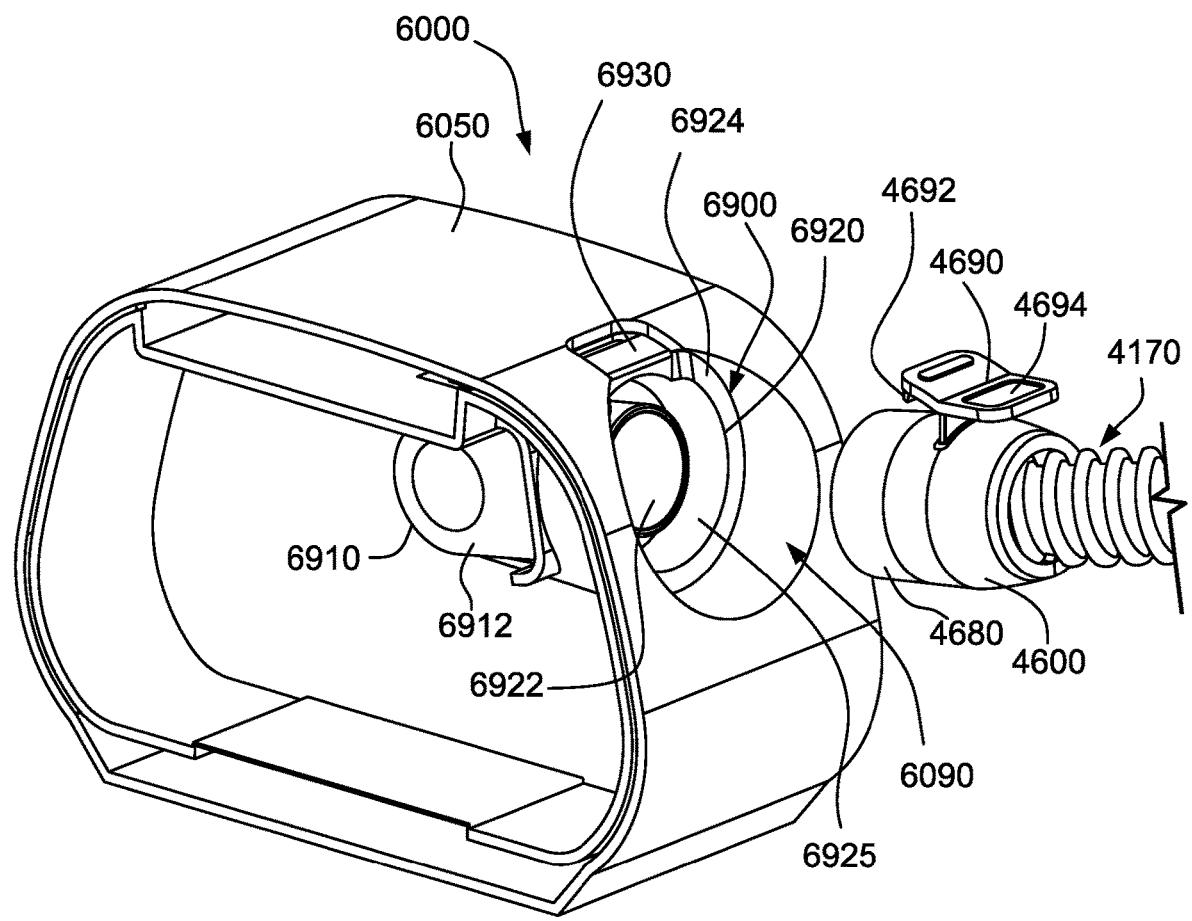
Figures 2, 12:
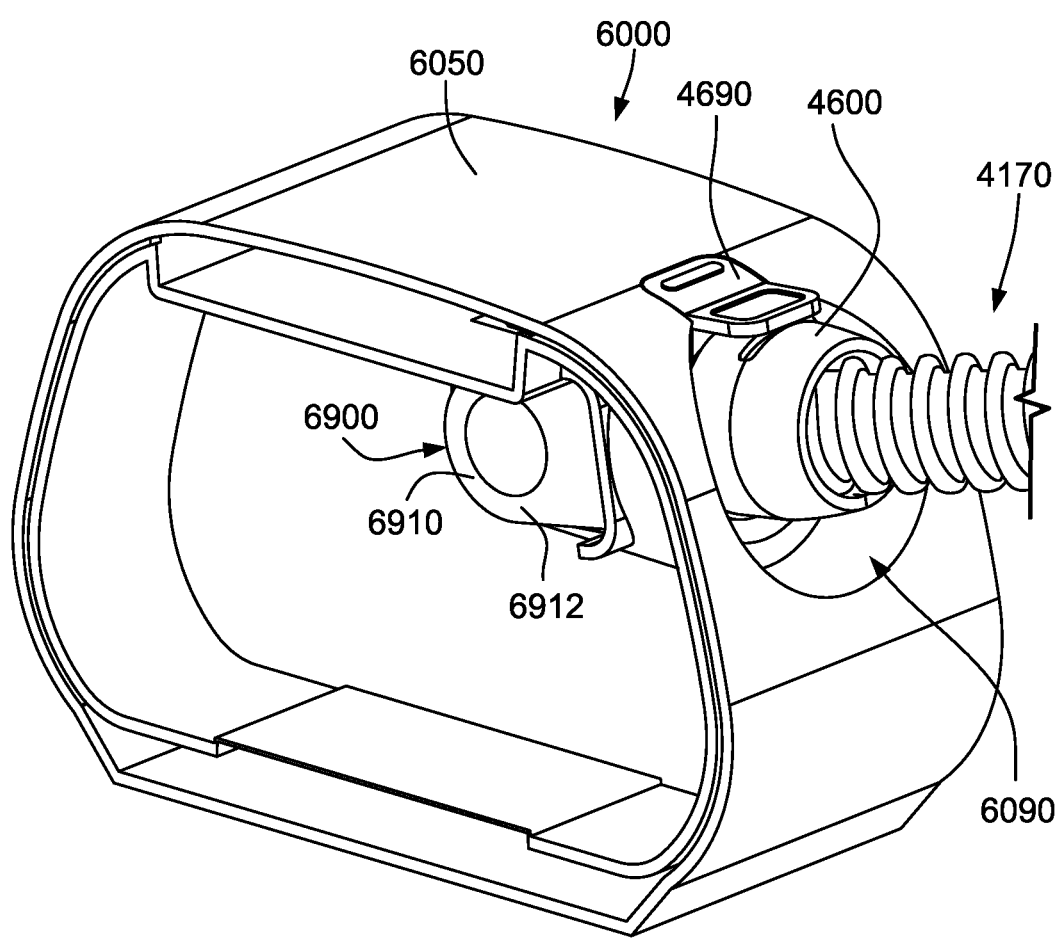
Figures 3, 12:
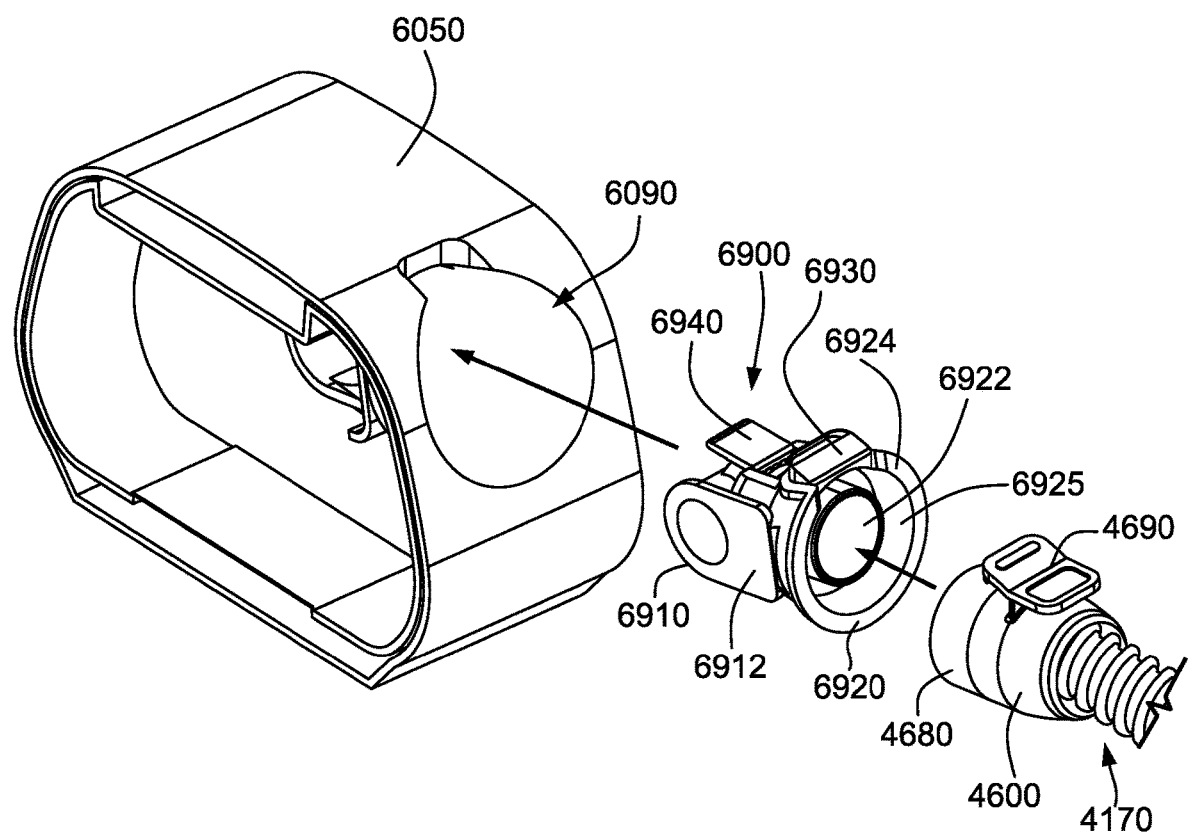
Figures 4, 12:
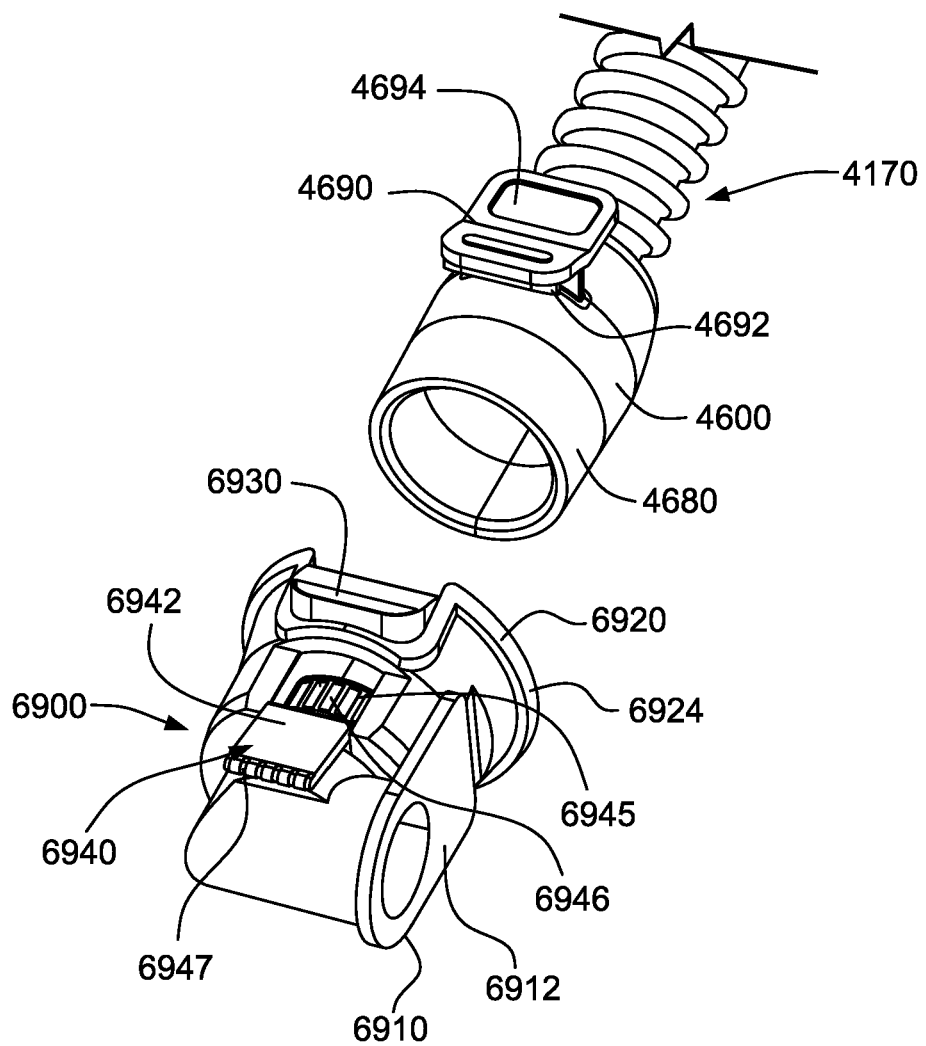
Figures 5, 12:
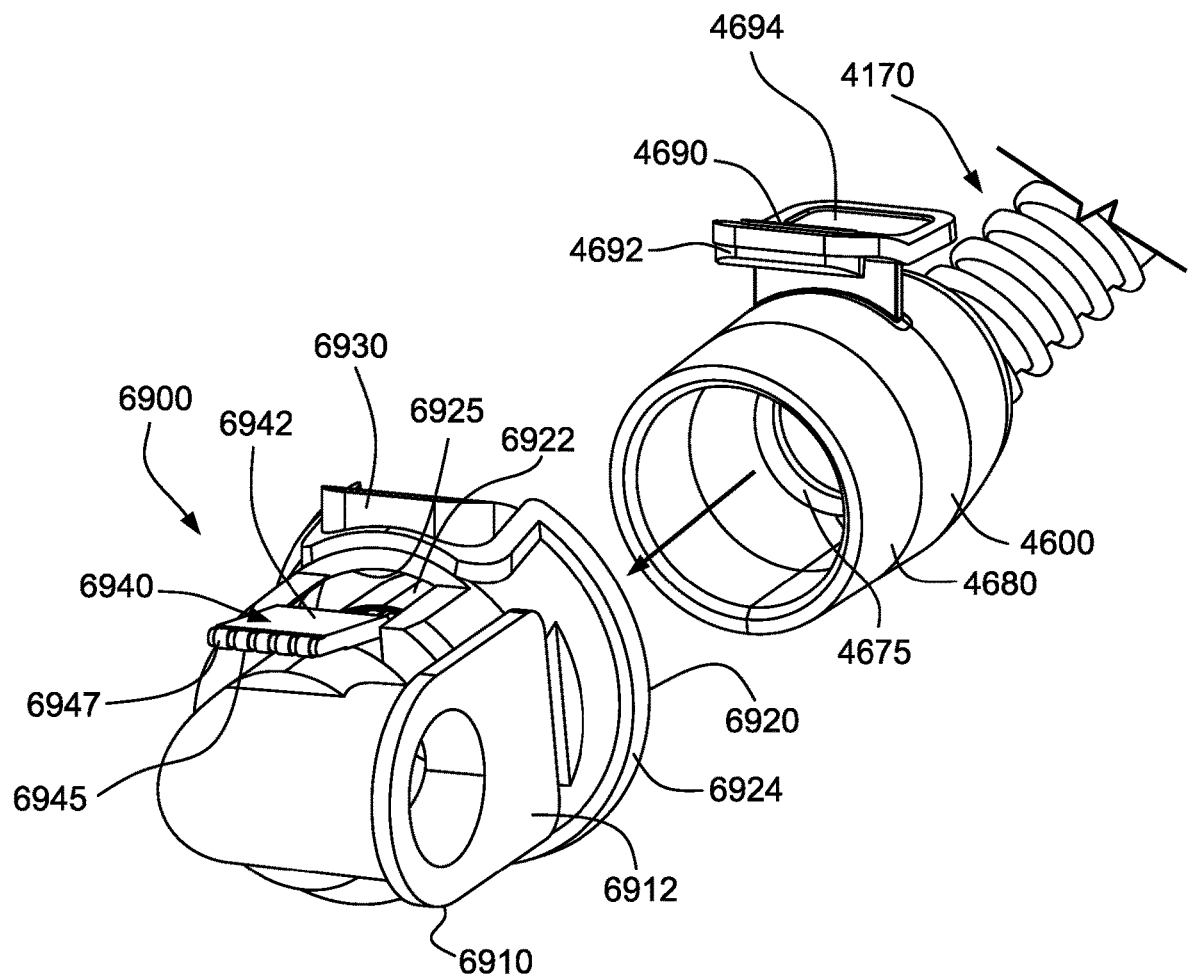
Figures 6, 12:
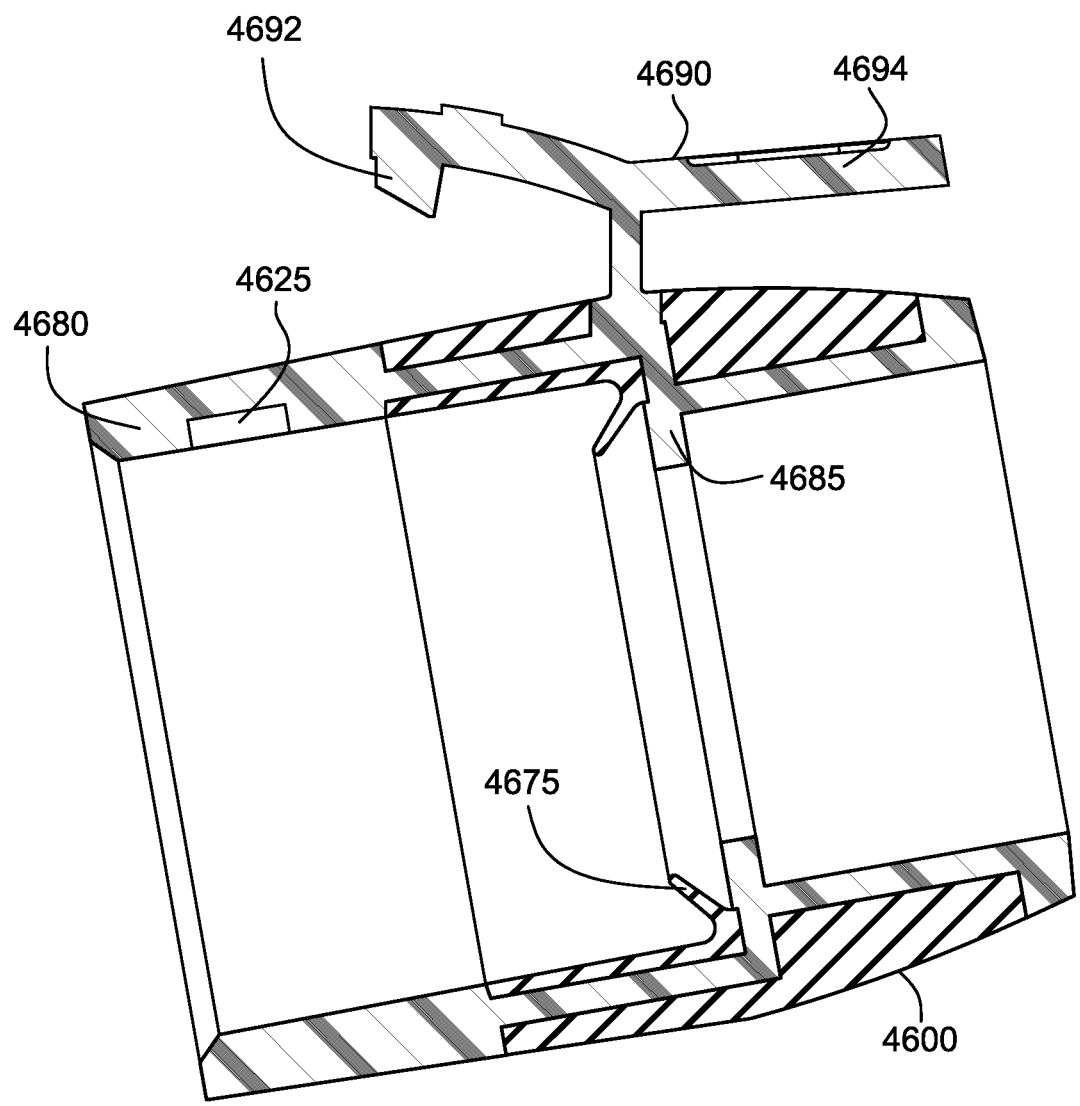
Figures 7, 12:
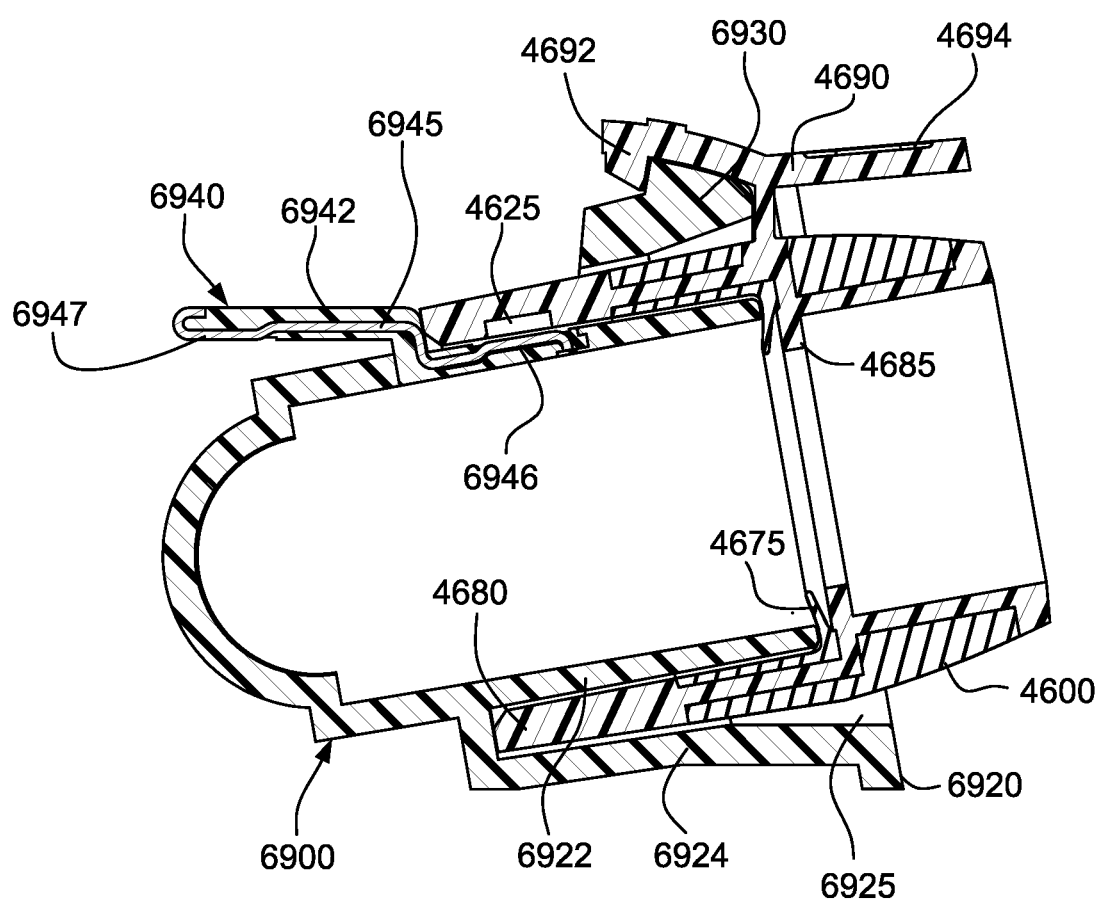
Figures 1, 15:
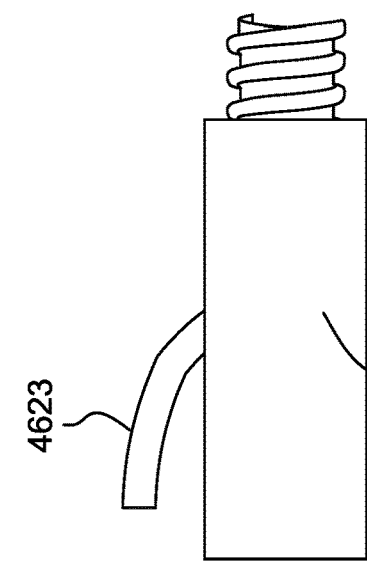
Figures 2, 15:
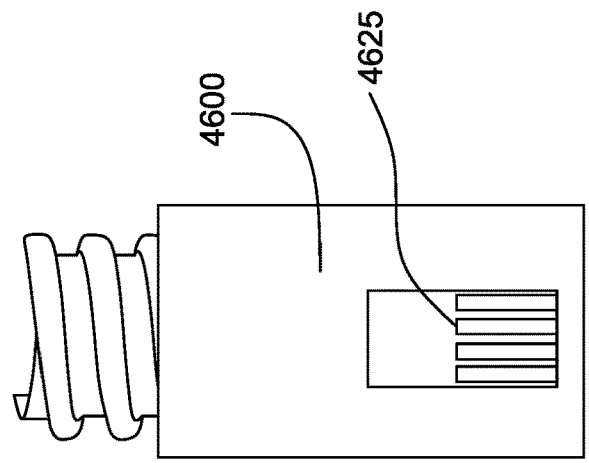
Figures 1, 14:
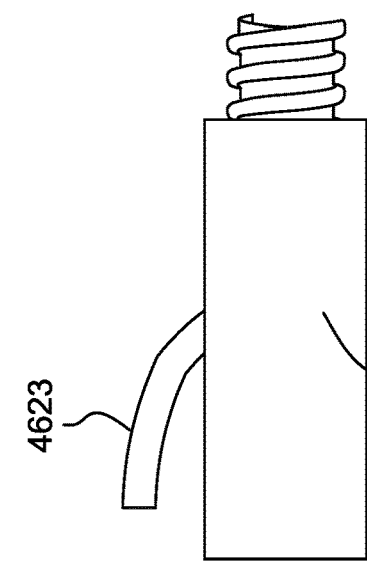
Figures 2, 14:
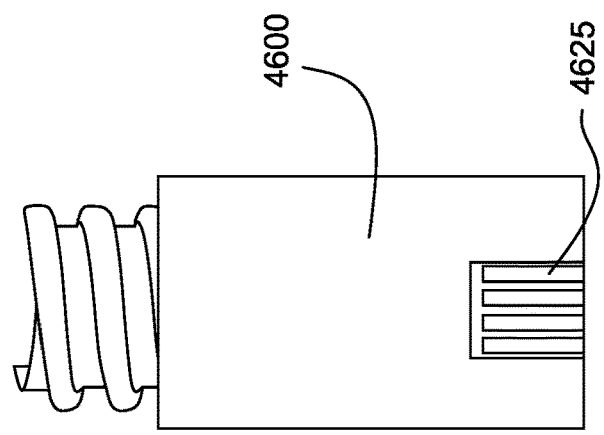
Figures 1, 13:
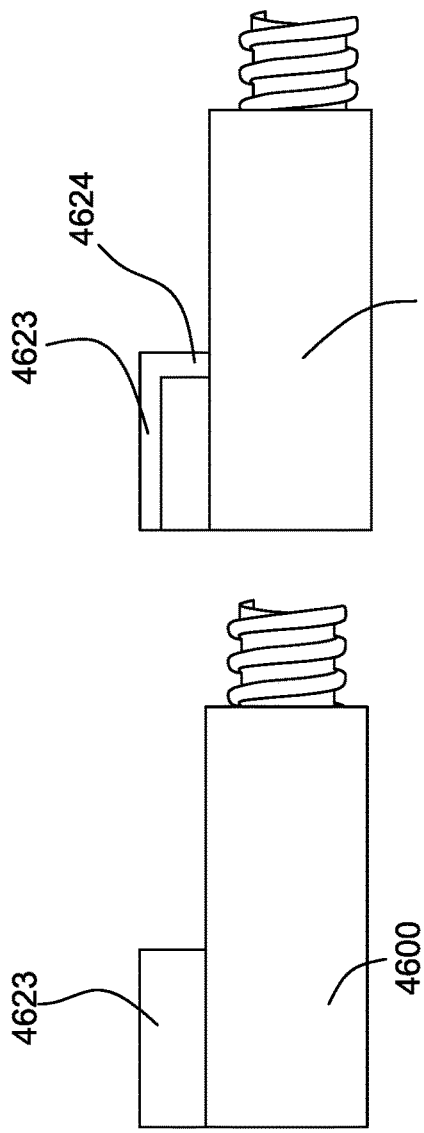
Figures 2, 13:
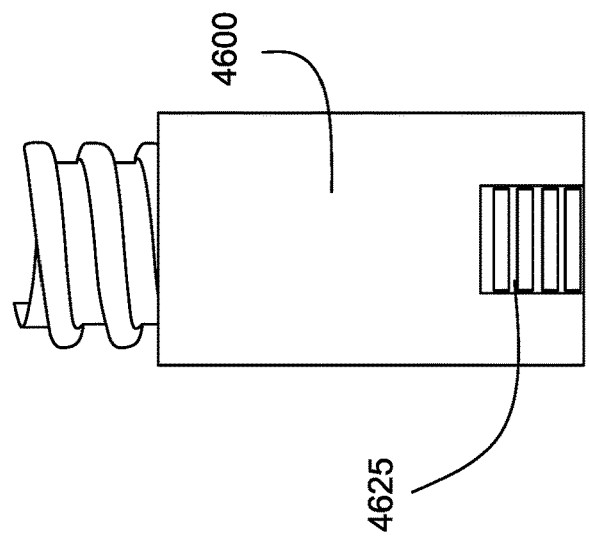

FIG. 6-3 is a front view (transverse to the view in FIG. 6-2) showing an interface at the dock outlet of integrated RPT device and humidifier according to an example of the present technology.

Figure 4:
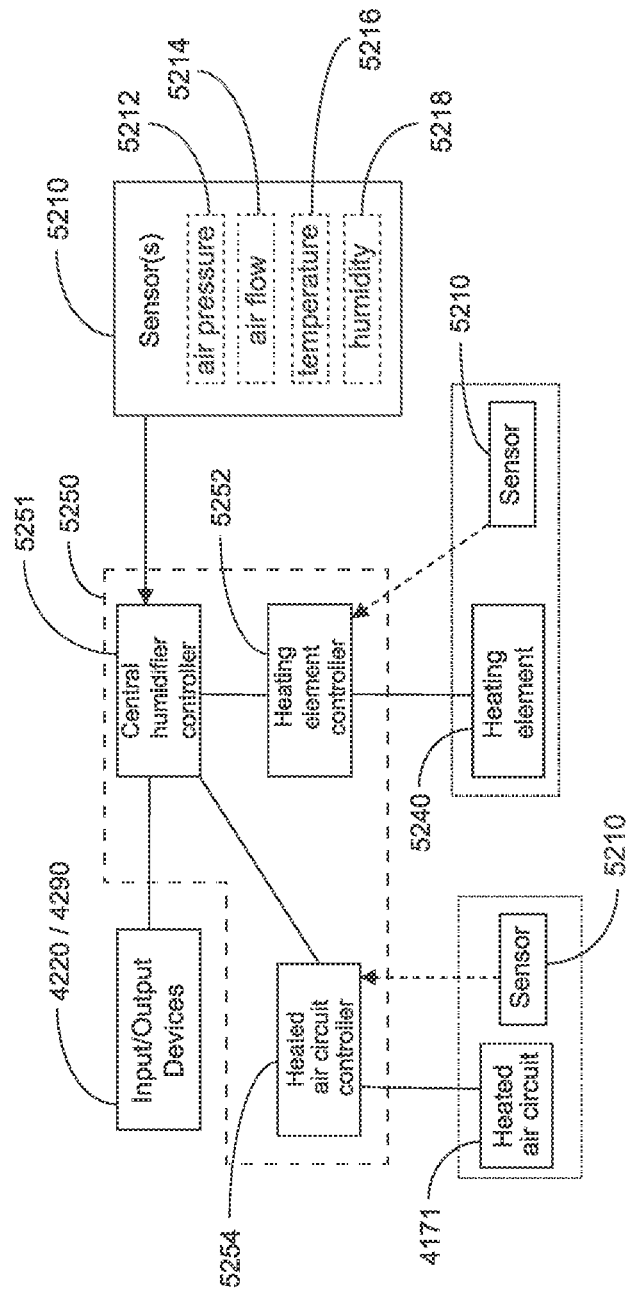
FIG. 4 shows a schematic of a humidifier control circuit in accordance with one form of the present technology.

FIG. 6-4 is a cross-sectional view (along line 6-4-6-4 and transverse to the view in FIG. 6-2) showing an interface at the dock connector of the air delivery tube according to an example of the present technology.

FIGS. 6-5 to 6-10 are cross-sectional views similar to the cross-sectional view of FIG. 6-2 and showing sequential stages of the connection of the dock connector of the air delivery tube to the dock outlet of the integrated RPT device and humidifier according to an example of the present technology.

FIGS. 6-11 to 6-14 are cross-sectional views similar to the cross-sectional view of FIG. 6-2 and showing sequential stages of the disconnection of the dock connector of the air delivery tube from the dock outlet of the integrated RPT device and humidifier according to an example of the present technology.

FIG. 7-1 is a perspective view showing a dock connector of an air delivery tube according to an example of the present technology.

FIG. 7-2 is a side view of the dock connector of FIG. 7-1.

FIG. 7-3 is a top view of the dock connector of FIG. 7-1.

FIG. 7-4 is a perspective view showing engagement of the dock connector of FIG. 7-1 with a water reservoir according to an example of the present technology.

FIG. 7-5 is a top view showing engagement of the dock connector of FIG. 7-1 with a water reservoir according to an example of the present technology.

FIG. 7-6 is an enlarged view of a portion of FIG. 7-5.

FIG. 7-7 is a perspective view showing the dock connector of FIG. 7-1 aligned for engagement with a water reservoir according to an example of the present technology.

FIG. 8-1 is a perspective view showing an RPT device and humidifier including a pivotable locking latch for an air delivery tube in an unlocked position according to an example of the present technology.

FIG. 8-2 is an enlarged perspective view showing the pivotable locking latch of FIG. 8-1 in an unlocked position.

FIG. 8-3 is a perspective view showing the pivotable locking latch of FIG. 8-1 in a locked position.

FIG. 8-4 is an enlarged view of a portion of FIG. 8-3 showing the pivotable locking latch in a locked position.

FIG. 9-1 is a perspective view showing an RPT device and humidifier including a locking button for an air delivery tube in an unlocked position according to an example of the present technology.

FIG. 9-2 is a side view showing the RPT device and humidifier, the locking button in the unlocked position, and the air delivery tube of FIG. 9-1.

FIG. 9-3 is a cross-sectional view showing the RPT device and humidifier, the locking button in the unlocked position, and the air delivery tube of FIG. 9-1.

FIG. 9-4 is a perspective view of a dock connector for an air delivery tube according to an example of the present technology.

FIG. 9-5 is a perspective view of a locking button for an RPT device and humidifier according to an example of the present technology.

FIG. 9-6 is a front view of the locking button of FIG. 9-5.

FIG. 10-1 is a perspective view showing an RPT device and humidifier, a locking button in an unlocked position, and an air delivery tube inserted into the locking button according to an example of the present technology.

FIG. 10-2 is a side view showing the RPT device and humidifier, the locking button in the unlocked position, and the air delivery tube of FIG. 10-1 inserted into the locking button.

FIG. 10-3 is a cross-sectional view showing the RPT device and humidifier, the locking button in the unlocked position, and the air delivery tube of FIG. 10-1 inserted into the locking button.

FIG. 10-4 is an enlarged view of a portion of FIG. 10-3.

FIG. 10-5 is a front view showing the RPT device and humidifier, the locking button in the unlocked position, and the air delivery tube of FIG. 10-1 inserted into the locking button.

FIG. 10-6 is another cross-sectional view showing the RPT device and humidifier, the locking button in the unlocked position, and the air delivery tube of FIG. 10-1 inserted into the locking button.

FIG. 10-7 is an enlarged view of a portion of FIG. 10-6.

FIG. 11-1 is a perspective view showing an RPT device and humidifier, a locking button in a locked position, and an air delivery tube inserted into the locking button according to an example of the present technology.

FIG. 11-2 is a side view showing the RPT device and humidifier, the locking button in the locked position, and the air delivery tube of FIG. 11-1 inserted into the locking button.

FIG. 11-3 is a cross-sectional view showing the RPT device and humidifier, the locking button in the locked position, and the air delivery tube of FIG. 11-1 inserted into the locking button.

FIG. 11-4 is an enlarged view of a portion of FIG. 11-3.

FIG. 11-5 is a front view showing the RPT device and humidifier, the locking button in the locked position, and the air delivery tube of FIG. 11-1 inserted into the locking button.

FIG. 11-6 is another cross-sectional view showing the RPT device and humidifier, the locking button in the locked position, and the air delivery tube of FIG. 11-1 inserted into the locking button.

FIG. 11-7 is an enlarged view of a portion of FIG. 11-6.

FIG. 12-1 is a perspective view showing an integrated RPT device and humidifier and an air delivery tube including an interface arrangement according to an example of the present technology.

FIG. 12-2 is a perspective view of the integrated RPT device and humidifier and the air delivery tube of FIG. 12-1 showing connection of the air delivery tube to the integrated RPT device and humidifier.

FIG. 12-3 is an exploded view of the integrated RPT device and humidifier and the air delivery tube of FIG. 12-1.

FIG. 12-4 is a perspective view of an intermediate component and an air delivery tube according to an example of the present technology.

FIG. 12-5 is another perspective view of the intermediate component and the air delivery tube of FIG. 12-4.

FIG. 12-6 is a cross-sectional view showing a dock connector of an air delivery tube according to an example of the present technology.

FIG. 12-7 is a cross-sectional view showing connection of a dock connector of an air delivery tube to an intermediate component according to an example of the present technology.

FIGS. 13-1 to 13-3, 14-1 to 14-3, and 15-1 to 15-3 are various views of a dock connector for an air delivery tube including a contact support structure and contacts according to three different examples of the present technology.

Figures 5, 6, 7, 8, 9, 10, 11, 12, 13:
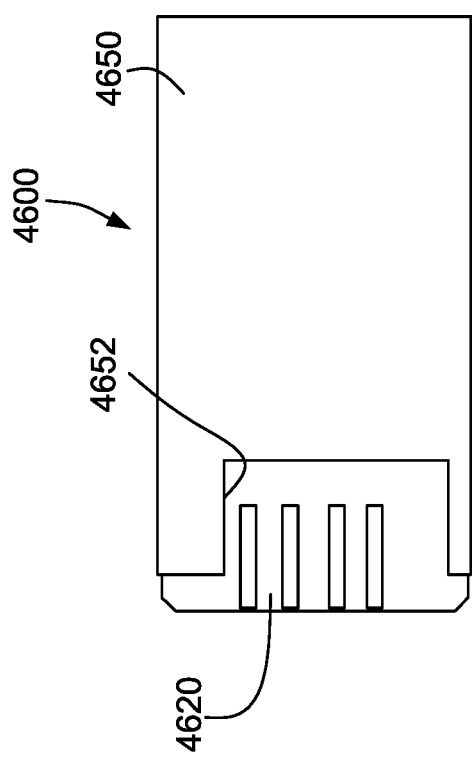
Figures 5, 6, 7, 8, 9, 10, 11, 12, 13, 14:
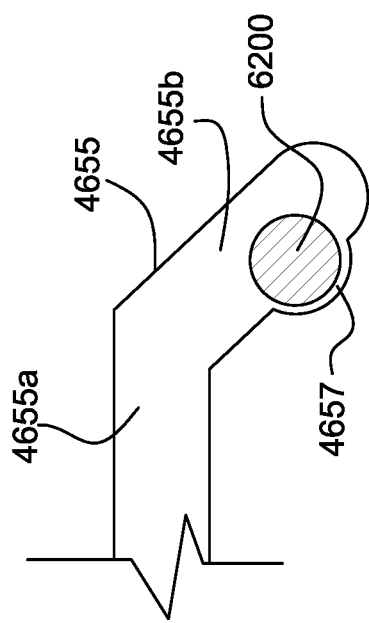

FIGS. 14-4 to 14-6 show alternative contact support structures and contacts for the dock connector of FIGS. 14-1 to 14-3.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The a respiratory therapy system may comprise an RPT device 4000 for supplying a flow of air to the patient 1000 via an air circuit 4170 and a patient interface 3000, e.g., see FIG. 1.

5.3 Patient Interface

FIG. 2 shows a non-invasive patient interface 3000 in accordance with one aspect of the present technology comprising the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 RPT Device

Figure 3A:
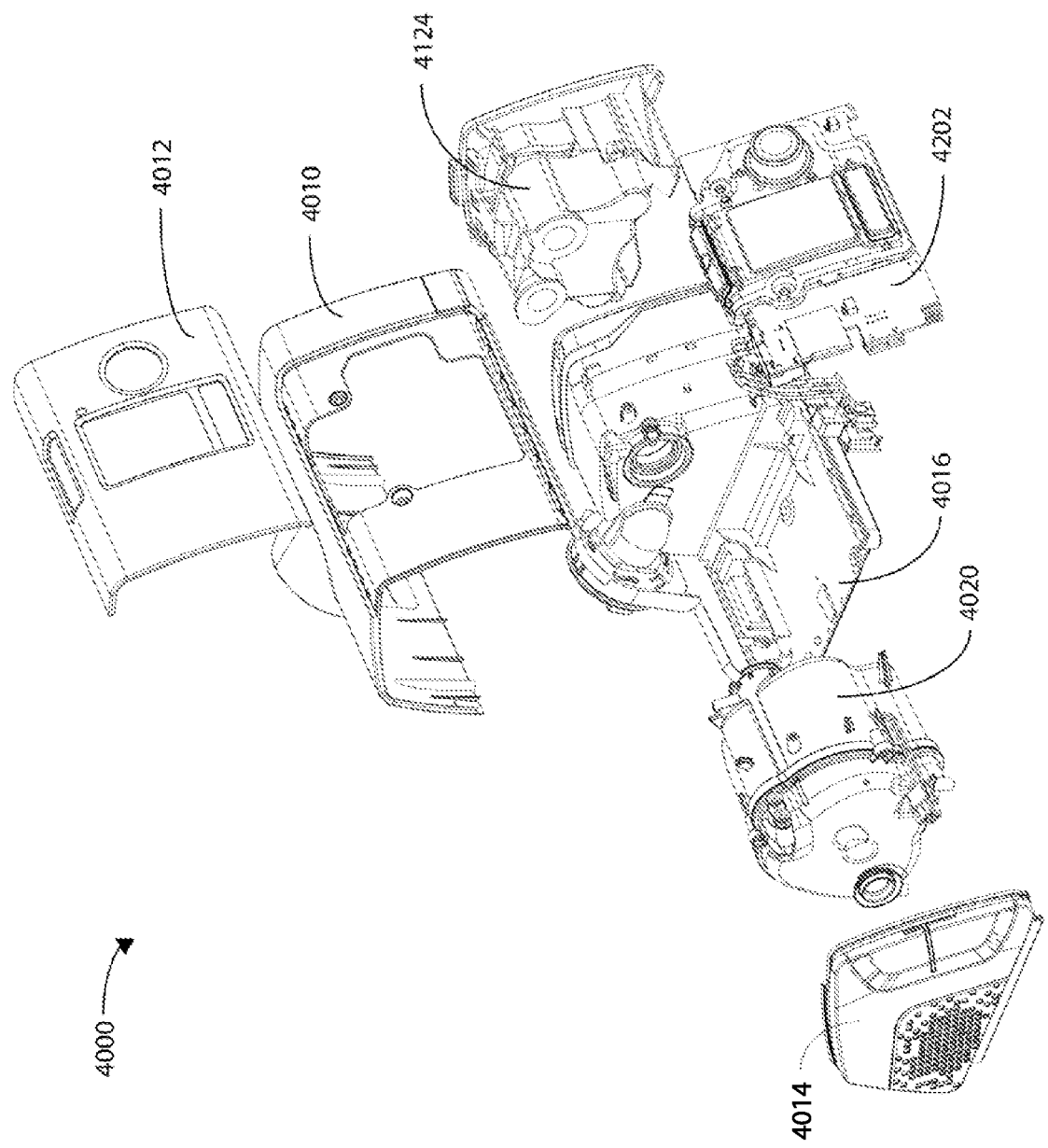
FIG. 3A is an exploded perspective view of an RPT device 4000 in accordance with one form of the present technology.

An exploded view of an RPT device 4000 in accordance with one aspect of the present technology is shown in FIG. 3A. An RPT device 4000 may comprise mechanical, pneumatic, and/or electrical components and be configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

Figure 3B:
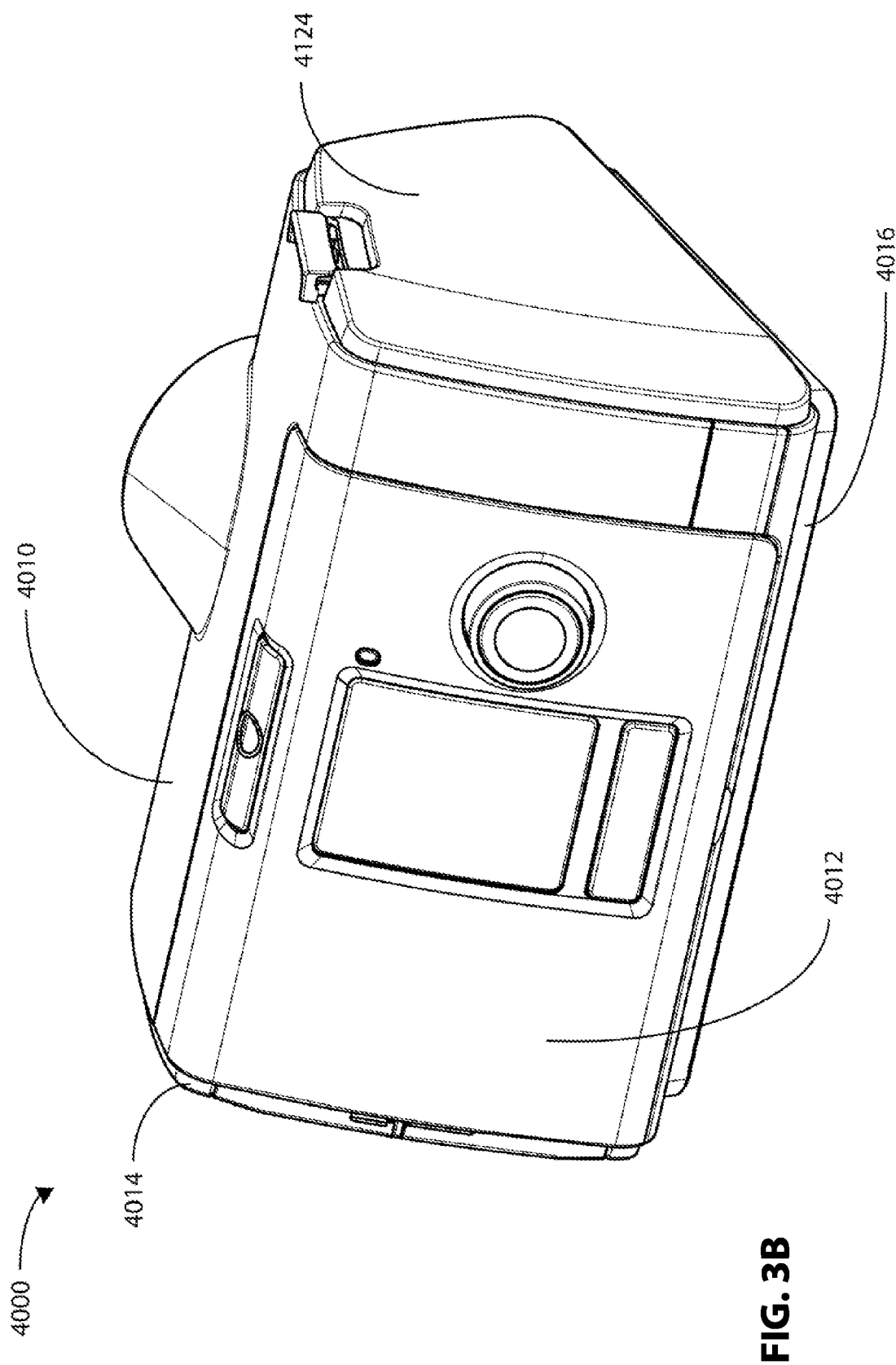
FIG. 3B is a perspective view of an RPT device 4000 comprising an outlet muffler 4124 in accordance with one form of the present technology.
Figure 3C:
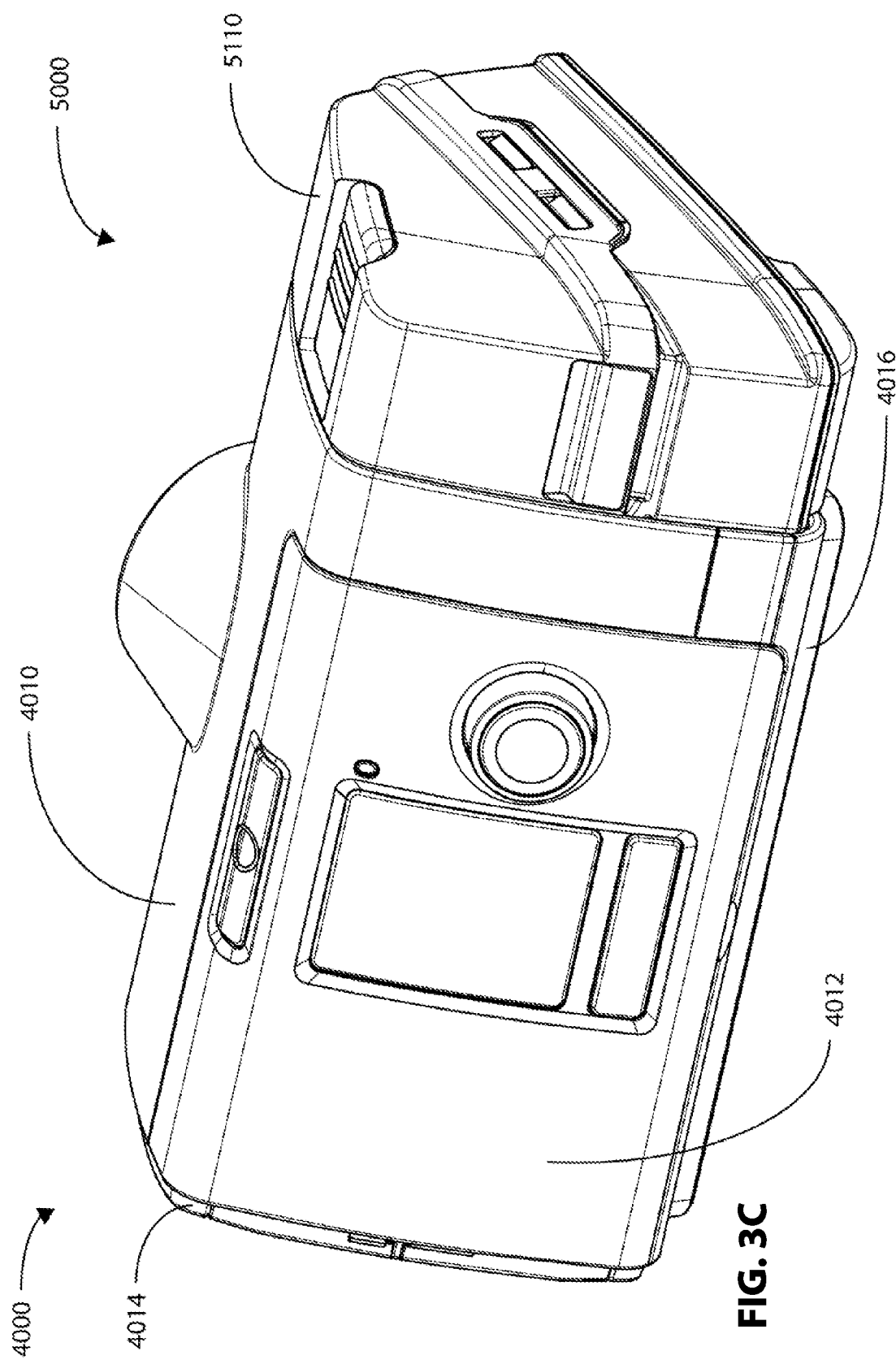
FIG. 3C is a perspective view of an RPT device 4000 with an integrated humidifier 5000 comprising a water reservoir 5110 in accordance with one form of the present technology.
Figure 3D:
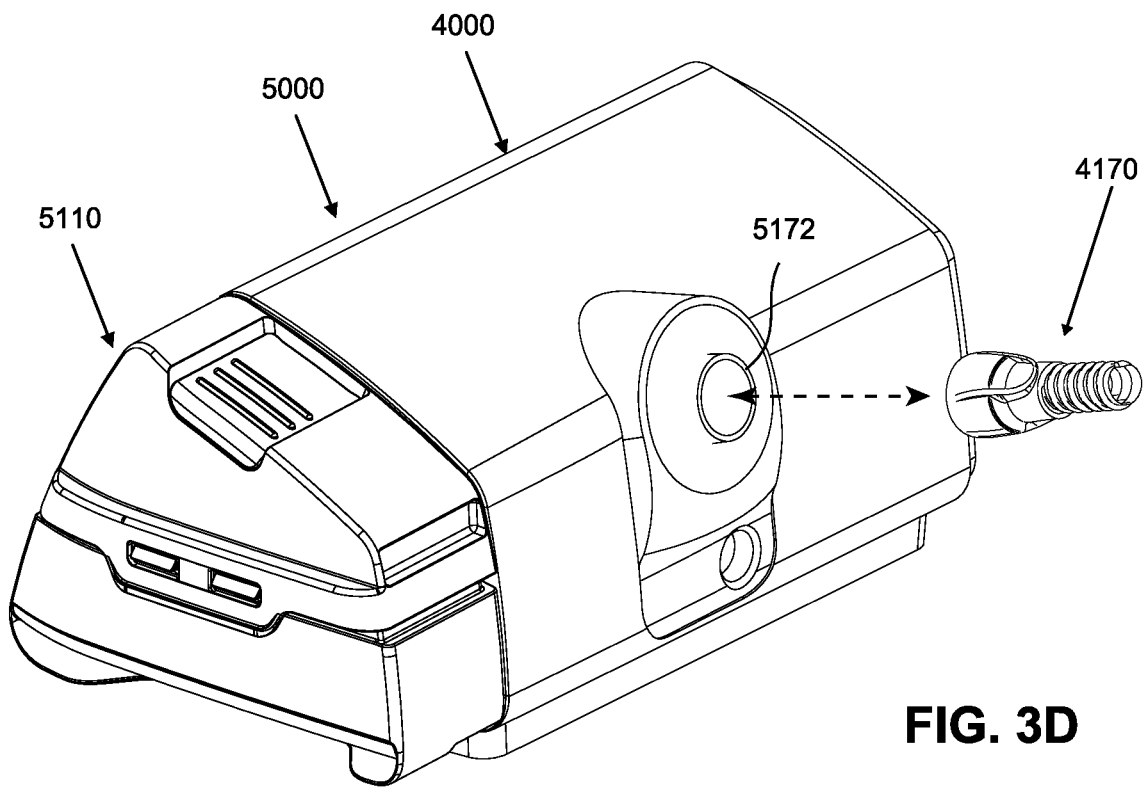
FIG. 3D is a perspective view of an RPT device 4000 with an integrated humidifier 5000 according to an example of the present technology, and demonstrating engagement with the air circuit 4170 according to an example of the present technology.

The RPT device 4000 may include an external housing having one or more panel(s) such as a main panel 4010, a front panel 4012 and a side panel 4014. The RPT device 4000 may also comprise an outlet muffler 4124 as shown in FIGS. 3A and 3B. The outlet muffler 4124 may be removable and replaced with a water reservoir 5110 (see FIGS. 3C to 3E). In such forms, the RPT device 4000 may be considered to include an integrated humidifier 5000. Thus, the RPT device 4000 may be used with or without humidification depending upon whether the water reservoir 5110 or the outlet muffler 4124 respectively is attached. Preferably the RPT device 4000 comprises a chassis 4016 that supports one or more internal components of the RPT device 4000. In one form the RPT device 4000 comprises a pressure generator, which may be housed in a pneumatic block 4020 coupled to the chassis 4016.

Electrical components may be mounted on a single Printed Circuit Board Assembly (PCBA) 4202. In an alternative form, the RPT device 4000 may include more than one PCBA 4202.

Further examples and details of an exemplary RPT device are described in PCT Publication No. WO 2015/089582, which is incorporated herein by reference in its entirety.

A power supply may be located internal or external of the external housing 4010 of the RPT device 4000.

In one form of the present technology, power supply provides electrical power to the RPT device 4000 only. In another form of the present technology, power supply provides electrical power to both RPT device 4000 and humidifier 5000.

In one form of the present technology, the RPT device includes a central controller including one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers, one or more input devices 4220, and the humidifier 5000.

The central controller may be configured to provide output signal(s) to one or more of an output device 4290, a therapy device controller, a data communication interface, and the humidifier 5000.

In some forms of the present technology, the central controller is configured to implement the one or more methodologies described herein, such as the one or more algorithms expressed as computer programs stored in a non-transitory computer readable storage medium, such as memory. In some forms of the present technology, the central controller may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, is delivered to one or more points in the pneumatic path, such as upstream of the pneumatic block 4020, to the air circuit 4170, and/or to the patient interface 3000.

5.6 Humidifier

5.6.1 Humidifier Overview

In one form of the present technology there is provided a humidifier 5000 (e.g. as shown in FIGS. 3C to 3F) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

FIGS. 3C to 3F show a RPT device 4000 with an integrated humidifier 5000 according to an example of the present technology. In the illustrated example, the humidifier 5000 includes a water reservoir dock 5130 structured to receive a water reservoir 5110. As shown, the water reservoir dock 5130 includes a cavity 5160 formed therein to receive the water reservoir 5110, e.g., the water reservoir 5110 may be insertable/removable from the water reservoir dock 5130 in a lateral direction.

Figure 3E:
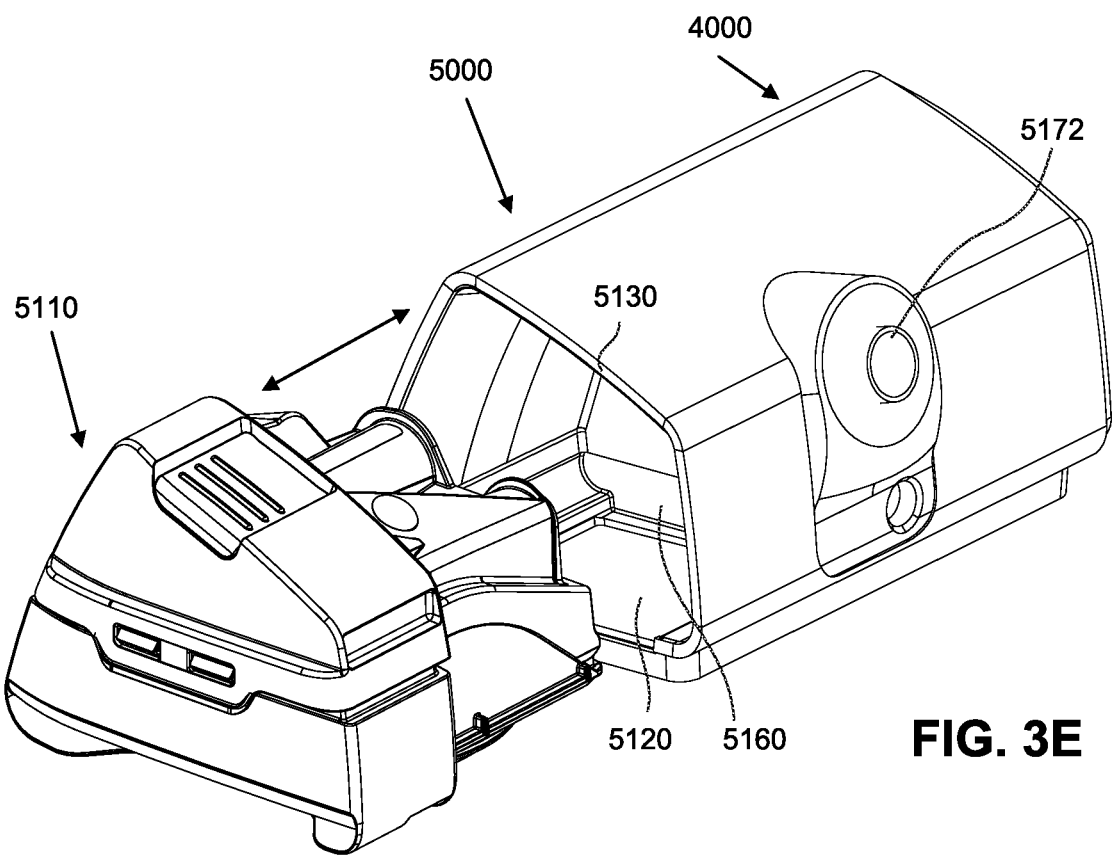
FIG. 3E is a perspective view of the integrated RPT device and humidifier of FIG. 3D demonstrating engagement of the water reservoir 5110 with the reservoir dock 5130 according to an example of the present technology.
Figure 3F:
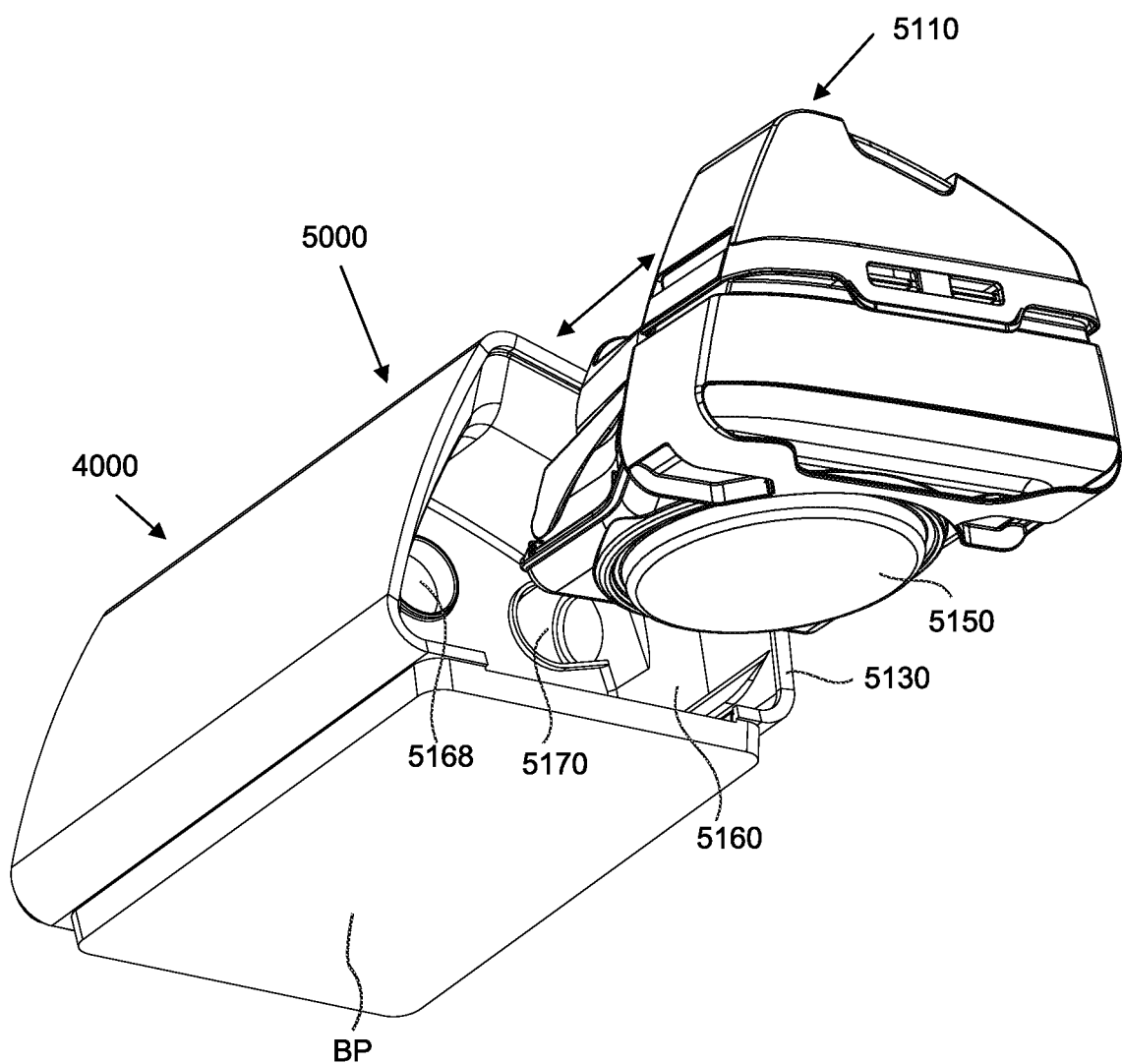
FIG. 3F is another perspective view of the integrated RPT device and humidifier of FIG. 3D demonstrating engagement of the water reservoir 5110 with the reservoir dock 5130 according to an example of the present technology.

In the illustrated example, the RPT device 4000 is integrated with the humidifier 5000. In this arrangement, the water reservoir dock 5130 is structured to connect the water reservoir 5110 to the pneumatic path. As best shown in FIGS. 3E and 3F, the reservoir dock 5130 comprises a dock air outlet 5168 to deliver a flow of air to the water reservoir 5110, a dock air inlet 5170 to receive the flow of air that has been humidified in the water reservoir 5110, and a humidifier outlet 5172 to transfer the flow of humidified air to the air circuit 4170. The cavity 5160 may include a top portion configured to cover at least a portion of the lid of the water reservoir 5110 and a bottom portion including a heater plate 5120.

However, it should be appreciated that the reservoir dock 5130 may be provided to the RPT device 4000 in an alternative arrangement and separately from the water reservoir. In such an arrangement, additional interfaces may be used to connect the reservoir dock 5130 to the RPT device 4000, e.g., directly coupled or coupled via an air circuit.

In another arrangement, the water reservoir dock 5130 may comprise an opening in a substantially horizontal plane, so that the water reservoir 5110 may be inserted from above or below the water reservoir dock 5130.

Further examples and details of such RPT device 4000 and integrated humidifier 5000 are described in PCT Publication No. WO 2014/138804, published Sep. 18, 2014, which is incorporated herein by reference in its entirety.

5.6.2 Humidifier Components

5.6.2.1 Water Reservoir

FIGS. 3C to 3F show a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 3E and FIG. 3F.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5150 configured to allow efficient transfer of heat from the heating element to the volume of liquid in the reservoir 5110 (see FIG. 3F). In one form, the conductive portion 5150 may be arranged as a plate, although other shapes may also be suitable. All or a part of the conductive portion 5150 may be made of a thermally conductive material such as aluminium (e.g., approximately 2 mm thick, such as 1 mm, 1.5 mm, 2.5 mm or 3 mm, however it should be appreciated that thicker or thinner geometries may be used, e.g., less than 1 mm, e.g., 0.4 mm, 0.5 mm, 0.6 mm. 0.7 mm. 0.8 mm. 0.9 mm or 1 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIGS. 3E to 3F) configured to receive the humidifier reservoir 5110. In some arrangements, the humidifier reservoir dock 5130 may comprise a locking feature such as a locking lever configured to retain the reservoir 5110 in the humidifier reservoir dock 5130.

Air Delivery Tube to Reservoir Dock Connection

FIGS. 5-1 to 5-19 show an integrated RPT device and humidifier 6000 and an air delivery tube 4170 including an interface arrangement according to an example of the present technology.

The integrated RPT device and humidifier 6000 includes a reservoir dock 6050 that is structured and arranged to receive a water reservoir (also referred to as a humidifier tub or a humidifier reservoir), e.g., see FIGS. 3C to 3F. In an example, the water reservoir may be removable and replaced with an outlet muffler, e.g., see FIGS. 3A and 3B described above. Thus, in an example, the integrated RPT device and humidifier 6000 may be used with or without humidification depending upon whether a water reservoir or an outlet muffler respectively is attached to the reservoir dock 6050.

As shown in FIGS. 5-1 to 5-3, an outlet port 6500 is provided to the dock outlet 6090 of the reservoir dock 6050 to pneumatically connect a water reservoir or outlet muffler to the air delivery tube 4170. As shown, the outlet port does not have to be horizontal, but can also be angled, say with respect to the base plane BP of the device (see FIG. 3F). The outlet port 6500 is configured to deliver pressurized air that has been humidified in the water reservoir, or that has passed through the outlet muffler, to the air delivery tube 4170. In an example, the outlet port 6500 may be removably coupled to the reservoir dock 6050 so that the outlet port 6500 can be disassembled for cleaning, sterilization and/or replacement, e.g., for multi-patient multi-use (MPMU) applications.

The outlet port 6500 comprises an outlet portion 6510 adapted to interface with the air delivery tube 4170 and an inlet portion (not shown) adapted to interface with the water reservoir or outlet muffler. The outlet portion 6510 includes an outlet tube 6512 and an outlet seal 6515 protruding towards the opening of the outlet tube 6512. In the illustrated example, the outlet seal 6515 comprises a bellows-type arrangement.

An electrical socket 6300 is provided to the dock outlet 6090 of the reservoir dock 6050 to electrically connect the reservoir dock 6050 to the air delivery tube 4170. As illustrated, the electrical socket 6300 comprises recessed contacts 6310 in communication with electrical power and electrical signalling within the reservoir dock 6050, e.g., the PCBA. In the illustrated example, the electrical socket 6300 is arranged generally superior and posterior to the outlet port 6500, when the integrated RPT device and humidifier 6000 is in an operational configuration.

Further, the dock outlet 6090 of the reservoir dock 6050 includes an annular side wall 6100 providing a socket or opening 6115 leading to the outlet port 6500. In the illustrated example, the annular side wall 6100 is arranged generally posterior to the outlet port 6500 and generally inferior to the electrical socket 6300. At least one locking pin 6200 is located on the annular side wall 6100 and protrudes into the opening 6115 (e.g., see FIG. 5-3). In one example, two diametrically opposing locking pins 6200 are included on the annular side wall 6100. As described below, the locking pins 6200 are arranged to at least one of: locate, guide and secure the air delivery tube 4170 to the reservoir dock 6050.

While described in the context of an RPT device with an integrated humidifier, in an alternative example, the RPT device may be designed without a humidifier with no separate humidification reservoir or respective outlet muffler in mind. In such example, the inlet portion of the outlet port 6500 would engage with the pneumatic block of the RPT device.

As shown in FIGS. 5-2 and 5-4, the air delivery tube 4170 includes a tube portion 4500 and a dock connector or cuff 4600 to connect the air delivery tube 4170 to the reservoir dock 6050. Whilst not shown, the tube 4170 also includes a patient interface connector or cuff to connect the air delivery tube 4170 to the patient interface 3000.

In the illustrated example, the cuff (dock connector) 4600 is structured and arranged to form a mechanical, electrical, and pneumatic connection with the reservoir dock 6050, i.e., with the locking pins 6200, electrical socket 6300, and outlet port 6500 provided to the dock outlet 6090 of the reservoir dock 6050. Since the reservoir dock 6050 is pneumatically and electrically coupled to the RPT device (including access to the generated airflow, a power supply and to the controller 5250), these connections between the air delivery tube 4170 and the reservoir dock 6050 not only locate and secure the air delivery tube 4170 to the reservoir dock 6050, but also provide electrical power, information and control signals to the heating element and transducers associated with the air delivery tube 4170, and allow pressurized gas that has been humidified in the water reservoir, or that has passed through the outlet muffler, to flow to the patient interface 3000.

As described below, during the engagement of the air delivery tube 4170 with the reservoir dock 6050, at least the electrical and pneumatic connections or interfaces are formed in series with at least two, independent user motions, e.g., the electrical connection is completed before the pneumatic connection or vice versa. That is, the air delivery tube 4170 and the reservoir dock 6050 are structured and arranged such that at least the electrical and pneumatic connections cannot be formed simultaneously.

As shown in FIGS. 5-2 and 5-4, the dock connector 4600 of the air delivery tube 4170 includes a cuff body 4610 and an electrical plug or tongue 4620, which in the illustrated example is provided to a superior side of the cuff body 4610. The electrical plug 4620 includes contacts 4625 (e.g., along superior and/or inferior sides of the plug) that, in use, are engaged with respective contacts 6310 provided to the electrical socket 6300 to form electrical connections with the reservoir dock 6050 to provide electrical power and/or control signal transmission. In an example, the contacts 4625 of the electrical plug 4620 may be joined to respective wires running along the air delivery tube 4170, e.g., configured to heat air in the air delivery tube and/or transmit signal from one or more transducers (e.g., temperature sensor, flow sensor).

Further, the dock connector 4600 includes a tubular locking collar 4650 that is rotatably and telescopically mounted to the cuff body 4610. This arrangement allows the locking collar 4650 to both rotate and slide axially relative to the cuff body 4610. As shown in FIGS. 5-12 and 5-13, the locking collar includes a slot or cut-out 4652 on a superior side thereof to accommodate the electrical plug 4620 during rotating and/or sliding movement of the locking collar 4650 relative to the cuff body 4610. Moreover, each of two diametrically opposing sides of the locking collar 4650 includes a guide slot 4655 configured to receive a respective locking pin 6200 on each side of the opening 6115 leading to the outlet port 6500. As illustrated, in this example, each guide slot 4655 includes a generally horizontal, guiding section 4655a, associated with an axial movement of the dock connector 4600 with respect to the reservoir dock outlet 6090, leading to a locking section 4655b that slopes away from the guiding section 4655a, this later locking section 4655b being associated with a rotational movement of the dock connector 4600 with respect to the reservoir dock outlet 6090.

FIGS. 5-5 to 5-11 illustrate a number of sequential steps in the engagement between the dock connector 4600 of the air delivery tube 4170 and the dock outlet 6090 of the reservoir dock 6050, according to an example of the present technology. As shown in FIG. 5-5, the dock connector 4600 is oriented to align the electrical plug 4620 with the electrical socket 6300 provided to the dock outlet 6090, align the cuff body 4610 and locking collar 4650 with the opening 6115 leading to the outlet port 6500, and align the open end of each of the guide slots 4655 with respective locking pins 6200 within the opening 6115. As shown in FIG. 5-6, the dock connector 4600 is then pushed towards the reservoir dock 6050 so that the free end of the cuff body 4610 enters into the opening 6115, and the locking pins 6200 within the opening 6115 enter into the open end of respective guide slots 4655 of the locking collar 4650. Moreover, the electrical plug 4620 of the dock connector 4600 engages within the electrical socket 6300 so that the contacts 4625 of the electrical plug 4620 engage with contacts 6310 provided to the electrical socket 6300 which forms the electrical and control signal connections with the reservoir dock 6050. Accordingly, an operational electrical connection is effected during this initial insertion, but not a pneumatic connection as shown in FIG. 5-6.

In a second step of the engagement process, the dock connector 4600 is pushed further towards the reservoir dock 6050 so that the locking pins 6200 engage and slide within the generally horizontal, guiding section 4655a of respective guide slots 4655 until the locking pins 6200 reach the locking section 4655b of respective guide slots 4655, as shown in FIG. 5-7. As illustrated, the electrical plug 4620 of the dock connector 4600 maintains an electrical connection with the electrical socket 6300, and a pneumatic connection is still not effected.

The locking collar 4650 of the dock connector 4600 is subsequently rotated in a clockwise direction in order to axially lock the dock connector 4600 to the reservoir dock 6050 and form the pneumatic connection with the reservoir dock 6050. As shown in FIG. 5-8, as the locking collar 4650 is rotated in a clockwise direction, the locking pins 6200 engage and slide into the locking section 4655b of respective guide slots 4655, which allows the locking collar 4650 to simultaneously move axially relative to the cuff body 4610. Such axially movement starts to bridge the gap 4651 between the locking collar 4650 and the cuff body 4610 at the rear of the dock connector 4600. Further rotation of the locking collar 4650 closes the gap so that the end wall of the locking collar 4650 abuts the adjacent end of the cuff body 4610, e.g., see FIG. 5-9. The locking collar 4650 is further rotated until the locking pins 6200 reach the end of respective guide slots 4655 (e.g., see FIG. 5-10) and/or a dedicated locking feature (e.g., 4656 or 4657 in FIGS. 5-14 and 5-15) within respective guide slots to lock the locking collar 4650 in an operative position (see FIG. 5-11). FIGS. 5-12 and 5-13 are top views of the dock connector 4600 showing the locking collar 4650 in an unlocked position (FIG. 5-12) and a locked position (FIG. 5-13), i.e., showing the locking collar 4650 being rotated and axially slid relative to the cuff body 4610 from the unlocked to locked position. Such further rotation and axial movement of the locking collar 4650 also pushes the cuff body 4610 further into the opening 6115 and the electrical plug 4620 further into the electrical socket 6300 (due to the above noted abutment of the locking collar 4650 with the cuff body 4610), which brings the free end of the cuff body 4610 into a sealed engagement with the outlet seal 6515 of the outlet port 6500 to form the operational pneumatic connection between the dock connector 4600 and the reservoir dock 6050 (see FIGS. 5-10 and 5-11). Moreover, the arrangement of the locking pins 6200 within the locking section 4655b of respective guide slots 4655 axially locks the locking collar 4650 and hence the dock connector 4600 to the reservoir dock 6050 in an operative position in which both electrical and pneumatic connections are formed (see FIG. 5-11).

As noted above, each of the guide slots 4655 may include a dedicated locking feature to lock the locking collar 4650 and hence the dock connector 4600 in the operative position. For example, as shown in FIG. 5-14, the locking section 4655b of each of the guide slots 4655 may include one or two bumps 4656 (on one or both sides of each guide slot) to lock the pin 6200 once it passes thereby. In another example, as shown in FIG. 5-15, the locking section 4655b of each of the guide slots 4655 may include a recess 4657 (e.g., on an inner side of each guide slot) to receive the pin 6200 therein. Alternatively, locking may be effected by the friction between the pin 6200 and a side (e.g., an inner side) of each guide slot 4655 against which the pin 6200 is progressively pushed against during rotation of the locking collar 4650. In another example (not shown), the rotation of the cuff may force the guiding pin into a progressively narrowing guide slot 4655, creating a frictional locking interference fit with both sides of the guide slot. In an example, the frictional locking mechanisms may provide tactile feedback to the user to confirm locking/unlocking of the air delivery tube.

In this example, connection of the dock connector 4600 with the reservoir dock 6050 is configured so that the electrical connection is completed prior to the pneumatic and mechanical connections. In another example, the pneumatic and mechanical connections may be formed simultaneously when the locking collar 4650 is rotated into the locked position, by bringing the free end of the cuff body 4610 into a sealed engagement with the outlet seal 6515 of the outlet port 6500 to form the operational pneumatic connection between the dock connector 4600 and the reservoir dock 6050 at the very beginning of the engagement, during the process of engaging the electrical connections of the dock connector 4600 and the reservoir dock 6050. Also, each connection or interface functions independently of the other interfaces, i.e., the pneumatic interface functions regardless of whether the electrical interface functions.

To disconnect the air delivery conduit 4170 from the reservoir dock 6050, the locking collar 4650 can be rotated in a counter-clockwise direction from the locked position into the unlocked position in which the locking pins 6200 slide out of the locking section 4655b and into the generally horizontal, guiding section 4655a of respective guide slots 4655 (see FIGS. 5-16 and 5-17). This allows the locking collar 4650 and hence the dock connector 4600 to be pulled outwardly away from the reservoir dock 6050 for disconnection (see FIGS. 5-18 and 5-19). In an example, an initial nudge may be needed during the rotational movement, in order to disengage the locking engagement of the locking elements (e.g., 4656 or 4657) from respective locking pins 6200.

It is noted that connection and disconnection of the dock connector 4600 with the reservoir dock 6050 may be performed with a single hand of the user. Also, connection and disconnection each require two independent user motions (e.g., in mutually transverse planes), i.e., whilst the initial push immediately effects an operational electrical connection, only after a subsequent rotation of the locking collar 4650 is an operational pneumatic connection effected.

FIGS. 6-1 to 6-14 show an integrated RPT device and humidifier 6000 and an air delivery tube 4170 including an interface arrangement according to another example of the present technology. Similar to the above example, at least the electrical and pneumatic connections or interfaces are formed in series with at least two, independent user motions, e.g., the electrical connection is completed before the pneumatic connection.

As shown in FIGS. 6-2 and 6-3, an outlet port 6500 is provided to the dock outlet 6090 of the reservoir dock 6050 to pneumatically connect a water reservoir or outlet muffler to the air delivery tube 4170. As described above, the outlet port 6500 (which may be removably coupled to the reservoir dock 6050 for MPMU applications) comprises an outlet seal 6515 adapted to interface with the air delivery tube 4170.

Also, the dock outlet 6090 of the reservoir dock 6050 includes a side wall 6100 that provides a socket or opening 6115 leading to the outlet port 6500. In the illustrated example, the opening 6115 is arranged generally posterior (with reference to the flow path) to the outlet port 6500.

Further, in this example, a locking and contact assembly 6600 is provided to a superior side of the opening 6115. The locking and contact assembly 6600 includes a locking lever or latch 6650 and one or more contacts 6310 in communication with electrical power and electrical signalling within the reservoir dock 6050, e.g., the PCBA. In an example, each of the contacts 6310 comprises a spring loaded pin configured to resiliently deflect during engagement with the dock connector 4600 of the air delivery tube to maintain contact with respective contacts of the dock connector 4600.

The locking lever 6650 is pivotally connected to the side wall 6100 for pivotal movement about a pivot axis PA between a locked position and an unlocked position. The locking lever 6650 includes a push button 6652 at one end of the locking lever 6650 and a lock arm 6654 at the other end of the locking lever 6650. Also, the locking lever 6650 includes a stop arm 6656 between the push button 6652 and lock arm 6654, e.g., arranged at the pivot axis PA of the locking lever 6650. In the illustrated example, a spring 6660 is arranged at the locking end of the locking lever 6650 to bias the locking lever 6650 to the locked position.

As shown in FIGS. 6-2 and 6-4, the dock connector 4600 of the air delivery tube 4170 includes a cuff body 4610 and an electrical pad 4621 protruding from a superior side of the cuff body 4610. The electrical pad 4621 includes one or more contacts 4625 that, in use, are engaged with contacts 6310 provided to the locking and contact assembly 6600 to form electrical connections with the reservoir dock 6050 to provide electrical power and/or control signal transmission. In an example, the contacts 4625 of the electrical pad 4621 may be joined to respective wires running along the air delivery tube 4170, e.g., configured to heat air in the air delivery tube and/or transmit signal from one or more transducers (e.g., temperature sensor, flow sensor).

FIGS. 6-5 to 6-10 illustrate connection of the dock connector 4600 of the air delivery tube 4170 to the dock outlet 6090 of the reservoir dock 6050 according to an example of the present technology. As shown in FIG. 6-5, the dock connector 4600 is oriented to align the electrical pad 4621 with the locking and contact assembly 6600 provided to the dock outlet 6090 and align the cuff body 4610 with the opening 6115 leading to the outlet port 6500. As illustrated, the locking lever 6650 is biased to the locked position so that the lock arm 6654 is arranged to engage the front face of the electrical pad 4621, thereby preventing insertion of the dock connector 4600 into the dock outlet 6090 until a user manually depresses the push button 6652. As shown in FIG. 6-6, manual depression of the push button 6652 pivots the locking lever 6650 into the unlocked position in which the lock arm 6654 is raised upwardly above the front face of the electrical pad 4621, which allows the electrical pad 4621 and hence the cuff body 4610 to be pushed into the opening 6115 leading to the outlet port 6500.

FIGS. 6-7 and 6-8 show the dock connector 4600 being pushed into the opening 6115 leading to the outlet port 6500. As illustrated, such insertion of the dock connector 4600 requires two user actions and two hands, i.e., (1) holding the push button 6652 in the depressed position with one hand to maintain the locking lever 6650 in the unlocked position and (2) pushing the dock connector 4600 with the other hand into the opening 6115.

As shown in FIG. 6-8, the dock connector 4600 is pushed further into the opening 6115 until the electrical pad 4621 abuts the stop arm 6656 of the locking lever 6650 which acts as a stop to prevent further insertion of the dock connector 4600, thereby preventing the free end of the cuff body 4610 from engaging with the outlet seal 6515 of the outlet port 6500 to form a pneumatic connection. Moreover, at this point, the one or more contacts 4625 of the electrical pad 4621 are arranged to engage with the contacts 6310 of the locking and contact assembly 6600 which forms the electrical and control signal connections with the reservoir dock 6050. Accordingly, an electrical connection is effected during insertion with the locking lever 6650 in the unlocked position, but not a pneumatic connection as shown in FIG. 6-8.

Once the electrical pad 4621 of the dock connector 4600 passes beyond the lock arm 6654 and into engagement with the stop arm 6656, the push button 6652 can be manually released, thereby allowing the locking lever 6650 to resiliently return to the locked position which allows the lock arm 6654 to lower down or drop behind the rear face of the electrical pad 4621 to axially lock the dock connector 4600 in an operative position, as shown in FIG. 6-9. As illustrated, the contacts 4625 of the electrical pad 4621 maintain an electrical connection with the contacts 6310 of the locking and contact assembly 6600. Moreover, pivotal movement of the locking lever 6650 back into the locked position moves the stop arm 6656 rearwardly to allow the free end of the cuff body 4610 to engage the outlet seal 6515 of the outlet port 6500 to form the pneumatic connection between the dock connector 4600 and the reservoir dock 6050 (see FIG. 6-9). FIG. 6-10 shows the dock connector 4600 connected to the reservoir dock 6050 in an operative position in which both electrical and pneumatic connections are formed.

In this example, connection of the dock connector 4600 with the reservoir dock 6050 is configured so that the electrical connection is completed prior to completion of the pneumatic and mechanical connections. In an example, the pneumatic and mechanical connections may be formed simultaneously when the push button 6652 of the locking lever 6650 is manually released back into the locked position. In an alternative example, the pneumatic connection may be formed when the locking lever 6650 is in the unlocked position, e.g., stop arm 6656 of the locking lever 6650 not provided so as to allow the free end of the cuff body 4610 to engage with the outlet seal 6515 of the outlet port 6500 to form the pneumatic connection when the locking lever 6650 is in the unlocked position. That is, the pneumatic connection may be formed before the locking lever is pivoted down (i.e. the unlocked position) or after the locking lever is pivoted down (i.e., the locked position). Also, each connection or interface functions independently of the other interfaces, i.e., the pneumatic interface functions regardless of whether the electrical interface functions.

FIGS. 6-11 to 6-14 illustrate disconnection of the dock connector 4600 of the air delivery tube 4170 from the dock outlet 6090 of the reservoir dock 6050 according to an example of the present technology. To disconnect the air delivery conduit 4170 from the reservoir dock 6050, the push button 6652 of the locking lever 6650 can be manually depressed to pivot the locking lever 6650 into the unlocked position (see FIG. 6-11). This raises the lock arm 6654 upwardly above the rear face of the electrical pad 4621, which will allow the electrical pad 4621 and hence the cuff body 4610 to be pulled out of the opening 6115. Further, the pivotal movement of the locking lever 6650 moves the stop arm 6656 forwardly until the stop arm 6656 abuts the electrical pad 4621, which disengages the free end of the cuff body 4610 from the outlet seal 6515 of the outlet port 6500 and thereby terminates the pneumatic connection between the dock connector 4600 and the reservoir dock 6050. As illustrated, the contacts 4625 of the electrical pad 4621 maintain an electrical connection with the contacts 6310 of the locking and contact assembly 6600.

FIG. 6-12 shows the dock connector 4600 being pulled with one hand from the opening, while the user holds the push button 6652 in the depressed position with the other hand to maintain the locking lever 6650 in the unlocked position. FIG. 6-13 shows the dock connector 4600 released from electrical and pneumatic connections with the reservoir dock 6050, and the push button 6652 of the locking lever 6650 being manually released to allow the locking lever 6650 to resiliently lower down back into the locked position. FIG. 6-14 shows the dock connector 4600 completely pulled away from and disconnected from the reservoir dock 6050.

In the above example, connection and disconnection of the dock connector 4600 with the reservoir dock 6050 is performed with two hands of the user. Also, connection and disconnection each requires two independent user motions, i.e., pushing the locking lever 6650 (in a radial direction with respect to the dock connector 4600) and pushing the dock connector 4600 (in a substantially axial direction with respect to the dock connector 4600) for connection; and pushing the locking lever 6650 and pulling the dock connector 4600 for disconnection. As a result, the electrical and pneumatic interfaces are made in series and not simultaneously. The two independent user motions in this case are along two substantially transverse directions in two substantially transverse planes. In an alternative example, the two independent user movements may be in one plane, i.e., pushing the locking lever 6650 and pushing the dock connector 4600 may include movements in the same plane. When the movements are linear, it could be said that the locking lever 6650 and the dock connector 4600 are pushed along axes in the same plane.

FIGS. 7-1 to 7-7 show an air delivery tube 4170 and a water reservoir 6400 including an interface arrangement according to another example of the present technology. Similar to the above examples, at least the electrical and pneumatic connections or interfaces are formed in series with at least two, independent user motions, e.g., the electrical connection is completed before the pneumatic connection or vice versa.

In this example, the dock connector 4600 of the air delivery tube 4170 is structured and arranged to form an electrical connection with the reservoir dock and to form a direct pneumatic connection with the water reservoir 6400 so that the pressurized flow of air that has been humidified in the water reservoir 6400 is delivered directly from the water reservoir 6400 to the air delivery tube 4170. Moreover, the dock connector 4600 of the air delivery tube 4170 is structured and arranged to form a mechanical connection with the water reservoir 6400 to lock the air delivery tube 4170 in an operative position.

The dock connector 4600 of the air delivery tube 4170 includes a cuff body 4610 and one or more contacts 4625 provided to a superior side of the cuff body 4610, with reference to the system's operational orientation. The one or more contacts 4625, in use, are adapted to engage with contacts provided to the reservoir dock to provide electrical power and/or control signal transmission. In an example, the contacts 4625 may be joined to respective wires running along the air delivery tube 4170, e.g., configured to heat air in the air delivery tube and/or transmit signal from one or more transducers (e.g., temperature sensor, flow sensor).

The dock connector 4600 includes a pair of resilient, pinch arms 4615, i.e., cantilevered spring arms or pinch buttons. In an example, each of the spring or pinch arms 4615 may include a barbed end or tab structured to, when the connector is inserted and the tabs are released, provide a snap-fit connection with the reservoir dock.

The dock connector 4600 includes an inlet portion 4630 adapted to interface with the water reservoir 6400. The inlet portion 4630 includes an inlet tube 4632 and a flange 4635 arranged at a free end of the inlet tube 4632. In the illustrated example, the inlet portion 4630 is curved along its length such that an inlet opening of the inlet portion 4630 defines an axis IA (see FIGS. 7-3 and 7-5) that is substantially angled with respect to an insertion axis along which the dock connector 4600 needs to be moved in order to engage with the water reservoir 6400 (and may be substantially perpendicular to a longitudinal axis of the cuff body 4610). The angle can vary between about 45 to about 90 degrees, the latter being illustrated in FIG. 7-1 to FIG. 7-3. When the dock connector 4600 is coupled to the reservoir dock, the flange 4635 and contact surface 4636 thereof protrudes into the cavity of the reservoir dock to allow a direct engagement with the outlet 6450 of the water reservoir 6400, without the need of an intermediate coupling elements.

Further, the inlet portion 4630 includes spaced-apart and parallel side walls 4640 protruding from an exterior surface of the inlet tube 4632. As illustrated, the side walls 4640 form an elongated recess 4642 with its elongated open end oriented in the same direction as the contact surface 4636 of the inlet tube 4632. As described below, the recess 4642 is configured and arranged to receive a locking protrusion 6460 protruding from the water reservoir 6400, which interface locks the air delivery tube 4170 to the reservoir dock in an operative position. In an alternative example, the locking protrusion may protrude from an engagement port associated with the water reservoir dock, which interface locks the air delivery tube to reservoir dock in an operative position. Also, as described above, the water reservoir may be removable and replaceable with an outlet muffler, e.g., see FIGS. 3A and 3B. In this regard, according to an example, the locking protrusion may protrude from an outlet port associated with the outlet muffler, which interface locks the air delivery tube to reservoir dock in an operative position.

In this example, the above locking arrangement may define a pneumatic connection that is dependent on the air delivery tube 4170 being connected to the reservoir dock before connection of the water reservoir 6400 to the reservoir dock is effected. In this example, if the water reservoir 6400 is first connected to the reservoir dock, the air delivery tube 4170 may not be able to be fully inserted into the reservoir dock to form a pneumatic connection with the water reservoir 6400, as a leading one of the side walls 4640 may abut or engage the locking protrusion 6460 on the water reservoir 6400.

Thus, the air delivery tube 4170 must be first connected to the reservoir dock 6050, e.g., by inserting the dock connector 4600 into the respective dock opening until it reaches an operative position. In an example, the spring or pinch arms 4615 of the dock connector 4600 may releasably secure the dock connector 4600 in the operative position. Moreover, such connection allows the contacts 4625 of the dock connector 4600 to form electrical and control signal connections with the reservoir dock.

Following connection of the air delivery tube 4170 to the reservoir dock, which also forms the electrical connection, the water reservoir 6400 can be inserted into the cavity of the reservoir dock until the outlet 6450 of the water reservoir 6400 engages the contact surface 4636 at the inlet portion 4630 of the dock connector 4600 to form the direct pneumatic connection. Moreover, the locking protrusion 6460 on the water reservoir 6400 engages within the recess 4642 at the inlet portion 4630 of the dock connector 4600 which engagement prevents withdrawal or removal of the air delivery tube 4170 from the reservoir dock.

In order to remove the air delivery tube 4170 from the reservoir dock, the water reservoir 6400 must first be removed from the reservoir dock in order to release the locking protrusion 6460 from the recess 4642. Other locking arrangements between the inserted air delivery tube 4170 and the reservoir dock, not making use of locking side walls 4640 (i.e., using a locking interference fit or a locking arrangement similar to the latch-type or locking button type locking arrangements that are to be described in relation to FIGS. 8 and 9 respectively), may allow inserting and removing each of the air delivery tube 4170 and the water reservoir 6400 independently from each other.

FIGS. 8-1 to 8-4 show an integrated RPT device and humidifier 6000 and an air delivery tube 4170 including an interface arrangement according to another example of the present technology. In this example, at least the electrical and pneumatic connections or interfaces are formed in series with at least two, independent user motions, e.g., the pneumatic connection is completed before the electrical connection.

As shown in FIG. 8-3, the integrated RPT device and humidifier 6000 includes a reservoir dock 6050 that is structured and arranged to receive a water reservoir 6400. In an example, the water reservoir may be removable and replaced with an outlet muffler, e.g., see FIGS. 3A and 3B described above. An outlet port (not shown) is provided to the dock outlet 6090 of the reservoir dock 6050 to pneumatically connect a water reservoir or outlet muffler to the air delivery tube 4170.

In this example, a pivotable locking latch 6700 is provided to a superior, with respect to the operational orientation of the device, side of the dock outlet 6090 of the reservoir dock 6050. The locking latch 6700 is structured and arranged to releasably engage the air delivery tube 4170 to retain the air delivery tube 4170 in an operative position.

As illustrated, one end of the pivotable locking latch 6700 is pivotally coupled to a superior side of the dock outlet 6090 of the reservoir dock 6050 and the opposite end includes a retaining protrusion 6710. In use, the locking latch 6700 may be rotated between (1) an unlocked position (e.g., see FIGS. 8-1 and 8-2) to allow insertion/removal of the air delivery tube 4170 from the dock 6050, and (2) a locked position (e.g., see FIGS. 8-3 and 8-4) to releasably lock or retain the air delivery tube 4170 to the dock 6050 in an operative position.

When the dock connector 4600 of the air delivery tube 4170 is inserted into the dock outlet 6090 and the dock connector 4600 forms a pneumatic connection with the outlet port provided to the dock outlet 6090, the locking latch 6700 can be rotated to the locked position to allow the retaining protrusion 6710 thereof to clip down over and behind an edge or catch 4611 on a superior side of the dock connector 4600 (e.g., with a snap-fit) to effectively lock the air delivery tube 4170 in the operative position.

Moreover, the pivotable locking latch 6700 includes one or more contacts 6310 in communication with electrical power and electrical signalling within the reservoir dock 6050, e.g., the PCBA. When the locking latch 6700 is pivoted/rotated to the locked position, the one or more contacts 6310 are structured and arranged to engage with one or more contacts 4625 on a superior side of the dock connector 4600 to form the electrical and control signal connections. In an example, each of the contacts 6310 may comprise a spring arm configured to resiliently defect during engagement with the dock connector 4600 to maintain contact with respective contacts 4625 of the dock connector 4600.

In this example, connection of the dock connector 4600 with the reservoir dock 6050 is configured so that the pneumatic connection is completed at the moment of insertion of the air delivery tube 4170 into the dock outlet 6090 and before the effecting of the electrical connection and the mechanical locking. In another example, the pivoting latch may be arranged to push the air delivery tube 4170 into a sealing configuration with the dock outlet 6090, ensuring that the electrical, pneumatic and mechanical connections are formed simultaneously when the locking latch 6700 is rotated into the locked position. Also, each connection or interface may function independently of the other interfaces, i.e., the pneumatic interface functions regardless of whether the electrical interface functions.

The locking latch 6700 can be rotated to the unlocked position to allow the latch 6700 to disengage from the air delivery tube 4170 and allow the retaining protrusion 6710 thereof to raise from behind the edge or catch 4611 on the dock connector 4600 to allow removal of the air delivery tube 4170.

It is noted that connection and disconnection of the dock connector 4600 with the reservoir dock 6050 may be performed with one or two hands of the user. Also, connection and disconnection each require two independent user motions, i.e., pushing the dock connector 4600 and pivoting the latch 6700 for connection, and pivoting the latch 6700 and pulling the dock connector 4600 for disconnection, to ensure that electrical and pneumatic interfaces are made in series and not simultaneously. The second independent motion, i.e., the pivoting of latch 6700, is effected around an axis that is substantially transverse to the axis along which the first (linear) motion is effected. The pivotal axis and linear motion axis may extend in two substantially transverse planes, or may extend in one plane. The linear motion axis also happens to coincide with, or be parallel to, the axis of the dock outlet 6090 and the longitudinal axis of the air delivery tube 4170.

FIGS. 9-1 to 11-7 show an integrated RPT device and humidifier 6000 and an air delivery tube 4170 including an interface arrangement according to another example of the present technology. In this example, at least the electrical and pneumatic connections or interfaces are formed in series with at least two, independent user motions, e.g., the electrical connection is completed before the pneumatic connection.

As shown in FIGS. 9-1 and 9-3, the integrated RPT device and humidifier 6000 includes a reservoir dock 6050 that is structured and arranged to receive a water reservoir or an outlet muffler, e.g., see FIGS. 3A to 3F. As illustrated, an outlet port 6500 is provided to the dock outlet 6090 of the reservoir dock 6050 to pneumatically connect a water reservoir or outlet muffler to the air delivery tube 4170. In an example, the outlet port 6500 may be removably coupled to the reservoir dock 6050 for MPMU applications. The outlet port 6500 comprises an outlet portion or outlet tube 6510 adapted to interface with the air delivery tube 4170 and an inlet portion (not shown) adapted to interface with the water reservoir or outlet muffler.

The dock outlet 6090 of the reservoir dock 6050 includes a socket or opening 6115 leading to the outlet port 6500. A pad receiving recess 6117 is provided to a superior (with respect to the operational orientation of the device, side of the opening 6115, and a pin receiving recess 6119 is provided to each of lateral sides of the opening 6115 (e.g., see FIGS. 9-1 and 10-5). A superior side of the pad receiving recess 6117 includes one or more contacts 6310 (e.g., see FIG. 10-4) in communication with electrical power and electrical signalling within the reservoir dock 6050, e.g., the PCBA. In an example, each of the contacts 6310 may comprise a spring arm configured to resiliently defect during engagement with the dock connector 4600 of the air delivery tube 4170 to maintain contact with respective contacts 4625 of the dock connector 4600. As described below, the pad receiving recess 6117 is arranged to at least partially locate and guide the air delivery tube 4170 to the one or more contacts 6310, and the pin receiving recesses 6119 are arranged to at least partially locate and guide the air delivery tube 4170 to a location where the tube may engage with a locking button or latch 6800.

The locking button or latch 6800 is slidably coupled to the reservoir dock 6050 adjacent the dock outlet 6090 for slidable movement between (1) an unlocked position (e.g., see FIGS. 9-1 to 9-3 and 10-1 to 10-7) to allow insertion/removal of the air delivery tube 4170 from the dock 6050 and (2) a locked position (e.g., see FIGS. 11-1 to 11-7) to releasably lock or retain the air delivery tube 4170 to the dock 6050 in an operative position.

As shown in FIGS. 9-5 and 9-6, the locking button 6800 includes a top wall 6810, outer side walls 6820 extending from respective sides of the top wall 6810, and inner side walls 6830 extending from the top wall 6810 and spaced inwardly from respective outer side walls 6820.

As shown in FIG. 9-5, the inwardly facing surface of each inner side wall 6830 includes a guide slot 6840 configured to receive a respective locking pin 4670 on each side of the dock connector 4600. As illustrated, each guide slot 6840 includes a generally horizontal, guiding section 6840G, a transition section 6840T that slopes upwardly and away from the guiding section 6840G, and a generally vertical, locking section 6840L.

Also, in this example, a posterior (with respect to the direction of the airflow) edge of each inner side wall 6830 includes a retaining protrusion 6832 configured and arranged to releasably retain the locking button 6800 in each of the unlocked and locked positions. In addition, an anterior edge of each inner side wall 6830 includes a stop protrusion 6834 configured and arranged to act as a stop and prevent at least an inadvertent removal of the locking button 6800 from the dock 6050, e.g., permanently retain the locking button 6800 to the dock 6050.

As best shown in FIGS. 9-1 and 10-5, walls surrounding the dock outlet 6090 of the reservoir dock 6050 form spaced-apart recesses 6065 adapted to receive respective ones of the inner side walls 6830 of the locking button 6800. As illustrated, the top wall 6810 and outer side walls 6820 are arranged outside the walls surrounding the dock outlet 6090 of the reservoir dock 6050, e.g., to allow manual manipulation of the locking button 6800. A front wall of reservoir dock 6050, in which the dock outlet 6090 is formed, provides an upper edge 6067 and a lower opening 6068 which interact with the retaining protrusion 6832 of the locking button 6800 in the unlocked and locked positions as described below (e.g., see FIGS. 10-7 and 11-7). Also, an inner wall of the reservoir dock 6050 provides an edge 6069 which interacts with the stop protrusion 6834 to prevent removal of the locking button 6800 (e.g., see FIG. 10-7).

As shown in FIG. 9-4, the dock connector 4600 of the air delivery tube 4170 includes an electrical pad 4621 protruding from a superior side of the dock connector 4600. The electrical pad 4621 includes the one or more contacts 4625 that, in use, are engaged with contacts 6310 provided to the reservoir dock 6050 for electrical power and/or control signal transmission. In an example, the contacts 4625 of the electrical pad 4621 may be joined to respective wires running along the air delivery tube 4170, e.g., configured to heat air in the air delivery tube and/or transmit signal from one or more transducers (e.g., temperature sensor, flow sensor).

As noted above, each side of the dock connector 4600 includes a locking pin 4670. Also, dock connector 4600 includes a circumferential lip seal 4675 that protrudes into the opening of the dock connector 4600. The circumferential lip seal 4675, in its relaxed, undeformed shape, provides an internal diameter that is smaller than the external diameter of the outlet tube 6510 of the outlet port 6500. In use, the circumferential lip seal 4675 is structured to resiliently deform upon engagement with the outlet tube 6510 so as to provide a pneumatic connection with the outlet port 6500, e.g., circumferential lip seal 4675 forms a gas tight seal against the exterior surface of the outlet tube 6510.

Engagement of the dock connector 4600 of the air delivery tube 4170 with the reservoir dock 6050 will now be described in more detail. As shown in FIGS. 9-1 to 9-3, the dock connector 4600 is oriented to align its locking pins 4670 with respective pin receiving recesses 6119 and align its electrical pad 4621 with the pad receiving recess 6117 along the opening 6115 leading to the outlet port 6500. As illustrated, the locking button 6800 is slidably moved or pulled upwardly relative to the reservoir dock 6050 and into the unlocked position, which allows the generally horizontal, guiding section 6840G of each guide slot 6840 to align with respective pin receiving recesses 6119 along the opening 6115. As shown in FIG. 10-7, the locking button 6800 is maintained in the unlocked position by the retaining protrusion 6832 which engages over the top of the upper edge 6067, e.g., with a snap-fit. Further, as shown in FIG. 10-7, the stop protrusion 6834 is configured to engage the edge 6069 which acts as a stop for the unlocked position and prevents removal of the locking button 6800 from the dock 6050.

As shown in FIGS. 10-1 to 10-7, the dock connector 4600 is pushed towards the reservoir dock 6050 so that the locking pins 4670 slide through respective pin receiving recesses 6119 and into respective guiding sections 6840G of the locking button 6800 until the locking pins 4670 reach the end of respective guiding sections 6840G which provides a hard stop for further insertion (e.g., see FIGS. 10-6 and 10-7). At the same time, the electrical pad 4621 slides into the pad receiving recess 6117, which allows the one or more contacts 4625 of the electrical pad 4621 to engage with the contacts 6310 in communication with electrical power and electrical signalling within the reservoir dock 6050 (e.g., see FIGS. 10-3 and 10-4). Moreover, dock connector 4600 is arranged within the opening 6115 so that the circumferential lip seal 4675 is positioned adjacent to the free end of the outlet tube 6510 of the outlet port 6500 (e.g., see FIG. 10-4). Accordingly, only an electrical connection is effected during insertion when the locking button 6800 is in the unlocked position, but not a pneumatic connection.

As shown in FIGS. 11-1 to 11-7, the locking button 6800 is slidably moved or pushed downwardly relative to the reservoir dock 6050 to the locked position in order to axially lock the dock connector 4600 to the reservoir dock 6050 and form the pneumatic connection with the reservoir dock 6050. As the locking button 6800 is moved into the locked position, the locking pins 4670 are slid through respective transition sections 6840T of the locking button 6800 until the locking pins 4670 reach respective generally vertical, locking sections 6840L (e.g., see FIGS. 11-6 and 11-7). This axially moves the locking pins 4670 and hence the dock connector 4600 further into the opening 6115, which allows the circumferential lip seal 4675 to engage and resiliently deform against the exterior surface of the outlet tube 6510 of the outlet port 6500 to form an operational pneumatic connection between the dock connector 4600 and the reservoir dock 6050 (e.g., see FIGS. 11-3 and 11-4). Moreover, the arrangement of the locking pins 4670 within the locking section 6840L of respective guide slots 6840 axially locks the dock connector 4600 to the reservoir dock 6050 in an operative position in which both electrical and pneumatic connections are formed.

As shown in FIG. 10-7, the locking button 6800 is maintained in the locked position by the retaining protrusion 6832 which engages within the lower opening 6068, e.g., with a snap-fit.

In this example, connection of the dock connector 4600 with the reservoir dock 6050 is configured so that the electrical connection is completed prior to the pneumatic and mechanical connections. The movements that effect the electrical and the pneumatic connections are in a substantially transverse direction to each other. In particular, the first movement is in a horizontal direction along the axis of the dock connector 4600, i.e., this is the movement that brings the dock connector 4600 towards and into the reservoir dock 6050. The second movement is the depressing of the locking button 6800, which is in a vertical direction substantially transverse to that of the first movement in the horizontal direction. In another example, the pneumatic and mechanical connections may be formed simultaneously when the locking button 6800 is moved into the locked position. Also, each connection or interface functions independently of the other interfaces, i.e., the pneumatic interface functions regardless of whether the electrical interface functions.

To disconnect the air delivery conduit 4170 from the reservoir dock 6050, the locking button 6800 can be slidably moved or pulled upwardly to the unlocked position, which slides the locking pins 4670 of the dock connector 4600 out of respective locking sections 6840L and into respective guiding sections 6840G of the locking button 6800. This allows the dock connector 4600 to be pulled outwardly away from the reservoir dock 6050 for disconnection.

FIGS. 12-1 to 12-7 show an integrated RPT device and humidifier 6000 and an air delivery tube 4170 including an interface arrangement according to another example of the present technology. In this example, the electrical, pneumatic, and mechanical connections may be formed substantially simultaneously.

In this example, an intermediate component 6900 is provided to the dock outlet 6090 of the reservoir dock 6050 to electrically, pneumatically, and mechanically connect the air delivery tube 4170 to the reservoir dock 6050. In the illustrated example, the intermediate component 6900 is removably coupled to the reservoir dock 6050 so that the intermediate component 6900 can be disassembled for cleaning, sterilization and/or replacement, e.g., for MPMU applications.

The intermediate component 6900 comprises an inlet end 6910 adapted to interface with, and receive humidified airflow from, the water reservoir or outlet muffler, and an outlet end 6920 adapted to interface with, and pass on the airflow to, the air delivery tube 4170. In the illustrated example, the inlet end 6910 is arranged at an angle to the outlet end 6920, e.g., the axis of the inlet end is arranged at about 900 with respect to the axis of the outlet end. However, it should be appreciated that other suitable angles are possible, e.g., angles larger than 90 degrees may be preferable from a point of view of flow dynamics.

In the illustrated example, the inlet end 6910 provides a contact surface 6912 surrounding the opening at the inlet end 6910 structured to engage the outlet of the water reservoir or outlet muffler.

In the illustrated example, the outlet end 6920 includes an outlet tube 6922 and an annular side wall 6924 that surrounds the outlet tube 6922. The outlet tube 6922 and the annular side wall 6924 cooperate to form a channel 6925 for receiving the air delivery tube 4170. A retaining protrusion 6930 projects radially outwardly from a superior side of the annular side wall 6924. In some cases, the annular side wall 6924 can be part of the reservoir dock 6050, instead of the intermediate component 6900.

Also, as best shown in FIGS. 12-3 to 12-5, a contact assembly 6940 is provided to a superior side of the intermediate component 6900 to electrically connect the reservoir dock 6050 to the air delivery tube 4170. As illustrated, the contact assembly 6940 includes a support member 6942 and a plurality of contacts 6945 supported by the support member 6942. As best shown in FIGS. 12-4 and 12-7, each of the contacts 6945 includes: a first end portion 6946 adapted to engage with respective contacts 4625 provided to the dock connector 4600 of the air delivery tube 4170 in use; and a second end portion 6947 adapted to engage with respective contacts in communication with electrical power and electrical signalling within the reservoir dock 6050, e.g., the PCBA.

In the illustrated example, as shown in FIGS. 12-4 to 12-7, the air delivery tube 4170 includes a dock connector 4600 to connect the air delivery tube 4170 to the reservoir dock 6050. The dock connector 4600 includes a tubular base portion 4680 and a locking lever 4690 resiliently supported on a superior side of the tubular base portion 4680. The locking lever 4690 includes a retaining protrusion 4692 at one end of the locking lever 4690 and a finger/thumb grip 4694 at the other end of the locking lever 4690. The locking lever 4690 is resiliently biased to a locked position.

A circumferential lip seal 4675 is provided to the tubular base portion 4680 and protrudes into the opening of the base portion 4680. In use, the circumferential lip seal 4675 is structured to resiliently deform upon engagement with the outlet tube 6922 of the intermediate component 6900 so as to provide a pneumatic connection with the intermediate component 6700. Also, as best shown in FIG. 12-6, a radial stop wall 4685 is provided to the tubular base portion 4680 and protrudes into the opening of the base portion 4680. In use, the radial stop wall 4685 provides a stop to prevent the dock connector 4600 from inserting further into the intermediate component 6900.

Also, electrical contacts 4625 are provided to a superior side of the opening of the base portion 4680. In an example, the contacts 4625 may be connected to respective wires running along the air delivery tube 4170, e.g., configured to heat air in the air delivery tube and/or transmit signal from one or more transducers (e.g., temperature sensor, flow sensor). When the tube 4170 is brought into contact with the reservoir dock 6050, the contacts 4625 engage contacts 6945 provided to the intermediate component 6900 to provide electrical power and/or control signal transmission.

In the illustrated example, as shown in FIG. 12-6, the base portion 4680, locking lever 4690, and stop wall 4685 may comprise a base mold constructed of a relatively rigid material (e.g., thermoplastic polymer (e.g., PC, ABS)) and the circumferential lip seal 4675 and soft exterior portions may comprise an overmold constructed of a relatively soft material (e.g., thermoplastic elastomer (TPE) or silicone) that is provided (e.g., by overmolding) to the base mold.

To engage the dock connector 4600 of the air delivery tube 4170 with the reservoir dock 6050, the dock connector 4600 is oriented to align its locking lever 4690 with the retaining protrusion 6930 provided to the intermediate component 6900 at the dock outlet 6090 of the reservoir dock 6050 (e.g., see FIG. 12-1). The dock connector 4600 is then pushed towards the reservoir dock 6050 so that the free end of tubular base portion 4680 extends into the channel 6925 formed by the outlet tube 6922 and the annular side wall 6924 of the intermediate component 6900, and the outlet tube 6922 of the intermediate component 6900 extends into the opening of the tubular base portion 4680.

The dock connector 4600 is pushed further towards the reservoir dock 6050 until the dock connector 4600 reaches a locked position (e.g., see FIG. 12-2). When the dock connector 4600 reaches the locked position, the retaining protrusion 4692 of the locking lever 4690 is configured and arranged to engage over and behind the retaining protrusion 6930 provided to the intermediate component 6900, e.g., see FIG. 12-7. The retaining protrusion 4692 of the locking lever 4690 and the retaining protrusion 6930 of the intermediate component 6900 each include a taper to facilitate engagement into the locked position. This connection releasably secures the air delivery tube 4170 to the reservoir dock 6050. The finger/thumb grip 4694 can be manually depressed to pivot the locking lever 4690 and hence the retaining protrusion 4692 against biasing into an unlocked position to allow the air delivery tube 4170 to be removed from the reservoir dock 6050.

When the dock connector 4600 reaches the locked position, the circumferential lip seal 4675 engages with the outlet tube 6922 of the intermediate component 6900 so as to provide a pneumatic connection with the intermediate component 6700 (see FIG. 12-7). In addition, when the dock connector 4600 reaches the locked position, the contacts 4625 engage with contacts 6945 provided to the intermediate component 6900 to provide electrical power and/or control signal transmission (see FIG. 12-7). Thus, in this example, the mechanical, pneumatic, and electrical connections are formed substantially simultaneously. However, it should be appreciated that, by changing the location, orientation and configurations of the components, one or more of these connections may be formed in series.

Figures 5, 6, 7, 8, 9, 10, 11, 12, 13, 14, 15:
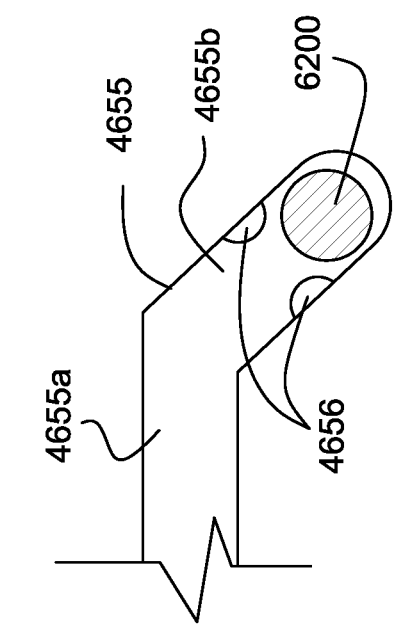
Figures 5, 7:
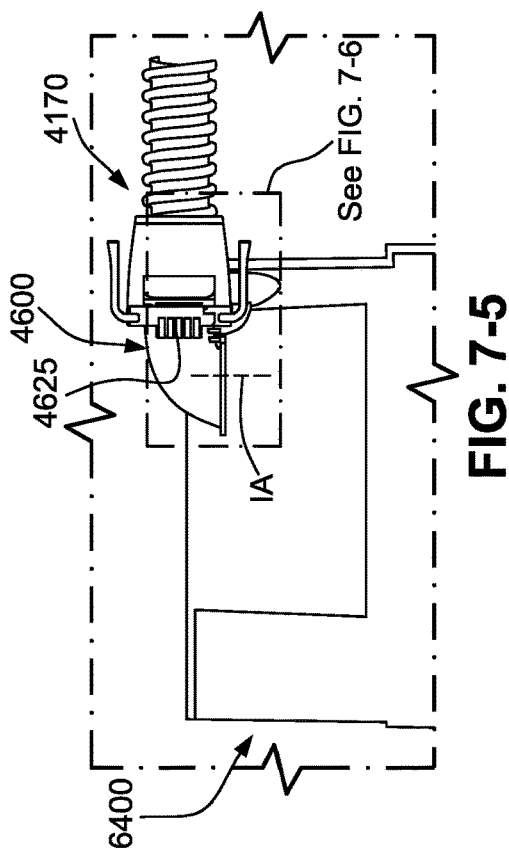
Figure 7:
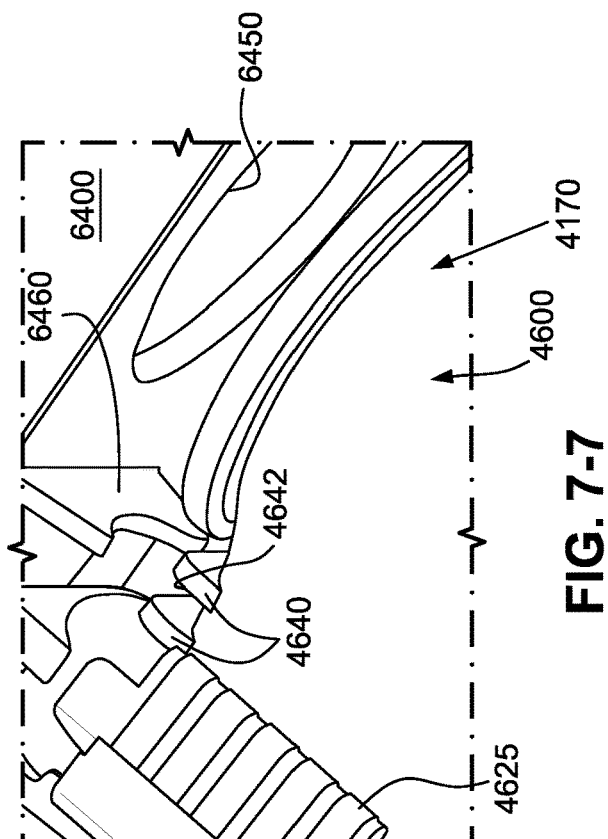
Figures 4, 7:
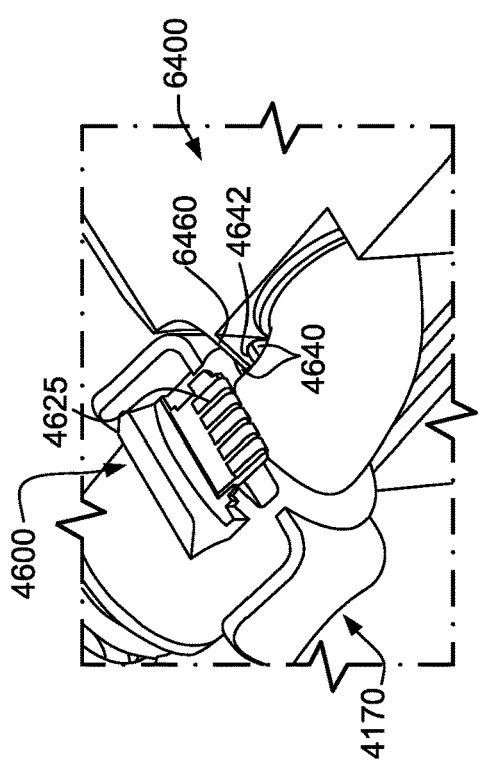
Figures 6, 7:
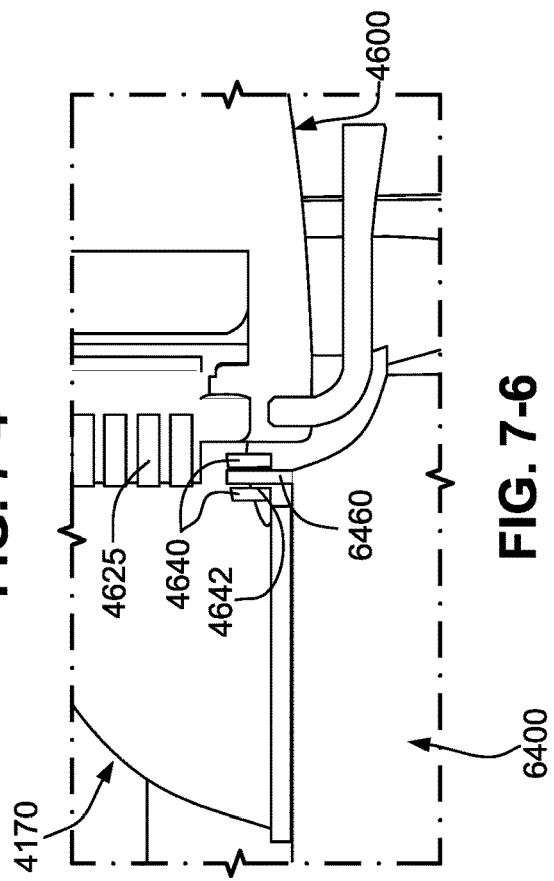

In above-identified examples, the dock connector 4600 of the air delivery tube 4170 includes a contact support structure (e.g., tongue structure, plug, pad) that is structured and arranged to support contacts for electrical power and/or control signal transmission. It should be appreciated that the contact support structure and/or the contacts may have alternative configurations and arrangements, e.g., depending on the interface arrangement or connection mechanism provided at the dock outlet 6090 of the reservoir dock 6050. For example, FIGS. 13-1 to 13-3, 14-1 to 14-6, and 15-1 to 15-3 show contact support structures 4623 and contacts 4625 according to three alternative examples of the present technology. In these examples, the tracks of the contacts 4625 are elevated (spaced away from the main body of the cuff or dock connector). In FIGS. 13-1 to 13-3, the contact support structure 4623 is in the form of a pad that is integral with the connector. The pad includes electrical contacts 4625 that can be arranged either transversely (FIG. 13-2) or in parallel (e.g., as in FIG. 14-2) to a longitudinal axis of the dock connector 4600. Whilst both arrangements are generally suitable for any type of engagements, in some cases the parallel arrangement may be more suitable for a direct (straight) engagement with the dock connector 4600, whilst the transverse electrical connectors may be more suitable for a bayonet (rotatable) type connection. In FIGS. 14-1 to 14-3, the contact support structure 4623 is elevated above the underlying connector and is supported by a supporting wall 4624 at least on one side. As best shown in FIGS. 14-4 to 14-6, for strength and rigidity, the supporting wall 4624 may extend on two sides of the contact support structure 4623. The presence of space under the contact support structure 4623 in this specific configuration is best suited for a bayonet-type connection, in which an engagement wall of the reservoir dock may enter this space under (i.e., upon a rotation of the dock connector) and present a locking surface that locks the contact support structure 4623, and therefore the entire dock connector, into the rotated position. In a preferred case, this rotated position may be the one in which the dock connector is electrically connected to the reservoir dock. In FIGS. 15-1 to 15-3, the contact support structure 4623 is in the form of a clip arm (e.g., attached to the airway tube by way of a loose (flexible) link and arranged for a snap-fit or clip type connection) with contacts 4625 arranged generally parallel to a longitudinal axis of the dock connector 4600. The electrical contacts 4625 in the arrangement illustrated by both FIGS. 14-1 to 14-3 and 15-1 to 15-3, can again be arranged either transversely (FIG. 13-2) or in parallel (e.g., as in FIG. 14-2).

In the above examples, a number of arrangements were described where the pneumatic and electrical connections, needed for the full operation of a RPT device with a heated tube, are effected either simultaneously or in series (sequentially). Among the possible advantages of the latter (in series) arrangements is the fact that the two systems of the device, the electrical and the pneumatic one, may be able to be isolated from one another and trouble-shooted independently.

Whilst most of the above described examples were based on a description of the air delivery tube being attachable to a water reservoir dock, it should be appreciated that in some air delivery systems there is no humidification and water reservoir present in the system. In this case, the air delivery tube is directly or indirectly connectable to a tube engagement dock of the RPT device. All of the above disclosure related to the water reservoir connecting dock is also applicable to the respective tube engagement dock of the RPT device in such cases.

Also, the RPT device and/or humidifier provides one form of connection or engagement port for connecting to the air circuit or air delivery tube 4170, i.e., the place where the air delivery tube 4170 engages with the RPT device and/or humidifier. In the described examples, the connection or engagement port may comprise the outlet port 6500 associated with the water reservoir or outlet muffler (e.g., see FIGS. 5-2, 6-2, 9-3), the outlet 6450 of the water reservoir 6400 (e.g., see FIG. 7-7), or the intermediate component 6900 (e.g., see FIG. 12-1), for example. The function of the connection or engagement port is to pass on pressurized air generated in the RPT device to the air delivery tube and the patient interface, and as such may be used with an RPT device with or without a humidifier. In examples, the connection or engagement port may also locate, secure and/or electrically connect to the air delivery tube. Also, it should be appreciated that the connection or engagement port may be located anywhere on the RPT device and/or humidifier, as long as it is communicated (e.g., via one or more intermediate connectors) with the pressurized flow source of the RPT device and/or the humidifier (e.g., water reservoir). For example, the connection or engagement port may form part of the water reservoir dock, or may be positioned elsewhere (i.e., not be part of the water reservoir dock) and communicated with the water reservoir dock, water reservoir thereof or the pneumatic block of the RPT device.

5.6.2.4 Water Level Indicator

The humidifier reservoir 5110 may comprise a water level indicator. In some forms, the water level indicator may provide one or more indications to a user such as the patient 1000 or a care giver regarding a quantity of the volume of water in the humidifier reservoir 5110. The one or more indications provided by the water level indicator may include an indication of a maximum, predetermined volume of water, any portions thereof, such as 25%, 50% or 75% or volumes such as 200 ml, 300 ml or 400 ml.

5.6.2.5 Humidifier Transducer(s)

As shown in FIG. 4, the humidifier 5000 may comprise one or more humidifier transducers (sensors) 5210 instead of, or in addition to, transducers provided in the RPT device 4000. Humidifier transducers 5210 may include one or more of an air pressure sensor 5212, an air flow rate transducer 5214, a temperature sensor 5216, or a humidity sensor 5218 as shown in FIG. 4. A humidifier transducer 5210 may produce one or more output signals which may be communicated to a controller such as the central controller of the RPT device 4000 and/or a humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor provided in the RPT device 4000.

5.6.2.5.2 Flow Rate Transducer

One or more flow rate transducers 5214 may be provided to the humidifier 5000 in addition to, or instead of, a flow rate sensor provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base where heat may be provided to the humidifier reservoir 5110 primarily by conduction.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal (1 hectopascal=100 Pa=100 $N/m^2$=1 millibar 0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240. (Year? Required?)

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| REFERENCE SIGNS LIST | |
|---|---|
| Feature Item | Number |
| patient | 1000 |
| bed partner | 1100 |
| patient interface | 3000 |
| seal - forming structure | 3100 |
| positioning and stabilizing structure | 3300 |
| vent | 3400 |
| connection port | 3600 |
| forehead support | 3700 |
| RPT device | 4000 |
| main panel | 4010 |
| front panel | 4012 |
| side panel | 4014 |
| chassis | 4016 |
| pneumatic block | 4020 |
| outlet muffler | 4124 |
| air delivery tube | 4170 |
| PCBA | 4202 |
| input devices | 4220 |
| output device | 4290 |
| tube portion | 4500 |
| dock connector | 4600 |
| cuff body | 4610 |
| catch | 4611 |
| pinch arms | 4615 |
| electrical plug | 4620 |
| electrical pad | 4621 |
| contact support structure | 4623 |
| supporting wall | 4624 |
| contacts | 4625 |
| inlet portion | 4630 |
| inlet tube | 4632 |
| flange | 4635 |
| contact surface | 4636 |
| side walls | 4640 |
| recess | 4642 |
| locking collar | 4650 |
| gap | 4651 |
| cut - out | 4652 |
| guide slot | 4655 |
| guiding section | 4655a |
| locking section | 4655b |
| bumps | 4656 |
| recess | 4657 |
| locking pins | 4670 |
| locking pin | 4670 |
| lip seal | 4675 |
| base portion | 4680 |
| stop wall | 4685 |
| locking lever | 4690 |
| retaining protrusion | 4692 |
| grip | 4694 |
| humidifier | 5000 |
| water reservoir | 5110 |
| heater plate | 5120 |
| water reservoir dock | 5130 |
| conductive portion | 5150 |
| cavity | 5160 |
| dock air outlet | 5168 |
| dock air inlet | 5170 |
| humidifier outlet | 5172 |
| humidifier transducer | 5210 |
| pressure transducer | 5212 |
| flow rate transducer | 5214 |
| temperature transducer | 5216 |
| humidity sensor | 5218 |
| heating element | 5240 |

REFERENCE SIGNS LIST

| Feature Item | Number |
|---|---|
| humidifier controller | 5250 |
| central humidifier controller | 5251 |
| heating element controller | 5252 |
| air circuit controller | 5254 |
| integrated RPT device and humidifier | 6000 |
| reservoir dock | 6050 |
| recesses | 6065 |
| upper edge | 6067 |
| opening | 6068 |
| edge | 6069 |
| dock outlet | 6090 |
| annular side wall | 6100 |
| opening | 6115 |
| pad receiving recess | 6117 |
| pin receiving recess | 6119 |
| locking pin | 6200 |
| electrical socket | 6300 |
| contacts | 6310 |
| water reservoir | 6400 |
| outlet | 6450 |
| locking protrusion | 6460 |
| outlet port | 6500 |
| outlet portion | 6510 |
| outlet tube | 6512 |
| outlet seal | 6515 |
| locking and contact assembly | 6600 |
| locking lever | 6650 |
| push button | 6652 |
| lock arm | 6654 |
| stop arm | 6656 |
| spring | 6660 |
| locking latch | 6700 |
| retaining protrusion | 6710 |
| locking button | 6800 |
| top wall | 6810 |
| outer side walls | 6820 |
| inner side walls | 6830 |
| retaining protrusion | 6832 |
| stop protrusion | 6834 |
| guide slot | 6840 |
| guiding section | 6840G |
| locking section | 6840L |
| transition section | 6840T |
| intermediate component | 6900 |
| inlet end | 6910 |
| contact surface | 6912 |
| outlet end | 6920 |
| outlet tube | 6922 |
| annular side wall | 6924 |
| recess | 6925 |
| retaining protrusion | 6930 |
| contact assembly | 6940 |
| support member | 6942 |
| contacts | 6945 |
| first end portion | 6946 |
| second end portion | 6947 |

The invention claimed is:

1. An apparatus for generating and providing a pressurized breathable gas to a patient's airways, the apparatus comprising:

a respiratory pressure therapy (RPT) device having an engagement port pneumatically and electrically coupled to the RPT device; and an air delivery tube configured to engage the engagement port of the RPT device so as to pass a flow of breathable gas to a patient interface, the air delivery tube comprising electric contacts associated with a heating and/or a sensing arrangement, wherein the engagement port includes a locking latch pivotally movable between (1) an unlocked position to allow connection of the air delivery tube to the engagement port and disconnection of the air delivery tube from the engagement port, and (2) a locked position to releasably lock the air delivery tube to the engagement port, wherein the air delivery tube is structured and arranged to electrically connect to the engagement port when the air delivery tube is engaged with the engagement port and the locking latch is in the unlocked position, wherein, when the locking latch is pivoted into the locked position, the locking latch is configured and arranged to allow the air delivery tube to pneumatically connect to the engagement port, and wherein said pneumatic connection between the air delivery tube and the engagement port is only effected after the locking latch is pivoted into the locked position.

2. The apparatus according to claim 1, wherein the RPT device comprises an engagement dock, and the engagement port forms part of the engagement dock.

3. The apparatus according to claim 2, wherein the engagement dock is in the form of a water reservoir dock structured and arranged to receive a water reservoir in an operative position, the water reservoir including a cavity structured to hold a volume of water, such that in an operational configuration the water reservoir is in pneumatic connection with the engagement dock and with the air delivery tube.

4. The apparatus according to claim 1, wherein the air delivery tube is structured and arranged to form electrical and pneumatic connections in series.

5. The apparatus according to claim 1, wherein the locking latch includes a stop arm to prevent the pneumatic connection when the locking latch is in the unlocked position.

6. The apparatus according to claim 1, wherein each of the connection and disconnection of the air delivery tube includes two independent user movements, one for pneumatic connection/disconnection and one for electrical connection/disconnection.

7. The apparatus according to claim 6, wherein the two independent user movements are in one plane or in two substantially transverse planes.

* * * * *